United States Patent
Mita et al.

(10) Patent No.: US 9,637,480 B2
(45) Date of Patent: May 2, 2017

(54) PARASITE- AND HYGIENIC PEST-CONTROLLING AGENT

(75) Inventors: Takeshi Mita, Funabashi (JP);
Yukihiro Maizuru, Funabashi (JP);
Ken-ichi Toyama, Funabashi (JP);
Motoyoshi Iwasa, Funabashi (JP);
Hotaka Imanaka, Minamisaitama-gun (JP); Hiroto Matsui, Minamisaitama-gun (JP)

(73) Assignee: NISSAN CHEMICAL INDUSTRIES, LTD., Tokyo (JP)

(*) Notice: Subject to any disclaimer, the term of this patent is extended or adjusted under 35 U.S.C. 154(b) by 681 days.

(21) Appl. No.: 13/885,184

(22) PCT Filed: Nov. 18, 2011

(86) PCT No.: PCT/JP2011/076690
§ 371 (c)(1),
(2), (4) Date: Sep. 4, 2013

(87) PCT Pub. No.: WO2012/067235
PCT Pub. Date: May 24, 2012

(65) Prior Publication Data
US 2013/0338197 A1    Dec. 19, 2013

(30) Foreign Application Priority Data

Nov. 19, 2010 (JP) .................. 2010-258547
Jul. 21, 2011 (JP) .................. 2011-159524

(51) Int. Cl.
| | |
|---|---|
| A61K 31/42 | (2006.01) |
| A61K 31/435 | (2006.01) |
| C07D 413/12 | (2006.01) |
| C07D 207/18 | (2006.01) |
| C07D 261/04 | (2006.01) |
| C07D 401/04 | (2006.01) |
| C07D 401/14 | (2006.01) |

(Continued)

(52) U.S. Cl.
CPC ........... *C07D 413/12* (2013.01); *A01N 43/36* (2013.01); *A01N 43/56* (2013.01); *A01N 43/76* (2013.01); *A01N 43/78* (2013.01); *A01N 43/80* (2013.01); *A61K 31/42* (2013.01); *A61K 31/435* (2013.01); *C07D 207/18* (2013.01); *C07D 261/04* (2013.01); *C07D 401/04* (2013.01); *C07D 401/14* (2013.01); *C07D 409/14* (2013.01); *C07D 413/04* (2013.01); *C07D 413/14* (2013.01)

(58) Field of Classification Search
CPC ...... A61K 31/05; A61K 31/42; A61K 31/435; A61K 31/495; A61K 31/53
See application file for complete search history.

(56) References Cited

U.S. PATENT DOCUMENTS

| | | |
|---|---|---|
| 7,951,828 B1 | 5/2011 | Mita et al. |
| 7,964,204 B2 | 6/2011 | Lahm et al. |
| 2007/0066617 A1 | 3/2007 | Mita et al. |
| 2009/0143410 A1 | 6/2009 | Patel |

FOREIGN PATENT DOCUMENTS

| | | |
|---|---|---|
| JP | A-2007-91708 | 4/2007 |
| JP | A-2007-308471 | 11/2007 |

(Continued)

OTHER PUBLICATIONS

International Search Report issued in International Patent Application No. PCT/JP2011/076690 dated Feb. 28, 2012.
Written Opinion of the International Searching Authority issued in International Patent Application No. PCT/JP2011/076690 dated Feb. 28, 2012.

*Primary Examiner* — Yong Chong
(74) *Attorney, Agent, or Firm* — Oliff PLC

(57) ABSTRACT

There is provided a novel agent for controlling harmful arthropods or nematodes that are parasites and hygienic pests for animals. An ecto- or endo-parasiticide for mammals or the like comprising as active ingredient, one or more selected from substituted benzamide compounds of formula (1) or salts thereof:

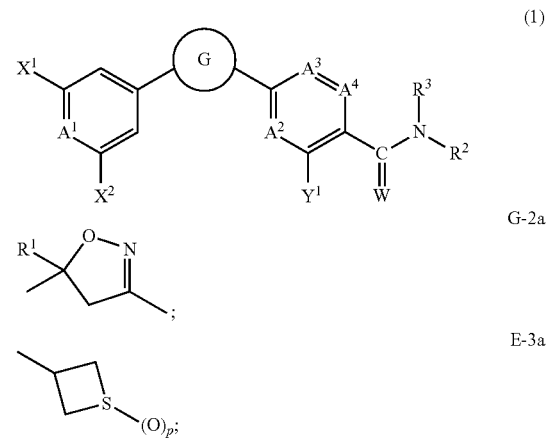

wherein $A^1$ is $C-X^3$ or nitrogen atom, etc., $A^2$ and $A^3$ are $C-H$, etc., $A^4$ is $C-H$ or nitrogen atom, etc., G is G-2a, etc., W is oxygen atom or sulfur atom, $X^1$ is halogen atom, trifluoromethyl, etc., $X^2$ is hydrogen atom, halogen atom, trifluoromethyl, etc., $X^3$ is hydrogen atom, halogen atom, etc., $Y^1$ is hydrogen atom, halogen atom, methyl, etc., $R^1$ is trifluoromethyl, etc., $R^2$ is E-3a, etc., $R^3$ is hydrogen atom, etc., p is an integer of 0 to 2.

17 Claims, No Drawings

(51) Int. Cl.
  *C07D 413/04*  (2006.01)
  *C07D 413/14*  (2006.01)
  *A01N 43/36*  (2006.01)
  *A01N 43/56*  (2006.01)
  *A01N 43/76*  (2006.01)
  *A01N 43/78*  (2006.01)
  *A01N 43/80*  (2006.01)
  *C07D 409/14*  (2006.01)

(56) References Cited

FOREIGN PATENT DOCUMENTS

| | | |
|---|---|---|
| JP | A-2009-519937 | 5/2009 |
| JP | A-2009-522282 | 6/2009 |
| JP | A-2010-168367 | 8/2010 |
| WO | WO 2005/085216 A1 | 9/2005 |
| WO | WO 2007/070606 A2 | 6/2007 |
| WO | WO 2007/079162 A1 | 7/2007 |
| WO | WO 2008/154528 A2 | 12/2008 |
| WO | WO 2009/002809 A2 | 12/2008 |
| WO | WO 2009/003075 A1 | 12/2008 |
| WO | WO 2009/080250 A2 | 7/2009 |
| WO | WO 2009/126668 A2 | 10/2009 |
| WO | WO 2010/003877 A1 | 1/2010 |
| WO | WO 2010/003923 A1 | 1/2010 |
| WO | WO 2010/020521 A1 | 2/2010 |
| WO | WO 2010/020522 A1 | 2/2010 |
| WO | WO 2010/025998 A1 | 3/2010 |
| WO | WO 2010/026403 A1 | 3/2010 |
| WO | WO 2010/084067 A2 | 7/2010 |
| WO | WO 2010/086225 A1 | 8/2010 |
| WO | WO 2010/108733 A1 | 9/2010 |
| WO | WO 2010/149506 A1 | 12/2010 |
| WO | WO 2011/054871 A1 | 5/2011 |
| WO | WO 2011/067272 A1 | 6/2011 |
| WO | WO 2011/075591 A1 | 6/2011 |
| WO | WO 2011/101229 A1 | 8/2011 |
| WO | WO 2011/101402 A1 | 8/2011 |
| WO | WO 2011/104087 A1 | 9/2011 |
| WO | WO 2011/104088 A1 | 9/2011 |
| WO | WO 2011/104089 A1 | 9/2011 |
| WO | WO 2011/128299 A1 | 10/2011 |
| WO | WO 2011/141414 A1 | 11/2011 |
| WO | WO 2011/154433 A2 | 12/2011 |
| WO | WO 2011/154434 A2 | 12/2011 |
| WO | WO 2011/154494 A2 | 12/2011 |
| WO | WO 2011/157733 A2 | 12/2011 |
| WO | WO 2012/007426 A1 | 1/2012 |
| WO | WO 2012/038851 A1 | 3/2012 |
| WO | WO 2012/047543 A1 | 4/2012 |
| WO | WO 2012/049327 A2 | 4/2012 |
| WO | WO 2012/067235 A1 | 5/2012 |
| WO | WO 2012/104331 A2 | 8/2012 |
| WO | WO 2012/163945 A1 | 12/2012 |
| WO | WO 2012/163948 A1 | 12/2012 |
| WO | WO 2012/163960 A1 | 12/2012 |

PARASITE- AND HYGIENIC PEST-CONTROLLING AGENT

TECHNICAL FIELD

The present invention relates to an agent for controlling harmful parasites that parasitize animals and for controlling hygienic pests.

BACKGROUND ART

Substituted benzamide compounds of formula (1) or the salts thereof that are contained as active ingredient in the parasite- and hygienic pest-controlling agent of the present invention are known compounds, and the effectiveness thereof as agricultural and horticultural insecticide or miticide is known (see, for example Patent Documents 1-9).

However, Patent Documents 1-9 do not concretely disclose an effect of controlling parasites and hygienic pests to which the present invention is related.

PRIOR ART DOCUMENT

Patent Document

Patent Document 1: WO 2009/080250 Pamphlet
Patent Document 2: WO 2010/020521 Pamphlet
Patent Document 3: WO 2010/020522 Pamphlet
Patent Document 4: WO 2010/025998 Pamphlet
Patent Document 5: WO 2010/084067 Pamphlet
Patent Document 6: WO 2010/086225 Pamphlet
Patent Document 7: WO 2010/108733 Pamphlet
Patent Document 8: WO 2010/149506 Pamphlet
Patent Document 9: WO 2011/067272 Pamphlet

SUMMARY OF INVENTION

Problems to be Solved by the Invention

It is an important subject to expel harmful parasites that parasitize animals in order to maintain health of the targeted animals, and also in order to produce stably safe foods, or living materials such as high quality wool, feather, leather or the like, in case where the target animals are domestic animals and domestic fowls. On the other hand, it is also an important subject to expel hygienic pests in human living environment in order to maintain human healthy living environment, for example to prevent the spread of infection transmitted by hygienic pests, to prevent pollution of foods by contact with hygienic pests, or to prevent causing harm on clothes or residences, etc. by hygienic pests, and the like. From such a viewpoint, hitherto, parasite-controlling agents and hygienic pest-controlling agents for expelling harmful parasites and hygienic pests have been developed, and effective agents have been practically used until now.

However, as those agents have been used over the years, recently parasites and hygienic pests have acquired resistance to those agents, the scenes that it becomes difficult to expel with the agents that have been hitherto used have increased. Under such situations, it is expected all the time to develop novel parasite- and hygienic pest-controlling agents that have not only excellent controlling activity against parasites and hygienic pests, but also advanced controlling characteristics such as low toxicity and low persistence, or the like, and to develop effective control methods.

Means for Solving the Problems

The inventors have eagerly investigated in order to solve the above-mentioned problems, and as a result of it, they found that compositions comprising active ingredients containing substituted benzamide compounds of formula (I) described below and salts thereof, or mixtures containing two or more selected from the above-mentioned compounds and salts, and one or more constitutional ingredients selected from surfactants, solid carriers and liquid carriers, and optionally as an additional ingredient, an effective amount of one or more known parasite- and hygienic pest-controlling agents show an excellent parasite- and hygienic pest-controlling activity, and particularly oral administration or parenteral administration of an effective amount of the compositions to targeted animals exhibits extremely excellent parasite- and hygienic pest-controlling activity. Thus, the present invention has been accomplished.

That is, the present invention relates to a parasite- and hygienic pest-controlling composition containing as active ingredient, a substituted benzamide compound of formula (1) or a salt thereof:

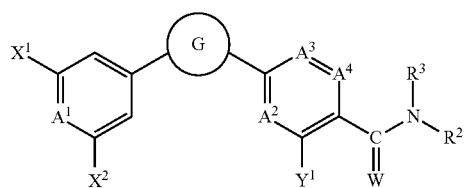

wherein $A^1$ is C—$X^3$ or nitrogen atom,
$A^2$, $A^3$ and $A^4$ are independently of one another C—$Y^2$ or nitrogen atom,
G is a heterocyclic ring of following structural formulae G-1 to G-7:

G-1

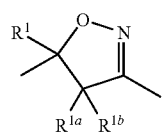

G-2

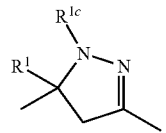

G-3

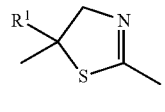

G-4

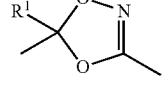

G-5

-continued

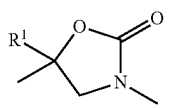
G-6

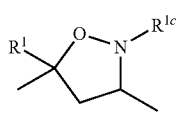
G-7

W is oxygen atom or sulfur atom, $X^1$ is hydrogen atom, halogen atom, $C_1$-$C_3$haloalkyl, halocyclopropyl, —$OR^4$, —$SF_5$ or $C_1$-$C_3$haloalkylthio, $X^2$ is hydrogen atom, halogen atom, cyano, nitro, $C_1$-$C_3$alkyl, $C_1$-$C_3$haloalkyl, —$OR^4$, —$S(O)_pR^4$ or —$NH_2$, $X^3$ is hydrogen atom, halogen atom, cyano, methyl, methoxy, difluoromethoxy, methylthio, —$NH_2$ or dimethylamino, or $X^3$ together with $X^1$ optionally forms 5-membered or 6-membered ring together with carbon atoms to which each of $X^1$ and $X^3$ is bonded by forming —$CF_2OCF_2$—, —$OCF_2O$—, —$CF_2OCF_2O$— or —$OCF_2CF_2O$—, $Y^1$ is hydrogen atom, halogen atom, cyano, nitro, $C_1$-$C_3$alkyl, $C_1$-$C_3$haloalkyl, ($C_1$-$C_2$)alkyl substituted with $R^5$, $C_3$-$C_4$cycloalkyl, $C_1$-$C_3$alkoxy, $C_1$-$C_3$haloalkoxy, $C_1$-$C_3$alkylthio, $C_1$-$C_3$haloalkylthio, —$N(R^7)R^6$, —$C(S)NH_2$, $C_2$-$C_3$alkynyl, trimethylsilylethynyl, phenyl, phenyl substituted with $(Z)_{n1}$ or D, D is an aromatic heterocyclic ring of following structural formulae D-1 to D-3, D-7, D-11 and D-19 to D-23:

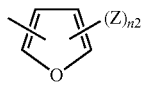
D-1

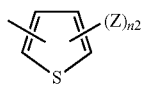
D-2

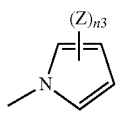
D-3

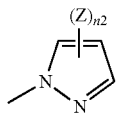
D-7

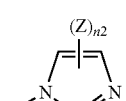
D-11

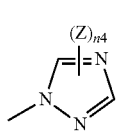
D-19

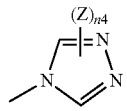
D-20

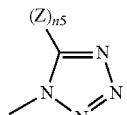
D-21

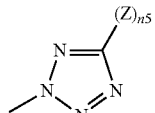
D-22

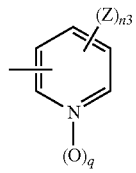
D-23

Z is halogen atom, cyano, nitro, methyl, trifluoromethyl, methoxy, methylthio, methylsulfinyl, methylsulfonyl, —$NH_2$ or dimethylamino, when n1 to n4 are an integer of 2 or more, each Z may be identical with or different from each other, $Y^2$ is hydrogen atom, halogen atom or methyl, or when two $Y^2$s are adjacent, the adjacent two $Y^2$s may form 5-membered or 6-membered ring together with carbon atoms to which the two $Y^2$s are bonded by forming =NSN= or —CH=CHCH=CH—, in this case, hydrogen atoms bonded to each carbon atom forming the ring may be arbitrarily substituted with Z, further when it is substituted with two or more Zs, each Z may be identical with or different from each other, $R^1$ is $C_1$-$C_3$haloalkyl or halocyclopropyl, $R^{1a}$ is hydrogen atom, halogen atom, $C_1$-$C_3$alkyl, $C_1$-$C_3$alkylthiomethyl, $C_1$-$C_3$haloalkylthiomethyl, $C_1$-$C_3$alkylsulfinylmethyl, $C_1$-$C_3$haloalkylsulfinylmethyl, $C_1$-$C_3$alkylsulfonylmethyl, $C_1$-$C_3$haloalkylsulfonylmethyl, —OH, $C_1$-$C_3$alkylthio or $C_1$-$C_3$alkylsulfonyl, $R^{1b}$ is hydrogen atom or halogen atom, or $R^{1b}$ together with $R^{1a}$ optionally forms $C_1$-$C_4$alkylidene, phenylmethylidene, hydroxyimino or $C_1$-$C_3$alkoxyimino, $R^{1c}$ is $C_1$-$C_3$alkyl, $R^2$ is E or ($C_1$-$C_3$)alkyl substituted with E, E is a heterocyclic ring of following structural formulae E-1 to E-13:

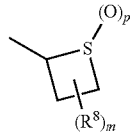
E-1

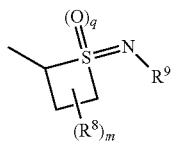
E-2

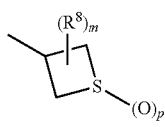
E-3

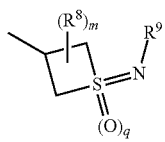
E-4

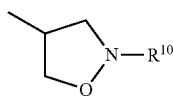
E-5

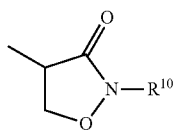
E-6

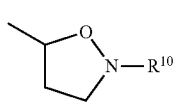
E-7

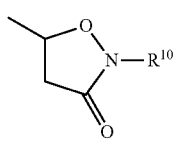
E-8

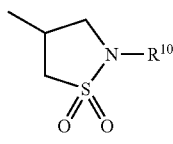
E-9

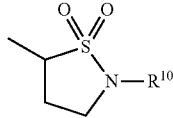
E-10

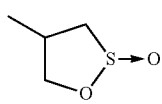
E-11

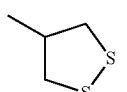
E-12

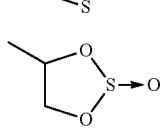
E-13

$R^3$ is hydrogen atom, $C_1$-$C_4$alkyl, ($C_1$-$C_2$)alkyl substituted with $R^{11}$, $C_3$-$C_4$cycloalkyl, $C_3$-$C_4$alkenyl, $C_3$-$C_4$alkynyl, —C(O)$R^{12}$, —C(O)O$R^{13}$, —C(O)C(O)O$R^{13}$ or $C_1$-$C_3$haloalkylthio, $R^4$ is $C_1$-$C_3$alkyl, $C_1$-$C_3$haloalkyl or $C_1$-$C_3$haloalkoxy ($C_1$-$C_2$)haloalkyl, $R^5$ is —OH, $C_1$-$C_3$alkoxy, $C_1$-$C_3$haloalkoxy, $C_1$-$C_3$alkylthio or $C_1$-$C_3$haloalkylthio, $R^6$ is hydrogen atom, $C_1$-$C_4$alkyl, —CHO, $C_1$-$C_3$alkylcarbonyl, $C_1$-$C_3$haloalkylcarbonyl, $C_3$-$C_4$cycloalkylcarbonyl, $C_1$-$C_3$alkoxycarbonyl, $C_1$-$C_3$alkylthiocarbonyl, $C_1$-$C_3$alkoxythiocarbonyl, $C_1$-$C_3$alkyldithiocarbonyl, $C_1$-$C_3$alkylsulfonyl or $C_1$-$C_3$haloalkylsulfonyl, $R^7$ is hydrogen atom or $C_1$-$C_3$alkyl, $R^8$ is $C_1$-$C_3$alkyl, $R^9$ is hydrogen atom, cyano or $C_1$-$C_2$haloalkylcarbonyl, $R^{10}$ is hydrogen atom, $C_1$-$C_4$alkyl, $C_1$-$C_4$haloalkyl, hydroxy ($C_1$-$C_2$)alkyl, $C_1$-$C_3$alkoxy ($C_1$-$C_2$)alkyl, benzyl, $C_3$-$C_4$cycloalkyl, oxetan-3-yl, thietan-3-yl, $C_3$-$C_4$alkynyl, $C_3$-$C_4$alkenyl, phenyl or phenyl substituted with $(Z)_{n1}$, $R^{11}$ is cyano, $C_3$-$C_4$cycloalkyl, —O$R^{14}$, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl, $C_1$-$C_3$haloalkylsulfonyl, $C_1$-$C_3$alkoxycarbonyl, —C(O)NH$_2$, —C(S)NH$_2$, phenyl or D-23, $R^{12}$ is hydrogen atom, $C_1$-$C_4$alkyl, $C_1$-$C_4$haloalkyl, $C_1$-$C_3$alkoxy ($C_1$-$C_2$)alkyl, $C_1$-$C_3$alkylthio ($C_1$-$C_2$)alkyl, $C_1$-$C_3$alkylsulfinyl ($C_1$-$C_2$)alkyl, $C_1$-$C_3$alkylsulfonyl ($C_1$-$C_2$)alkyl, $C_3$-$C_6$cycloalkyl, $C_2$-$C_4$alkenyl, $C_2$-$C_4$alkynyl, phenyl, phenyl substituted with $(Z)_{n1}$, D-1, D-2 or D-23, $R^{13}$ is $C_1$-$C_4$alkyl, $C_1$-$C_4$haloalkyl, $C_1$-$C_3$alkoxy ($C_1$-$C_2$) alkyl, $C_3$-$C_4$alkenyl, $C_3$-$C_4$alkynyl or phenyl, $R^{14}$ is hydrogen atom, $C_1$-$C_4$alkyl, $C_1$-$C_4$haloalkyl, $C_3$-$C_4$alkenyl, $C_3$-$C_4$alkynyl, $C_1$-$C_4$alkylcarbonyl, $C_1$-$C_4$haloalkylcarbonyl, $C_3$-$C_6$cycloalkylcarbonyl or $C_1$-$C_4$alkoxycarbonyl, m is an integer of 0 to 5,
n1 is an integer of 1 to 5,
n2 is an integer of 0 to 3,
n3 is an integer of 0 to 4,
n4 is an integer of 0 to 2,
n5 is an integer of 0 or 1,
p is an integer of 0 to 2, and
q is an integer of 0 or 1, and a method for controlling parasites for particularly animals by use of the composition.

Effect of the Invention

The parasite- and hygienic pest-controlling composition according to the present invention exerts an excellent controlling effect against harmful parasites parasitizing animals and hygienic pests.

MODES FOR CARRYING OUT THE INVENTION

The term "animals" in the specification means companion animals and pet animals, and domestic animals and domestic fowls, and further vertebrate animals used for research and as experimental animals, or human, and more specifically means mammals, birds, reptiles, fishes, and the like.

The terms "companion animals and pet animals" in the specification mean animals that are bred for helping visually impaired persons, hearing-impaired persons and persons with impaired motor function, or for enriching human life, for example healing, calming or amusing the hearts of the people, viewing the shape or singing, making companions on human life, and the like, and include mammals such as monkey, rabbit, hamster, Mongolian gerbil, squirrel, cat, dog, ferret, etc., birds such as long-tailed fowl, pigeon, parrot, parakeet, hill myna, Bengalese finch, Java sparrow, canary, etc., reptiles such as iguana, lizard, snake, turtle, tortoise, etc., ornamental fishes such as goldfish, tropical fish, etc.

The terms "domestic animals and domestic fowls" in the specification mean animals that are artificially reproduced and bred for producing edible meat, milk, butter, egg, fur, leather, feather, wool, etc., or for working in agriculture, transportation, game, etc., and include mammals such as rabbit, chinchilla, camel, pig, reindeer, yak, cattle, buffalo, goat, sheep, mink, donkey, horse, etc., birds such as ostrich, turkey, chicken, guinea fowl, duck, goose, etc.

The terms "animals used for research and experimental animals" mean animals that are reproduced and produced for integration purpose, for research and development of medicinal drugs, animal drugs or agrochemicals, etc., for test and research as learning, or for educational or other scientific application, and include mammals such as monkey, rabbit, guinea pig, hamster, Mongolian gerbil, mouse, rat, miniature pig, dog, ferret, etc.

The term "parasites" in the specification means harmful invertebrates which parasitize the surface of the body or each organ of animals being hosts and thus inhibit healthy growth of the host animals, or spread sometimes serious diseases and in some cases lead to the death of the host animals. More specifically, the parasites means ecto-parasites represented by arthropods which directly injure skin tissues, body hairs, feathers, or suck blood from skin, such as louse fly, blowfly, sheep bot-fly, flea, biting louse, louse, feather mite, scab mite, itch mite, Cheyletidae, face mite, soft tick, hard tick, Dermanyssidae, Macronyssidae, etc., and endo-parasites which parasitize organs such as stomach, intestine, lung, vein, lymphoid tissue, subcutaneous tissue or the like, for example nematodes such as Capillaria worms, whipworms, pork worms, roundworms, pinworms, Strongyloides, hookworms, blood flukes, lungworms, blood worms, nodular worms, hair worms, Guinea worms, heartworms, or the like, Acanthocephala, Cestoidea, Trematoda, Sporozoa, Ciliophora, Mastigophora, or the like.

The term "hygienic pests" in the specification expresses harmful invertebrates which cause allergic symptoms such as intense pain, swelling or itch, etc., or occasionally cause lethal anaphylactic shock by biting targeted animals, or spread sometimes serious diseases by sucking blood, in some cases lead to the death of the animals, invertebrates which occasionally pollute with pathogen such as virus, bacteria, parasite, etc. with contact with foods, invertebrates which cause allergic diseases such as bronchogenic asthma, sinus infection, conjunctivitis or atopic dermatitis, etc., as allergen such as living body, dead shape, exuvia, feces or the like of invertebrates, invertebrates which cause economic damage by eating foods, clothes or houses, etc., and invertebrates which do not cause direct damage but bring discomfort by emerging or invading in human living environment. More specifically, the hygienic pests means arthropods such as ant which bites with mandible, hornet which stings with aculeus, cheyletid mite which stings with chelicera, tsetse fly, stable fly, tabanid fly, biting midge, black-fly, mosquito, bedbug, kissing bug, and trombiculid mite which suck blood from skin, house fly, blow fly and flesh fly which pollute foods through contact, glycyphagid mite, acaridmite and house dust mite the body of which becomes allergen, termite which is omnivorous and causes damages to constructions such as house, or moth fly, cockroach, pill bug, sow bug and oribatid which are undesirable pests.

The term "control" or expel" in the specification means to protect animals against injury, infection or propagation of parasites through exertion of effects such as avoidance, induction of behavior disorder, cross-fertilization disturbance, eating or blood-sucking disorder, growth inhibition, fatality, or the like.

The term "controlling method" in the specification means to administer a parasite- and hygienic pest-controlling agent for controlling parasites and hygienic pests to animals through a process such as oral administration, parenteral administration or administration of formed products. The parenteral administration includes administration by injection such as subcutaneous injection, intramuscular injection, intraperitoneal injection or intravenous injection or the like, administratin by inplants or the like, transdermal administration such as bathing or dipping, washing, spray, pour-on, spot-on and dusting, transnasal administration and suppository administration, or the like. In addition, the administration by the formed products includes administration by use of labeling apparatuses such as neck collars, halters, tail bands, limb bands and ear tags, etc.

The "halogen atom" in the specification means fluororine atom, chlorine atom, bromine atom and iodine atom. In addition, the indication of "halo" in the specification also means these halogen atoms.

In the specification, the indication of "$C_a$-$C_b$alkyl" means straight-chain or branched-chain hydrocarbon groups having carbon atom number of a to b, and includes for example methyl, ethyl, propyl, isopropyl, butyl, isobutyl, sec-butyl, tert-butyl, and the like. It is selected from the scope of the indicated carbon atom number. In the meantime, sec- means secondary, and tert- means tertiary.

In the specification, the indication of "$C_a$-$C_b$haloalkyl" means straight-chain or branched-chain hydrocarbon groups having carbon atom number of a to b that a hydrogen atom (hydrogen atoms) bonded to carbon atom is (are) arbitrarily substituted with a halogen atom (halogen atoms). In this case, if it is substituted with two or more halogen atoms, these halogen atoms may be identical with or different from each other. Concrete examples thereof are for example fluoromethyl, chloromethyl, bromomethyl, iodomethyl, difluoromethyl, dichloromethyl, trifluoromethyl, chlorodifluoromethyl, trichloromethyl, bromodifluoromethyl, 2-fluoroethyl, 2-chloroethyl, 2-bromoethyl, 2,2-difluoroethyl, 2,2-dichloroethyl, 2,2,2-trifluoroethyl, 2-chloro-2,2-difluoroethyl, 2,2,2-trichloroethyl, 2-bromo-2,2-difluoroethyl, 1,1,2,2-tetrafluoroethyl, 2-chloro-1,1,2-trifluoroethyl, pentafluoroethyl, 3-chloropropyl, 3,3,3-trifluoropropyl, 3-bromo-3,3-difluoropropyl, 2,2,3,3,3-pentafluoropropyl, 1,1,2,3,3,3-hexafluoropropyl, heptafluoropropyl, 2-fluoro-1-(fluoromethyl)ethyl, 2-chloro-1-(fluoromethyl)ethyl, 2-chloro-1-(chloromethyl)ethyl, 2,2,2-trifluoro-1-(trifluoromethyl)ethyl, 1,2,2,2-tetrafluoro-1-(trifluoromethyl)ethyl, 4-chlorobutyl, 2,2,3,3,4,4,4-heptafluorobutyl, nonafluorobutyl, 2-chloro-1-methylpropyl, and the like. It is selected from the scope of the indicated carbon atom number.

In the specification, the indication of "$C_a$-$C_b$cycloalkyl" means cyclic hydrocarbon groups having carbon atom number of a to b, and can form 3-membered to 6-membered single ring or conjugated ring structure. In addition, each ring may be arbitrarily substituted with alkyl group in the scope of the indicated carbon atom number. Concrete examples thereof are for example cyclopropyl, cyclobutyl, 1-methylcyclopropyl, 2-methylcyclopropyl, cyclopentyl, 2,2-dimethylcyclopropyl, 1-methylcyclobutyl, cyclohexyl, and the like. It is selected from the scope of the indicated carbon atom number.

In the specification, the indication of "$C_a$-$C_b$alkenyl" means straight-chain or branched-chain unsaturated hydrocarbon groups having carbon atom number of a to b and having 1 or more double bonds in the molecule. Concrete examples thereof are for example vinyl, 1-propenyl, 2-propenyl, 1-methylethenyl, 2-butenyl, 2-methyl-2-propenyl, and the like. It is selected from the scope of the indicated carbon atom number.

In the specification, the indication of "$C_a$-$C_b$alkynyl" means straight-chain or branched-chain unsaturated hydrocarbon groups having carbon atom number of a to b and having 1 or more triple bonds in the molecule. Concrete examples thereof are for example ethynyl, 1-propynyl, 2-propynyl, 1-butynyl, 2-butynyl, 3-butynyl, and the like. It is selected from the scope of the indicated carbon atom number.

In the specification, the indication of "$C_a$-$C_b$alkoxy" means alkyl-O— groups wherein the alkyl has carbon atom number of a to b, and includes for example methoxy, ethoxy, propyloxy, isopropyloxy, and the like. It is selected from the scope of the indicated carbon atom number.

In the specification, the indication of "$C_a$-$C_b$haloalkoxy" means haloalkyl-O— groups wherein the haloalkyl has carbon atom number of a to b, and includes for example difluoromethoxy, trifluoromethoxy, chlorodifluoromethoxy, bromodifluoromethoxy, 2-fluoroethoxy, 2-chloroethoxy, 2,2,2-trifluoroethoxy, 1,1,2,2-tetrafluoroethoxy, 2-chloro-1,1,2-trifluoroethoxy, 1,1,2,3,3,3-hexafluoropropyloxy, and the like. It is selected from the scope of the indicated carbon atom number.

In the specification, the indication of "$C_a$-$C_b$alkylthio" means alkyl-S— groups wherein the alkyl has carbon atom number of a to b, and includes for example methylthio, ethylthio, propylthio, isopropylthio, and the like. It is selected from the scope of the indicated carbon atom number.

In the specification, the indication of "$C_a$-$C_b$haloalkylthio" means haloalkyl-S— groups wherein the haloalkyl has carbon atom number of a to b, and includes for example difluoromethylthio, trifluoromethylthio, chlorodifluoromethylthio, bromodifluoromethylthio, 2,2,2-trifluoroethylthio, 1,1,2,2-tetrafluoroethylthio, 2-chloro-1,1,2-trifluoroethylthio, pentafluoroethylthio, 1,1,2,3,3,3-hexafluoropropylthio, heptafluoropropylthio, 1,2,2,2-tetrafluoro-1-(trifluoromethyl)ethylthio, and the like. It is selected from the scope of the indicated carbon atom number.

In the specification, the indication of "$C_a$-$C_b$alkylsulfinyl" means alkyl-S(O)— groups wherein the alkyl has carbon atom number of a to b, and includes for example methylsulfinyl, ethylsulfinyl, propylsulfinyl, isopropylsulfinyl, and the like. It is selected from the scope of the indicated carbon atom number.

In the specification, the indication of "$C_a$-$C_b$haloalkylsulfinyl" means haloalkyl-S(O)— groups wherein the haloalkyl has carbon atom number of a to b, and includes for example difluoromethylsulfinyl, trifluoromethylsulfinyl, chlorodifluoromethylsulfinyl, bromodifluoromethylsulfinyl, 2,2,2-trifluoroethylsulfinyl, 1,2,2,2-tetrafluoro-1-(trifluoromethyl)ethylsulfinyl, and the like. It is selected from the scope of the indicated carbon atom number.

In the specification, the indication of "$C_a$-$C_b$alkylsulfonyl" means alkyl-S(O)$_2$— groups wherein the alkyl has carbon atom number of a to b, and includes for example methylsulfonyl, ethylsulfonyl, propylsulfonyl, isopropylsulfonyl, and the like. It is selected from the scope of the indicated carbon atom number.

In the specification, the indication of "$C_a$-$C_b$haloalkylsulfonyl" means haloalkyl-S(O)$_2$— groups wherein the haloalkyl has carbon atom number of a to b, and includes for example difluoromethylsulfonyl, trifluoromethylsulfonyl, chlorodifluoromethylsulfonyl, bromodifluoromethylsulfonyl, 2,2,2-trifluoroethylsulfonyl, 1,1,2,2-tetrafluoroethylsulfonyl, 2-chloro-1,1,2-trifluoroethylsulfonyl, and the like. It is selected from the scope of the indicated carbon atom number.

In the specification, the indication of "$C_a$-$C_b$alkylcarbonyl" means alkyl-C(O)—groups wherein the alkyl has carbon atom number of a to b, and includes for example acetyl, propionyl, butyryl, isobutyryl, valeryl, isovaleryl, 2-methylbutanoyl, pivaloyl, and the like. It is selected from the scope of the indicated carbon atom number.

In the specification, the indication of "$C_a$-$C_b$haloalkylcarbonyl" means haloalkyl-C(O)— groups wherein the haloalkyl has carbon atom number of a to b, and includes for example fluoroacetyl, chloroacetyl, bromoacetyl, difluoroacetyl, dichloroacetyl, trifluoroacetyl, chlorodifluoroacetyl, trichloroacetyl, bromodifluoroacetyl, 3-chloropropionyl, 3,3,3-trifluoropropionyl, pentafluoropropionyl, 3-chlorobutyryl, 4-chlorobutyryl, 4,4,4-trifluorobutyryl, 2,3-dichloro-2-methylpropionyl, 3,3,3-trifluoro-2-(trifluoromethyl)propionyl, 5-chlorovaleryl, 5,5,5-trifluorovaleryl, 4,4,4-trifluoro-3-methylbutyryl, 4,4,4-trifluoro-3-(trifluoromethyl)butyryl, 4,4,4-trifluoro-2-methylbutyryl, 3-chloro-2,2-dimethylpropionyl, 3,3,3-trifluoro-2,2-dimethylpropionyl, 3,3,3-trifluoro-2-methyl-2-(trifluoromethyl)propionyl, and the like. It is selected from the scope of the indicated carbon atom number.

In the specification, the indication of "$C_a$-$C_b$cycloalkylcarbonyl" means cycloalkyl-C(O)— groups wherein the cycloalkyl has carbon atom number of a to b, and includes for example cyclopropylcarbonyl, cyclobutylcarbonyl, 1-methylcyclopropylcarbonyl, 2-methycyclopropylcarbonyl, cyclopentylcarbonyl, 2,2-dimethycyclopropylcarbonyl, cyclohexylcarbonyl, and the like. It is selected from the scope of the indicated carbon atom number.

In the specification, the indication of "$C_a$-$C_b$alkoxycarbonyl" means alkyl-O—C(O)—groups wherein the alkyl has carbon atom number of a to b, and includes for example methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, and the like. It is selected from the scope of the indicated carbon atom number.

In the specification, the indication of "$C_a$-$C_b$alkylthiocarbonyl" means alkyl-S—C(O)— groups wherein the alkyl has carbon atom number of a to b, and includes for example methylthio-C(O)—, ethylthio-C(O)—, propylthio-C(O)—, isopropylthio-C(O)—, and the like. It is selected from the scope of the indicated carbon atom number.

In the specification, the indication of "$C_a$-$C_b$alkoxythiocarbonyl" means alkyl-O—C(S)— groups wherein the alkyl has carbon atom number of a to b, and includes for example methoxy-C(S)—, ethoxy-C(S)—, propoxy-C(S)—, isopropoxy-C(S)—, and the like. It is selected from the scope of the indicated carbon atom number.

In the specification, the indication of "$C_a$-$C_b$alkyldithiocarbonyl" means alkyl-S—C(S)— groups wherein the alkyl has carbon atom number of a to b, and includes for example methylthio-C(S)—, ethylthio-C(S)—, propylthio-C(S)—, isopropylthio-C(S)—, and the like. It is selected from the scope of the indicated carbon atom number.

In the specification, the indication of "$C_a$-$C_b$alkoxyimino" means alkyl-O—N= groups wherein the alkyl has carbon atom number of a to b, and includes for example methoxyimino group, ethoxyimino group, propoxyimino group, isopropoxyimino group, and the like. It is selected from the scope of the indicated carbon atom number.

In the specification, the indication of "$C_a$-$C_b$alkylthiomethyl", "$C_a$-$C_b$haloalkylthiomethyl", "$C_a$-$C_b$halkylsulfinylmethyl", "$C_a$-$C_b$haloalkylsulfinylmethyl", "$C_a$-$C_b$alkylsulfonylmethyl" or "$C_a$-$C_b$haloalkylsulfonylmethyl" means methyl group which a hydrogen atom (hydrogen atoms) bonded to carbon atom is (are) arbitrarily substituted with the $C_a$-$C_b$alkylthio, $C_a$-$C_b$haloalkylthio, $C_a$-$C_b$alkylsulfinyl, $C_a$-$C_b$haloalkylsulfinyl, $C_a$-$C_b$alkylsulfonyl or $C_a$-$C_b$haloalkylsulfonyl that has the meaning mentioned above, respectively. It is selected from the scope of the indicated carbon atom number.

In the specification, the indication of "$C_a$-$C_b$alkoxy ($C_d$-$C_e$)alkyl", "$C_a$-$C_b$alkylthio ($C_d$-$C_e$)alkyl", "$C_a$-$C_b$alkylsulfinyl ($C_d$-$C_e$)alkyl" or "$C_a$-$C_b$alkylsulfonyl($C_d$-$C_e$)alkyl" means the alkyl group having carbon atom number of d to e that has the meaning mentioned above, which a hydrogen atom (hydrogen atoms) bonded to carbon atom is (are) arbitrarily substituted with the $C_a$-$C_b$alkoxy, $C_a$-$C_b$alkylthio, $C_a$-$C_b$alkylsulfinyl or $C_a$-$C_b$alkylsulfonyl that has the meaning mentioned above, respectively. It is selected from the scope of the indicated carbon atom number.

In the specification, the indication of "methyl substituted with $R^{11}$" means methyl group which a hydrogen atom (hydrogen atoms) bonded to carbon atom is (are) arbitrarily substituted with $R^{11}$.

In the specification, the indication of "($C_a$-$C_b$)alkyl arbitrarily substituted with $R^5$" or "($C_a$-$C_b$)alkyl arbitrarily substituted with $R^{11}$" means the alkyl group having carbon atom number of a to b that has the meaning mentioned above, which a hydrogen atom (hydrogen atoms) bonded to carbon atom is (are) arbitrarily substituted with $R^5$ or $R^{11}$. It is selected from the scope of the indicated carbon atom number.

In the specification, the indication of "$C_a$-$C_b$haloalkoxy ($C_d$-$C_e$)haloalkyl" means the haloalkyl having carbon atom number of d to e, which a hydrogen atom (hydrogen atoms) or a halogen atom (halogen atoms) bonded to carbon atom is (are) arbitrarily substituted with the $C_a$-$C_b$haloalkoxy. It is selected from the scope of the indicated carbon atom number.

Some of the substituted benzamide compounds of formula (1) being the active ingredient of the present invention have geometrical isomers of E-form and Z-form depending on the kind of substituents. The present invention includes these E-forms, Z-forms and mixtures containing E-form and Z-form in an arbitrary proportion. In addition, the substituted benzamide compounds of formula (1) of the present invention have optically active forms resulting from the presence of 1 or more asymmetric carbon atoms, and the present invention includes all optically active forms or racemates.

Among the substituted benzamide compounds of formula (1) being the active ingredient of the present invention, the compounds that can be converted to acid addition salts according to a conventional method can be used as for example salts of hydrohalic acid such as hydrofluoric acid, hydrochloric acid, hydrobromic acid, hydroiodic acid or the like, salts of inorganic acids such as nitric acid, sulfuric acid, phosphoric acid, chloric acid, perchloric acid or the like, salts of sulfonic acid such as methansulfonic acid, ethansulfonic acid, trifluoromethansulfonic acid, benzene sulfonic acid, p-toluene sulfonic acid or the like, salts of carboxylic acid such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid, citric acid or the like, or salts of amino acid such as glutamic acid, aspartic acid or the like.

Among the substituted benzamide compounds of formula (1) being the active ingredient of the present invention, the compounds that can be converted to metal salts according to a conventional method can be used as for example salts of alkali metal such as lithium, sodium, potassium, salts of alkaline earth metal such as calcium, barium, magnesium, or metal salts of alminum, zinc, copper and the like.

In the substituted benzamide compound of formula (1) being the active ingredient of the present invention, the atoms of $A^1$ include for example the following groups. That is, $A^1$-I: $A^1$ is C—$X^3$.
$A^1$-II: $A^1$ is nitrogen atom.
Among them, the atoms of $A^1$ are more preferably A-I.

In the substituted benzamide compound of formula (1) being the active ingredient of the present invention, the combination of the atoms of $A^2$, $A^3$ and $A^4$ includes for example the following groups.

That is, A-I: $A^2$, $A^3$ and $A^4$ are C—H.
A-II: $A^2$ and $A^3$ are C—H, $A^4$ is nitrogen atom.
A-III: $A^2$ is C—H, $A^3$ and $A^4$ are C—$Y^2$.
A-IV: $A^2$ and $A^4$ are C—H, $A^3$ is nitrogen atom.
A-V: $A^2$ is nitrogen atom, $A^3$ and $A^4$ are C—H.
A-VI: $A^2$ and $A^3$ are C—H, $A^4$ is C—$Y^2$.
A-VII: $A^2$ and $A^4$ are C—H, $A^3$ is C—$Y^2$.
A-VIII: $A^2$ is C—$Y^2$, $A^3$ and $A^4$ is C—H.
A-IX: $A^2$ and $A^3$ are nitrogen atom, $A^4$ is C—H.
A-X: $A^2$ and $A^4$ are nitrogen atom, $A^3$ is C—H.
A-XI: $A^2$ is C—H, $A^3$ and $A^4$ are nitrogen atom.
Among them, the combination of the atoms of $A^2$, $A^3$ and $A^4$ is preferably A-I to A-V, more preferably A-I to A-III, and further A-I is particularly preferable.

In the substituted benzamide compound of formula (1) being the active ingredient of the present invention, the atoms of W include oxygen atom or sulfur atom.

In the substituted benzamide compound of formula (1) being the active ingredient of the present invention, the heterocyclic ring of G includes for example the following groups.

That is, G-I: G-1.
G-II: G-2 [in which $R^{1a}$ and $R^{1b}$ are hydrogen atom].
G-III: G-2 [in which $R^{1a}$ is fluorine atom, chlorine atom or bromine atom, $R^{1b}$ is hydrogen atom].
G-IV: G-2 [in which $R^{1a}$ is halogen atom, methyl, methylthiomethyl, methylsulfinylmethyl or methylsulfonylmethyl, $R^{1b}$ is hydrogen atom].
G-V: G-2 [in which $R^{1a}$ is $C_1$-$C_3$alkyl, $C_1$-$C_3$alkylthiomethyl, $C_1$-$C_3$haloalkylthiomethyl, $C_1$-$C_3$alkylsulfinylmethyl, $C_1$-$C_3$haloalkylsulfinylmethyl, $C_1$-$C_3$alkylsulfonylmethyl, $C_1$-$C_3$haloalkylsulfonylmethyl, —OH, $C_1$-$C_3$alkylthio or $C_1$-$C_3$alkylsulfonyl, $R^{1b}$ is hydrogen atom].
G-VI: G-2 [in which $R^{1a}$ and $R^{1b}$ together form $C_2$-$C_3$alkylidene].
G-VII: G-2 [in which $R^{1a}$ and $R^{1b}$ together form $C_1$-$C_4$alkylidene, phenylmethylidene, hydroxyimino or $C_1$-$C_3$alkoxyimino].

G-VIII: G-3 [in which $R^{1c}$ is methyl].
G-IX: G-3 [in which $R^{1c}$ is $C_1$-$C_3$alkyl].
G-X: G-4.
G-XI: G-5.
G-XII: G-6.
G-XIII: G-7 [in which $R^{1c}$ is methyl].
G-XIV: G-7 [in which $R^{1c}$ is $C_1$-$C_3$alkyl].
In the meantime, G-1 to G-7 are the heterocyclic rings of the following structural formula, respectively.

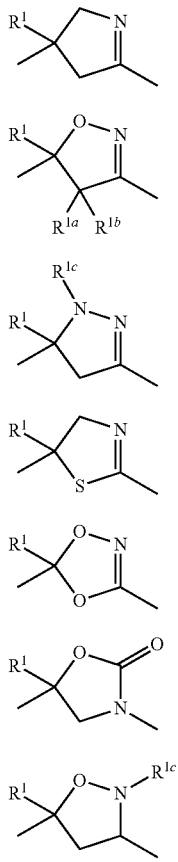

Among them, the heterocyclic rings of G are preferably G-I, G-II, G-III, G-IV, G-VI, G-VIII, G-XII and G-XIII, more preferably G-I, G-II and G-III, and further G-I and G-II are particularly preferable.

In the substituted benzamide compound of formula (1) being the active ingredient of the present invention, when $A^1$ is C—$X^3$, the combination of the substituents of $X^1$, $X^2$ and $X^3$ includes for example the following groups.

That is, X-I: $X^1$ is bromine atom, $X^2$ is chlorine atom, and $X^3$ is hydrogen atom.
X-1: $X^1$ and $X^2$ are bromine atom, and $X^3$ is hydrogen atom.
X-III: $X^1$ is trifluoromethyl, $X^2$ is chlorine atom, and $X^3$ is hydrogen atom.
X-IV: $X^1$ is trifluoromethyl, $X^2$ is bromine atom, and $X^3$ is hydrogen atom.
X-V: both $X^1$ and $X^2$ are chlorine atom or trifluoromethyl, and $X^3$ is hydrogen atom.
X-VI: $X^1$ and $X^2$ are chlorine atom, and $X^3$ is fluorine atom.
X-VII: $X^1$ and $X^2$ are bromine atom, and $X^3$ is fluorine atom.
X-VIII: $X^1$ is iodine atom or trifluoromethyl, and $X^2$ and $X^3$ are hydrogen atom.
X-IX: $X^1$ is chlorine atom, bromine atom or trifluoromethyl, $X^2$ is hydrogen atom, and $X^3$ is fluorine atom or chlorine atom.
X-X: $X^1$ is chlorine atom, bromine atom or trifluoromethyl, $X^2$ is fluorine atom, and $X^3$ is hydrogen atom.
X-X¹: $X^1$ is iodine atom, $X^2$ is chlorine atom, and $X^3$ is hydrogen atom.
X-XII: $X^1$ is trifluoromethyl, $X^2$ is iodine atom, and $X^3$ is hydrogen atom.
X-XIII: $X^1$ and $X^2$ are chlorine atom or bromine atom, and $X^3$ is chlorine atom.
X-XIV: $X^1$ is trifluoromethyl, $X^2$ is fluorine atom, chlorine atom or bromine atom, and $X^3$ is fluorine atom or chlorine atom.
X-XV: $X^1$ is chlorine atom, bromine atom, pentafluoroethyl, trifluoromethoxy, —$SF_5$ or trifluoromethylthio, and $X^2$ and $X^3$ are hydrogen atom.
X-XVI: $X^1$ is chlorine atom, bromine atom, iodine atom or trifluoromethyl, $X^2$ is hydrogen atom, and $X^3$ is fluorine atom, chlorine atom or bromine atom.
X-XVII: $X^1$ is iodine atom or trifluoromethyl, $X^2$ is fluorine atom or cyano, and $X^3$ is hydrogen atom.
X-XVIII: $X^1$ is chlorine atom, bromine atom or trifluoromethyl, $X^2$ is methyl, methoxy, difluoromethoxy, trifluoromethoxy, difluoromethylthio or trifluoromethylthio, and $X^3$ is hydrogen atom.
X-XIX: $X^1$ is fluorine atom, chlorine atom or bromine atom, $X^2$ is fluorine atom, chlorine atom, bromine atom or methyl, and $X^3$ is fluorine atom, chlorine atom or difluoromethoxy.
X-XX: both $X^1$ and $X^2$ are chlorine atom, bromine atom or trifluoromethyl, and $X^3$ is chlorine atom, bromine atom or cyano.
X-XXI: $X^1$ and $X^2$ are hydrogen atom, and $X^3$ is halogen atom.
X-XXII: $X^1$ is fluorine atom, $C_1$-$C_3$haloalkyl, halocyclopropyl, —$OR^4$ [in which $R^4$ is $C_1$-$C_3$haloalkyl or $C_1$-$C_2$haloalkoxy ($C_1$-$C_2$)haloalkyl] or $C_1$-$C_3$haloalkylthio, and $X^2$ and $X^3$ are hydrogen atom.
X-XXIII: $X^1$ is halogen atom, methyl or trifluoromethyl, $X^2$ is hydrogen atom, and $X^3$ is halogen atom.
X-XXIV: $X^1$ is halogen atom or trifluoromethyl, $X^2$ is fluorine atom, iodine atom, cyano, nitro, methylthio or —$NH_2$, and $X^3$ is halogen atom.
X-XXV: $X^1$ is chlorine atom, bromine atom or trifluoromethyl, $X^2$ is $C_1$-$C_3$alkyl, $C_1$-$C_3$haloalkyl, —$OR^4$ or —S(O)$_p R^4$ [in which $R^4$ is $C_1$-$C_3$alkyl or $C_1$-$C_3$haloalkyl, and p is an integer of 0 to 2] and $X^3$ is hydrogen atom.
X-XXVI: $X^1$ is halogen atom or trifluoromethyl, $X^2$ is halogen atom, methyl or trifluoromethyl, and $X^3$ is halogen atom.
X-XXVII: $X^1$ and $X^2$ are independently of each other chlorine atom, bromine atom or trifluoromethyl, and $X^3$ is cyano, methyl, methoxy, difluoromethoxy, methylthio, —$NH_2$ or dimethylamino.
X-XXVIII: $X^1$ together with $X^3$ forms 5- or 6-membered ring together with the carbon atoms to which each of $X^1$ and $X^3$ is bonded by forming —$CF_2OCF_2$—, —$OCF_2O$—, —$CF_2OCF_2O$— or —$OCF_2CF_2O$—, and $X^2$ is hydrogen atom.

Among them, the combination of the substituents of $X^1$, $X^2$ and $X^3$ is preferably X-I to X-XX, more preferably X-I to X-XIV, and further X-I to X-VII are particularly preferable.

In the substituted benzamide compound of formula (1) being the active ingredient of the present invention, when $A^1$ is nitrogen atom, the combination of the substituents of $X^1$ and $X^2$ includes for example the following groups.

X-XXIX: both $X^1$ and $X^2$ is chlorine atom or trifluoromethyl.

X-XXX: $X^1$ is trifluoromethyl, and $X^2$ is hydrogen atom or chlorine atom.

X-XXXI: $X^1$ is chlorine atom or pentafluoroethyl, and $X^2$ is hydrogen atom.

X-XXXII: $X^1$ is bromine atom, and $X^2$ is hydrogen atom.

X-XXXIII: both $X^1$ and $X^2$ is fluorine atom or bromine atom.

X-XXXIV: $X^1$ is trifluoromethyl, and $X^2$ is bromine atom.

Among them, the combination of the substituents of $X^1$ and $X^2$ is preferably X-XXIX to X-XXXI, more preferably X-XXIX to X-XXX, and further X-XXIX is particularly preferable.

In the substituted benzamide compound of formula (1) being the active ingredient of the present invention, the substituent of $Y^1$ includes for example the following groups. That is, $Y^1$-I: chlorine atom and bromine atom.

$Y^1$-II: methyl.

$Y^1$-III: fluorine atom and iodine atom.

$Y^1$-IV: nitro.

$Y^1$-V: ethyl and trifluoromethyl.

$Y^1$-VI: hydrogen atom.

$Y^1$-VII: methoxymethyl.

$Y^1$-VIII: —N($R^7$)$R^6$ [in which $R^6$ is hydrogen atom, methyl or acetyl, $R^7$ is hydrogen atom or methyl].

$Y^1$-IX: cyclopropyl and ethynyl.

$Y^1$-X: cyano and —C(S)NH$_2$.

$Y^1$-XI: difluoromethoxy and methylthio.

$Y^1$-XII: —N($R^7$)$R^6$ [in which $R^6$ is $C_1$-$C_3$alkylcarbonyl or cyclopropylcarbonyl, $R^7$ is hydrogen atom or methyl].

$Y^1$-XIII: hydroxymethyl, methylthiomethyl, methoxy, trifluoromethoxy, difluoromethylthio, trifluoromethylthio and trimethylsilylethynyl.

$Y^1$-XIV: —N($R^7$)$R^6$ [in which $R^6$ is —CHO or methoxycarbonyl, $R^7$ is hydrogen atom or methyl].

$Y^1$-XV: phenyl, D-1, D-2, D-3 and D-19 [in which n2, n3 and n4 are 0].

$Y^1$-XVI: $C_1$-$C_3$alkyl, $C_1$-$C_3$haloalkyl, ($C_1$-$C_2$)alkyl substituted with $R^5$ [in which $R^5$ is —OH, $C_1$-$C_3$alkoxy, $C_1$-$C_3$haloalkoxy, $C_1$-$C_3$alkylthio or $C_1$-$C_3$haloalkylthio], $C_3$-$C_4$cycloalkyl, $C_2$-$C_3$alkynyl and trimethylsilylethynyl.

$Y^1$-XVII: $C_1$-$C_3$alkoxy, $C_1$-$C_3$haloalkoxy, $C_1$-$C_3$alkylthio and $C_1$-$C_3$haloalkylthio.

$Y^1$-XVIII: —N($R^7$)$R^6$ [in which $R^6$ is $C_1$-$C_4$alkyl, $R^7$ is hydrogen atom or $C_1$-$C_3$alkyl].

$Y^1$-XIX: —N($R^7$)$R^6$ [in which $R^6$ is —CHO, $C_1$-$C_3$alkylcarbonyl, $C_1$-$C_3$haloalkylcarbonyl, $C_3$-$C_4$cycloalkylcarbonyl, $C_1$-$C_3$alkoxycarbonyl, $C_1$-$C_3$alkylthiocarbonyl, $C_1$-$C_3$alkoxythiocarbonyl, $C_1$-$C_3$alkyldithiocarbonyl, $C_1$-$C_3$alkylsulfonyl or $C_1$-$C_3$haloalkylsulfonyl, $R^7$ is hydrogen atom or $C_1$-$C_3$alkyl].

$Y^1$-XX: phenyl substituted with $(Z)_{n1}$ [in which Z is halogen atom, cyano, nitro, methyl, trifluoromethyl, methoxy, methylthio, methylsulfinyl, methylsulfonyl, —NH$_2$ or dimethylamino, n1 is an integer of 1 to 5] and D [in which D is an aromatic heterocyclic ring of following structural formulae D-1 to D-3, D-7, D-11 and D-19 to D-23:

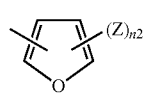
D-1

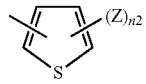
D-2

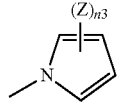
D-3

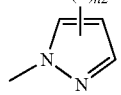
D-7

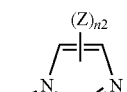
D-11

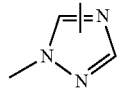
D-19

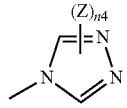
D-20

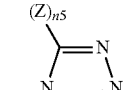
D-21

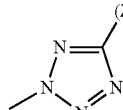
D-22

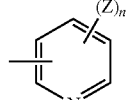
D-23

Z is halogen atom or methyl, n2 is an integer of 0 to 3, n3 is an integer of 0 to 4, n4 is an integer of 0 to 2, n5 is an integer of 0 or 1 and q is 0].

Among them, the substituent of $Y^1$ is preferably $Y^1$-I to $Y^1$-XII, more preferably $Y^1$-I to $Y^1$-V, and further $Y^1$-I and $Y^1$-II are particularly preferable.

In the substituted benzamide compound of formula (1) being the active ingredient of the present invention, the substituent of $Y^2$ includes for example the following groups. That is, $Y^2$-I: hydrogen atom.

$Y^2$-II: adjacent two $Y^2$s form 6-membered ring together with carbon atoms to which each of the adjacent two $Y^2$s is bonded by forming —CH═CHCH═CH—.

$Y^2$-III: fluorine atom.

$Y^2$-IV: adjacent two $Y^2$s form 5-membered ring together with carbon atoms to which each of the adjacent two $Y^2$s is bonded by forming ═NSN═.

$Y^2$-V: chlorine atom and methyl.

Y²-VI: bromine atom and iodine atom.

Y²-VII: adjacent two Y²s form 6-membered ring together with carbon atoms to which each of the adjacent two Y²s is bonded by forming —CH=CHCH=CH— [in this case, hydrogen atoms bonded to each carbon atom forming the ring may be arbitrarily substituted with Z, further when it is substituted with two or more Zs, each Z may be identical with or different from each other, Z is halogen atom].

Among them, the substituent of Y² is more preferably Y²-I and Y²-II, and further Y²-I is particularly preferable.

In the substituted benzamide compound of formula (1) being the active ingredient of the present invention, the substituent of R¹ includes for example the following groups.

That is, R¹-I: trifluoromethyl.

R¹-II: chlorodifluoromethyl.

R¹-III: difluoromethyl.

R¹-IV: pentafluoroethyl.

R¹-V: $C_1$-$C_3$haloalkyl.

R¹-VI: halocyclopropyl.

Among them, the substituent of R¹ is preferably R¹-I to R¹-III, more preferably R¹-I and R¹-II, and further R¹-I is particularly preferable.

In the substituted benzamide compound of formula (1) being the active ingredient of the present invention, the substituent of R² includes for example the following groups.

That is, R²-I: E-3a [in which p is an integer of 0 to 2].

R²-II: E-3b [in which R¹ is methyl, and p is an integer of 0 to 2].

R²-III: E-6 [in which R¹⁰ is $C_1$-$C_3$alkyl or $C_2$-$C_3$haloalkyl].

R²-IV: —CH₂-(E-1a) [in which p is an integer of 0 to 2].

R²-V: E-3c [in which R⁸ is methyl, and p is an integer of 0 to 2].

R²-VI: E-3d [in which R⁵ is methyl, and p is 0].

R²-VII: E-4-a [in which R⁹ is hydrogen atom, and q is 1].

R²-VIII: E-5 [in which R¹⁰ is $C_1$-$C_3$alkyl or $C_2$-$C_3$haloalkyl].

R²-IX: E-6 [in which R¹⁰ is $C_1$-$C_4$alkyl, $C_1$-$C_4$haloalkyl, $C_1$-$C_3$alkoxy ($C_1$-$C_2$)alkyl, oxetan-3-yl or $C_3$-$C_4$alkynyl].

R²-X: —CH₂-(E-9) [in which R¹⁰ is $C_1$-$C_3$alkyl or $C_2$-$C_3$haloalkyl].

R²-XI: ($C_1$-$C_3$)alkyl substituted with E [in which E is E-1a or E-2a, R⁹ is hydrogen atom, cyano or $C_1$-$C_2$haloalkylcarbonyl, p is an integer of 0 to 2, and q is an integer of 0 or 1].

R²-XII: E-3b, E-3c, E-3d, E-4-a, E-4-b, E-4-c and E-4-d [in which R¹ is $C_1$-$C_3$alkyl, R⁹ is hydrogen atom, cyano or $C_1$-$C_2$haloalkylcarbonyl, p is an integer of 0 to 2, and q is an integer of 0 or 1].

R²-XIII: E-4-b [in which R⁸ is $C_1$-$C_3$alkyl, R⁹ is hydrogen atom, and q is 1].

R²-XIV: E-5 and E-6 [in which R¹⁰ is hydrogen atom, $C_1$-$C_4$alkyl, $C_1$-$C_4$haloalkyl, hydroxy ($C_1$-$C_2$)alkyl, $C_1$-$C_3$alkoxy ($C_1$-$C_2$)alkyl, benzyl, $C_3$-$C_4$cycloalkyl, oxetan-3-yl, thietan-3-yl, $C_3$-$C_4$alkynyl or $C_3$-$C_4$alkenyl,].

R²-XV: ($C_1$-$C_3$)alkyl substituted with E [in which E is E-7, E-8, E-9 or E-10, R¹⁰ is $C_1$-$C_4$alkyl, $C_1$-$C_4$haloalkyl, benzyl, phenyl or phenyl substituted with $(Z)_{n1}$, Z is halogen atom, cyano, nitro, methyl, trifluoromethyl, methoxy, methylthio, methylsulfinyl or methylsulfonyl, when n1 is an integer of 2 or more, each Z may be identical with or different from each other, n1 is an integer of 1 to 5].

R²-XVI: E-11, E-12 and ($C_1$-$C_3$)alkyl substituted with E-13.

In the meantime, E-1a to E-13 are the heterocyclic ring of following structural formulae, respectively:

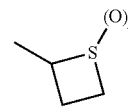 E-1a

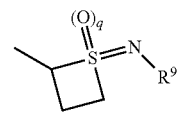 E-2a

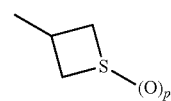 E-3a

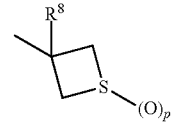 E-3b

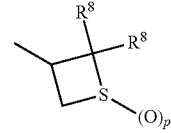 E-3c

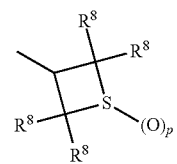 E-3d

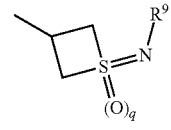 E-4a

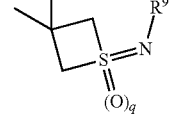 E-4b

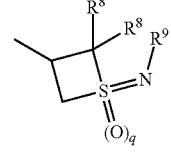 E-4c

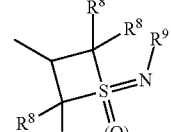 E-4d

E-5

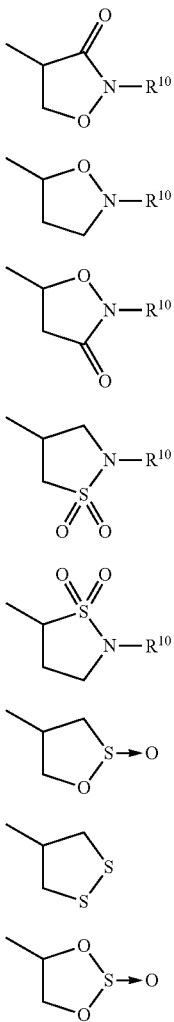

E-6

E-7

E-8

E-9

E-10

E-11

E-12

E-13

Among them, the substituent of $R^2$ is preferably $R^2$-I to $R^2$-X, more preferably $R^2$-I to $R^2$-III, and further $R^2$-I is particularly preferable.

In the substituted benzamide compound of formula (1) being the active ingredient of the present invention, the substituent of $R^3$ includes for example the following groups. That is, $R^3$-I: hydrogen atom.

$R^3$-II: ethyl, cyanomethyl, methoxymethyl and propargyl.

$R^3$-III: —C(O)R$^{12}$ [in which R$^{12}$ is $C_1$-$C_4$alkyl or cyclopropyl].

$R^3$-IV: methoxycarbonyl.

$R^3$-V: $C_1$-$C_3$alkyl, methyl substituted with R$^{11}$ [in which R$^{11}$ is ethoxy or —C(S)NH$_2$], cyclopropyl and allyl.

$R^3$-VI: —C(O)R$^{12}$ [in which R$^{12}$ is $C_1$-$C_3$alkoxy ($C_1$-$C_2$)alkyl, $C_3$-$C_4$cyclolakyl, $C_2$-$C_4$alkenyl or $C_2$-$C_4$alkynyl].

$R^3$-VII: —C(O)OR$^{13}$ [in which R$^{13}$ is $C_1$-$C_4$alkyl, $C_1$-$C_4$haloalkyl, $C_1$-$C_3$alkoxy ($C_1$-$C_2$)alkyl, $C_3$-$C_4$alkenyl or $C_3$-$C_4$alkynyl].

$R^3$-VIII: $C_1$-$C_4$alkyl, ($C_1$-$C_2$)alkyl substituted with R$^{11}$ [in which R$^{11}$ is $C_3$-$C_4$cycloalkyl, phenyl or D-23, n3 is 0 and q is 0], $C_3$-$C_4$cycloalkyl, $C_3$-$C_4$alkenyl and $C_3$-$C_4$alkynyl.

$R^3$-IX: ($C_1$-$C_2$)alkyl substituted with R$^{11}$ [in which R$^{11}$ is cyano, $C_1$-$C_3$alkoxycarbonyl, —C(O)NH$_2$ or —C(S)NH$_2$].

$R^3$-X: ($C_1$-$C_2$)alkyl substituted with R$^{11}$ [in which R$^{11}$ is —OR$^{14}$, R$^{14}$ is hydrogen atom, $C_1$-$C_4$alkyl, $C_1$-$C_4$haloalkyl, $C_3$-$C_4$alkenyl, $C_3$-$C_4$alkynyl, $C_1$-$C_4$alkylcarbonyl, $C_1$-$C_4$haloalkylcarbonyl, $C_3$-$C_6$cycloalkylcarbonyl or $C_1$-$C_4$alkoxycarbonyl].

$R^3$-XI: ($C_1$-$C_2$)alkyl substituted with R$^{11}$ [in which R$^{11}$ is $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl or $C_1$-$C_3$haloalkylsulfonyl].

$R^3$-XII: —C(O)R$^{12}$ [in which R$^{12}$ is hydrogen atom, $C_1$-$C_4$haloalkyl, $C_1$-$C_3$alkylthio ($C_1$-$C_2$)alkyl, $C_1$-$C_3$alkylsulfinyl ($C_1$-$C_2$)alkyl, $C_1$-$C_3$alkylsulfonyl ($C_1$-$C_2$)alkyl or $C_3$-$C_6$cycloalkyl].

$R^3$-XIII: —C(O)R$^{12}$ [in which R$^{12}$ is phenyl or phenyl substituted with (Z)$_{n1}$, D-1, D-2 or D-23, Z is halogen atom, cyano, nitro, methyl, trifluoromethyl, methoxy, methylthio, methylsulfinyl or methylsulfonyl, when n1, n2 or n3 is an integer of 2 or more, each Z may be identical with or different from each other, n1 is an integer of 1 to 5, n2 is an integer of 0 to 3, n3 is an integer of 0 to 4, and q is an integer of 0 or 1].

$R^3$-XIV: —C(O)OR$^{13}$ [in which R$^{13}$ is phenyl] and —C(O)C(O)OR$^{13}$ [in which R$^{13}$ is $C_1$-$C_4$alkyl].

$R^3$-XV: $C_1$-$C_3$haloalkylthio.

In the meantime, D-1, D-2 and D-23 are an aromatic heterocyclic ring of following structural formulae, respectively:

D-1

D-2

D-23

Among them, the substituent of $R^3$ is preferably $R^3$-I to $R^3$-VII, more preferably $R^1$-I to $R^3$-IV, and further $R^3$-I is particularly preferable.

Each group showing the combination of each substituent and the scope of each substituent in the above-mentioned substituted benzamide compound of formula (1) being the active ingredient of the present invention can be arbitrarily combined one another, and all combination thereof shows preferable scope of the substituted benzamide compound of formula (1) that is the active ingredient of the parasite- and hygienic-controlling composition of the present invention.

Some of the substituted benzamide compounds of formula (1) being the active ingredient of the present invention are compounds known from WO 2009/080250, WO 2010/020522, WO 2010/149506, WO 2011/067272 or the like, and the compounds other than the above-mentioned known compounds can be also produced for example according to the synthesis methods mentioned in the above-mentioned patent documents and JP-A 2007-308471, JP-A 2008-239611, JP-A 2010-168367, JP-A 2010-235590, WO 2009/072621, WO 2010/027051 or the like.

The substituted benzamide compounds of formula (1) being the active ingredient of the present invention that can be produced by use of these methods concretely include for example the compounds shown in Tables 1 to 3. As the compounds shown in Tables 1 to 3 are only for purposes of illustration, the present invention is not limited thereto.

In the meantime, in Tables, the indication "Et" means ethyl, hereinafter similarly thereto, "n-Pr" and "Pr-n" mean normal propyl, "i-Pr" and "Pr-i" mean isopropyl, "c-Pr" and "Pr-c" mean cyclopropyl, "n-Bu" and "Bu-n" mean normal butyl, "c-Bu" and "Bu-c" mean cyclobutyl, and "t-Bu" and "Bu-t" mean tertiary butyl, and in Tables, the substituents indicated as "E-1a-1" to "E-1a-3", "E-2a-1", "E-3a-1" to "E-3a-3", "E-3b-1" to "E-3b-3", "E-3c-1" to "E-3c-3", "E-3d-1", "E-4-a-1", "E-4-b-1", "E-5", "E-6" and "E-9" are heterocyclic rings of the following structural formulae, respectively:

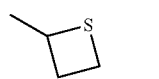
E-1a-1

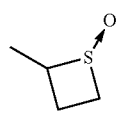
E-1a-2

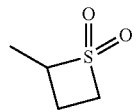
E-1a-3

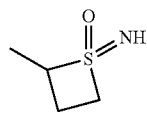
E-2a-1

E-3a-1

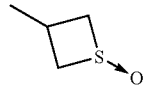
E-3a-2

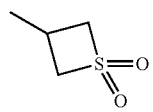
E-3a-3

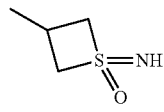
E-4a-1

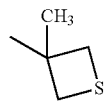
E-3b-1

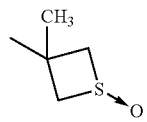
E-3b-2

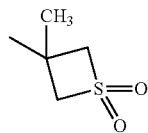
E-3b-3

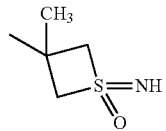
E-4b-1

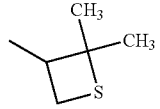
E-3c-1

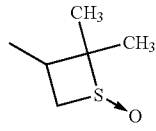
E-3c-2

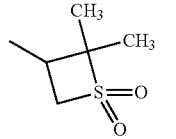
E-3c-3

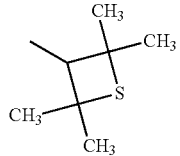
E-3d-1

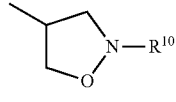
E-5

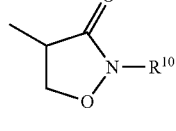
E-6

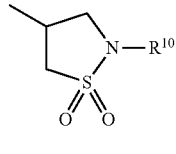
E-9

For example, the indication "[CH$_2$(E-9)Et]" means 2-ethyl-1,1-dioxoisothiazolidin-4-ylmethyl, and further, in Tables, the substituent indicated as "T-1" is the substituent of the following stratural formula:

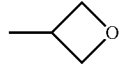
T-1

Table 1 shows the substituted benzamide compounds of formula (1) in which A$^1$ is C—X$^3$.

TABLE 1
[1]-1
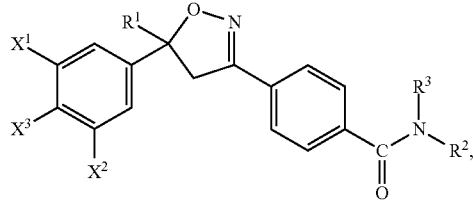
[1]-2
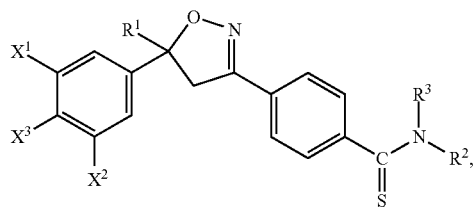
[1]-3
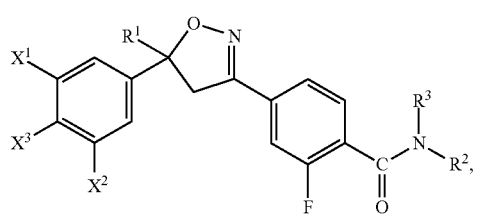
[1]-4
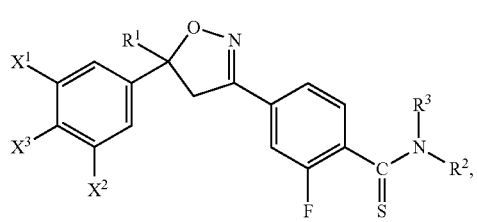
[1]-5
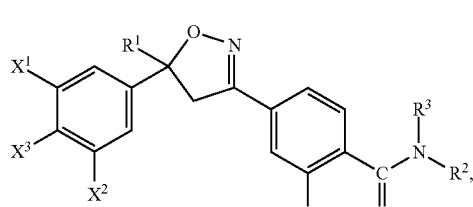
[1]-6
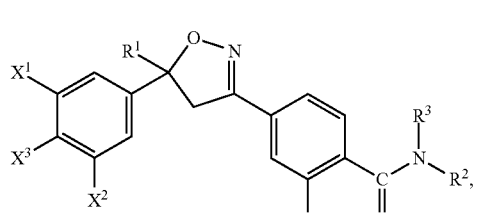
TABLE 1-continued
[1]-7
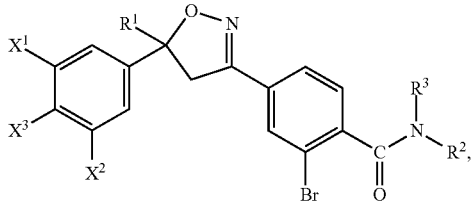
[1]-8
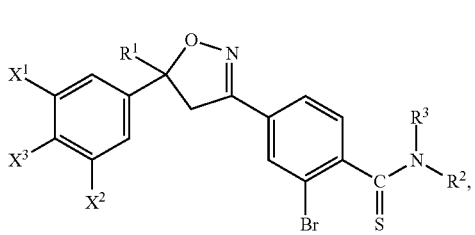
[1]-9
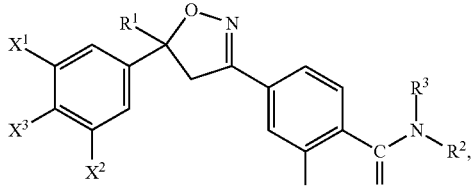
[1]-10
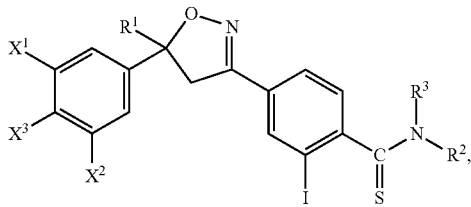
[1]-11
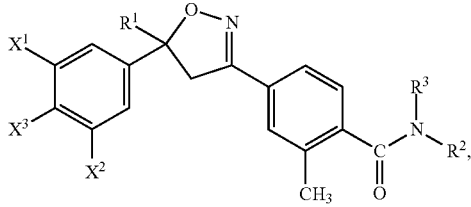
[1]-12
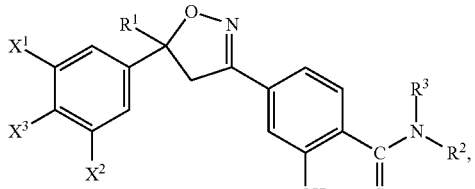

TABLE 1-continued
[1]-13
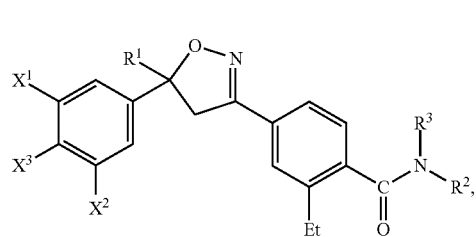
[1]-14
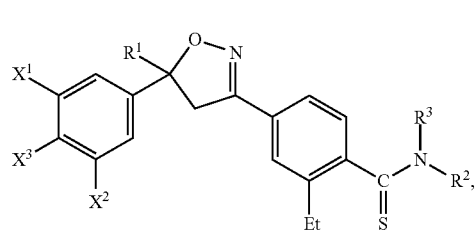
[1]-15
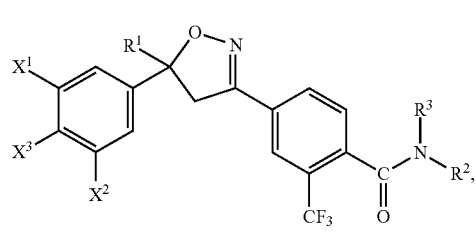
[1]-16
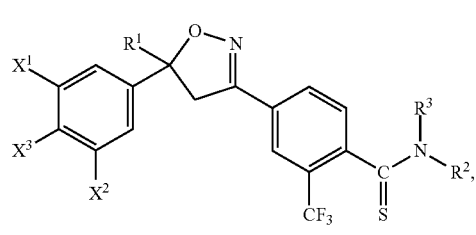
[1]-17
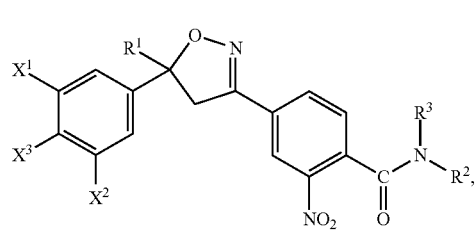
[1]-18
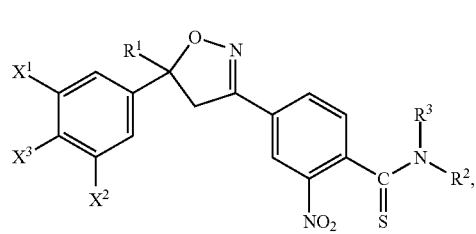
TABLE 1-continued
[1]-19
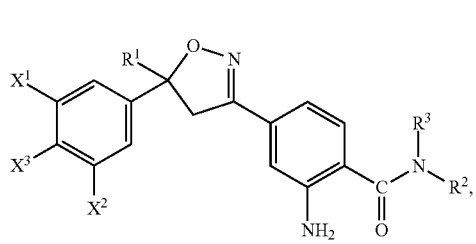
[1]-20
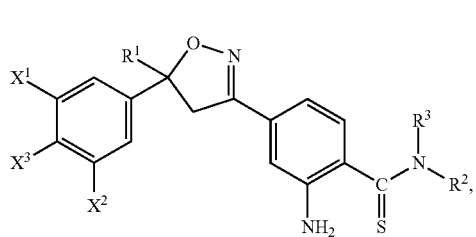
[1]-21
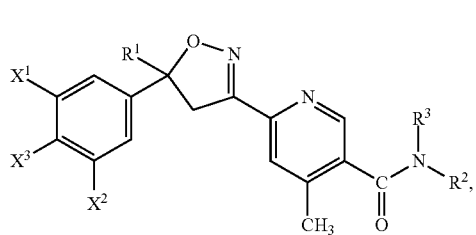
[1]-22
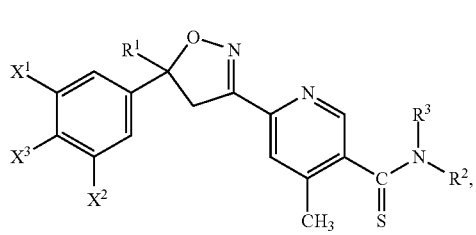
[1]-23
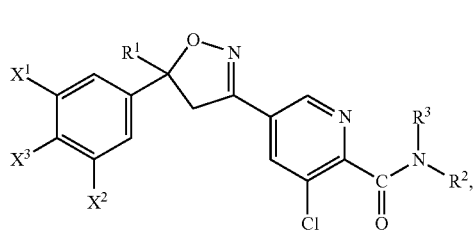
[1]-24
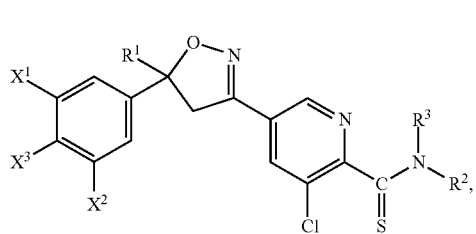

TABLE 1-continued
[1]-25
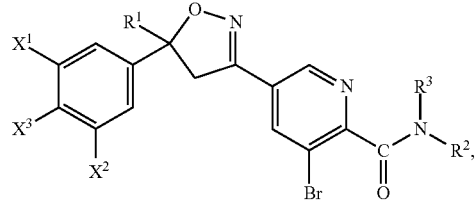
[1]-26
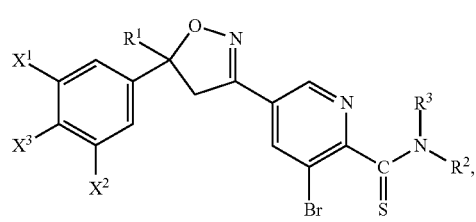
[1]-27
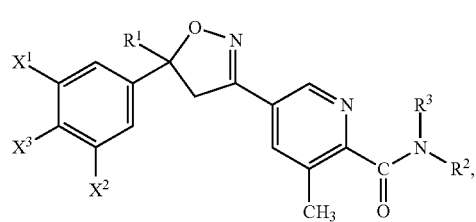
[1]-28
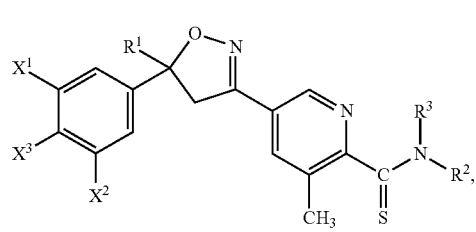
[1]-29
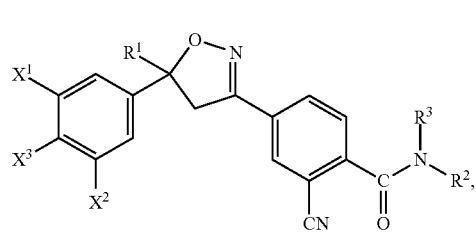
[1]-30
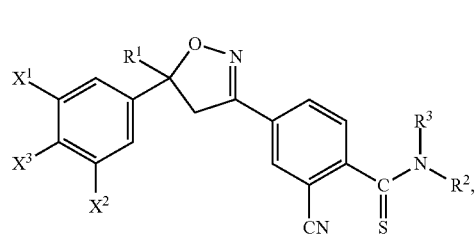
TABLE 1-continued
[1]-31
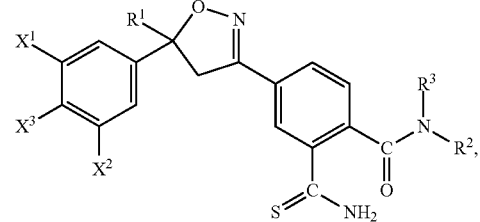
[1]-32
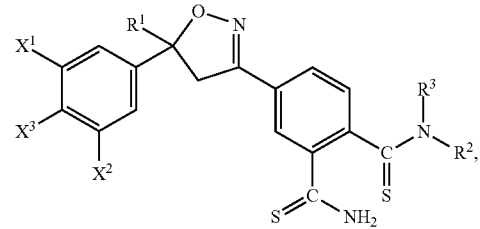
[1]-33
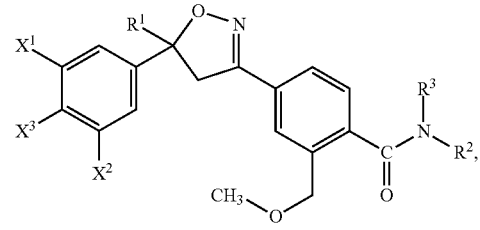
[1]-34
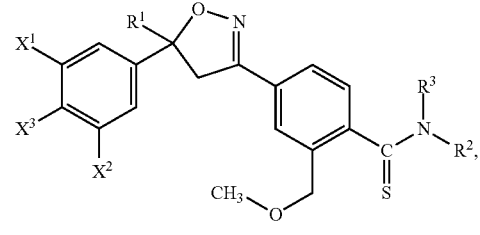
[1]-35
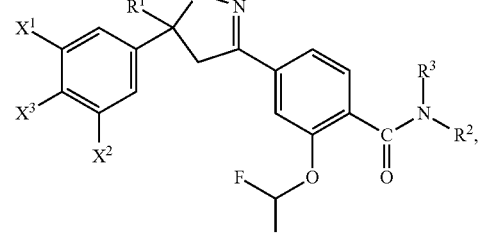
[1]-36
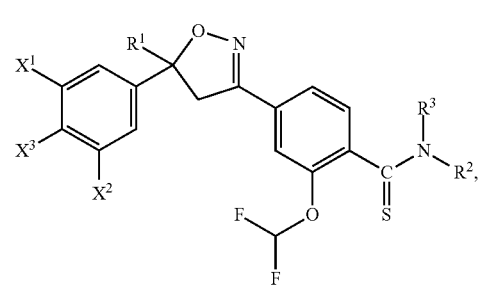

TABLE 1-continued
[1]-37
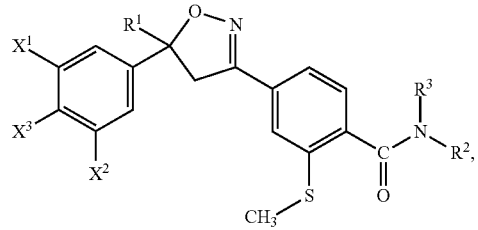
[1]-38
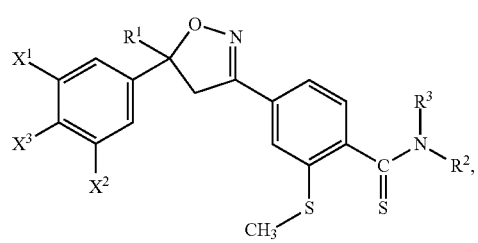
[1]-39
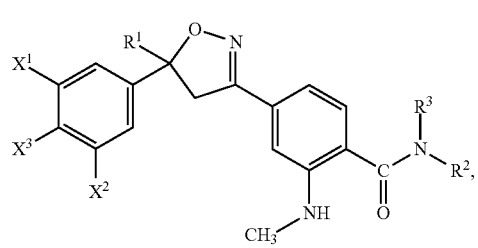
[1]-40
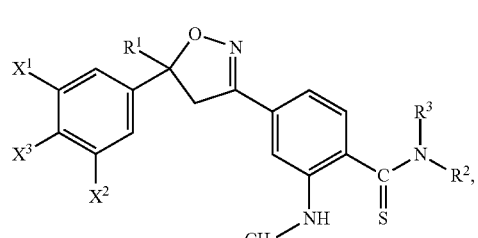
[1]-41
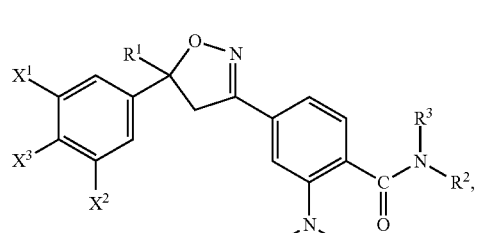
[1]-42
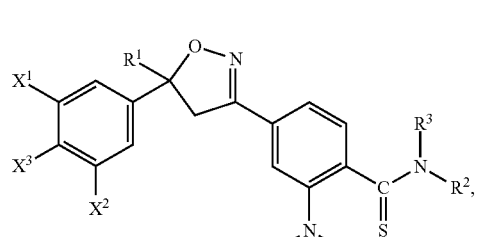
TABLE 1-continued
[1]-43
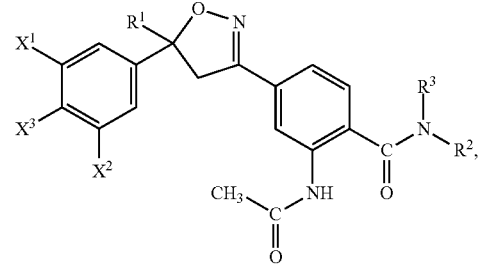
[1]-44
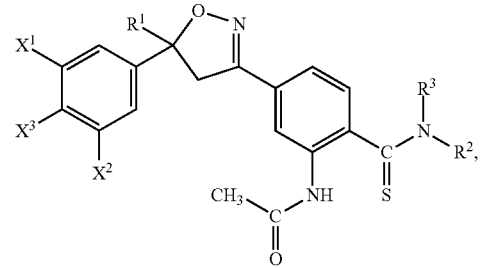
[1]-45
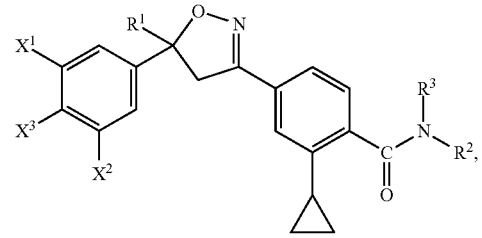
[1]-46
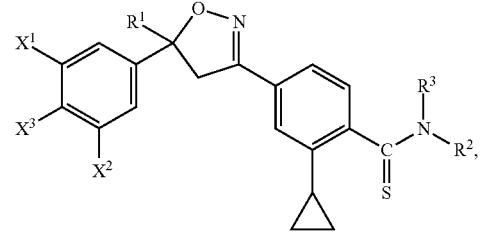
[1]-47
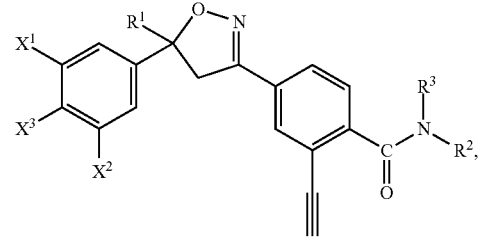
[1]-48

TABLE 1-continued
[1]-49
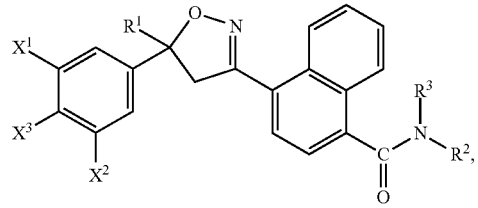
[1]-50
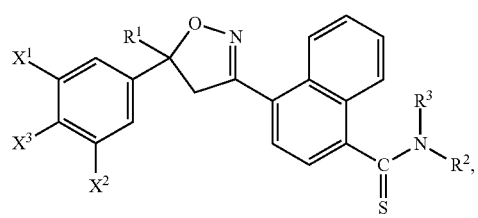
[1]-51
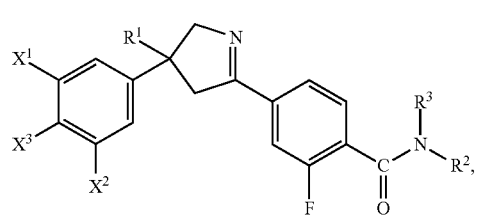
[1]-52
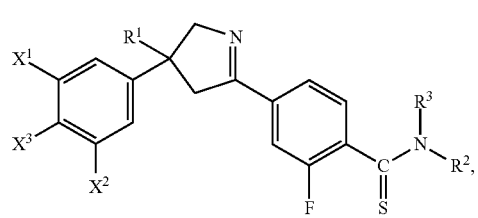
[1]-53
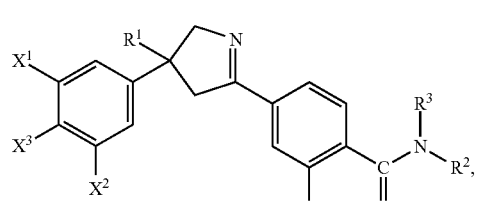
[1]-54
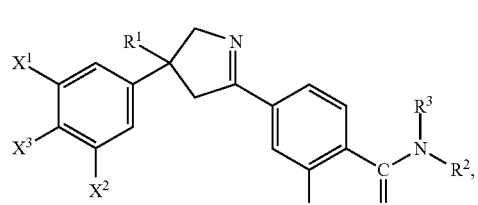
TABLE 1-continued
[1]-55
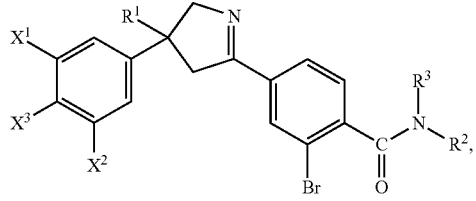
[1]-56
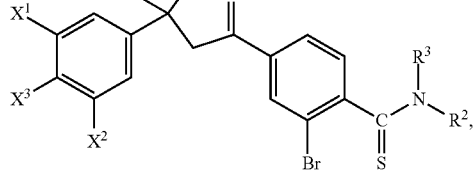
[1]-57
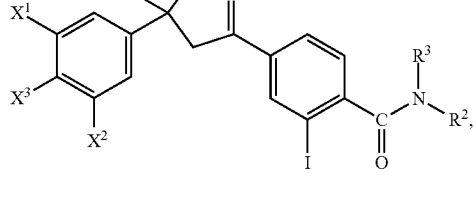
[1]-58
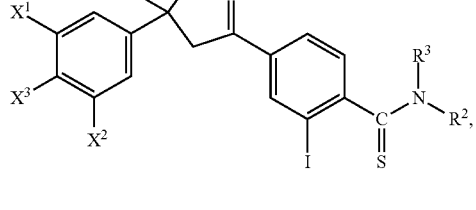
[1]-59
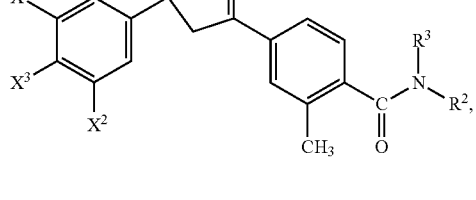
[1]-60
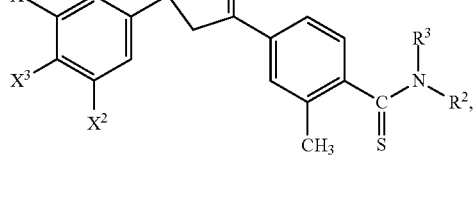
[1]-61

TABLE 1-continued
[1]-62
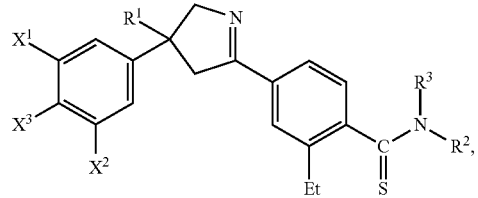
[1]-63
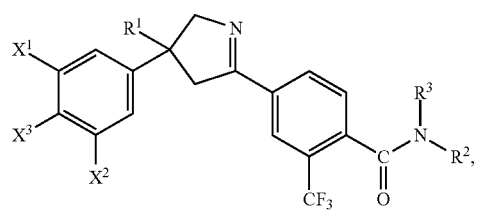
[1]-64
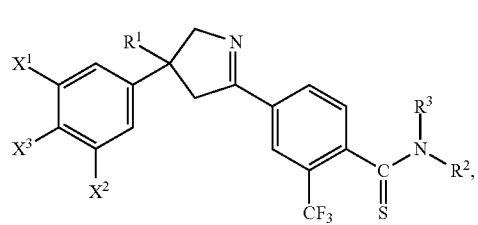
[1]-65
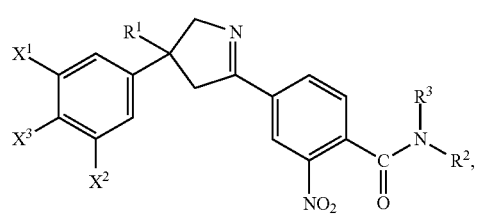
[1]-66
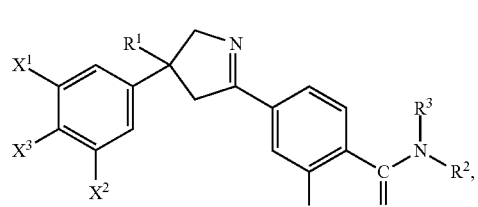
[1]-67
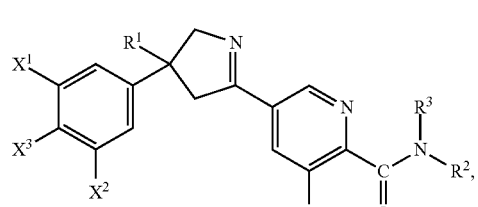
TABLE 1-continued
[1]-68
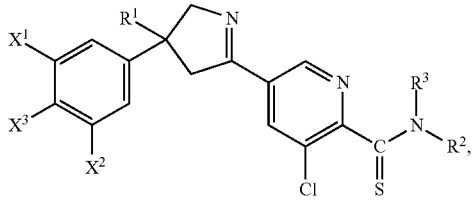
[1]-69
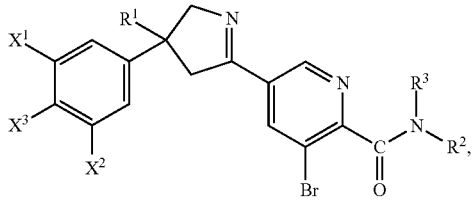
[1]-70
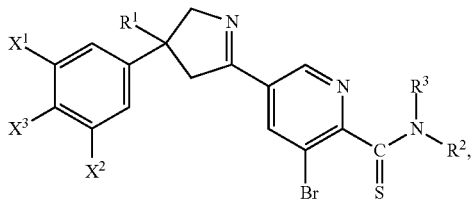
[1]-71
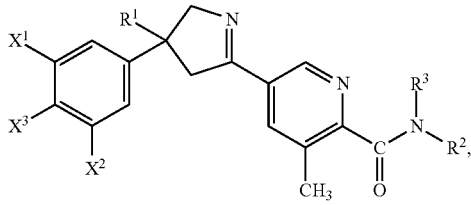
[1]-72
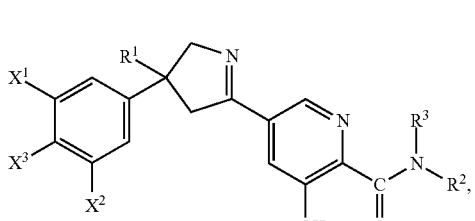
[1]-73
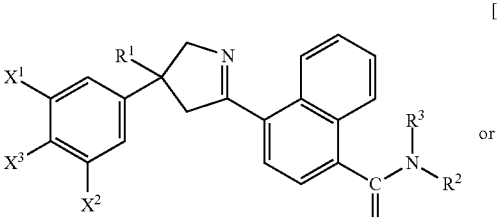
or TABLE 1-continued

[1]-74

| X¹ | X³ | X² | R¹ | R³ | R² |
|---|---|---|---|---|---|
| Cl | H | H | $CF_3$ | H | E-3a-1 |
| Cl | H | H | $CF_3$ | H | E-3a-2 |
| Cl | H | H | $CF_3$ | H | E-3a-3 |
| Br | H | H | $CF_3$ | H | E-3a-1 |
| Br | H | H | $CF_3$ | H | E-3a-2 |
| Br | H | H | $CF_3$ | H | E-3a-3 |
| Br | H | H | $CF_3$ | H | E-3b-1 |
| Br | H | H | $CF_3$ | H | (E-6)Et |
| Br | H | H | $CF_3$ | H | (E-6)$CH_2CF_3$ |
| I | H | H | $CF_3$ | H | E-3a-1 |
| I | H | H | $CF_3$ | H | E-3a-2 |
| I | H | H | $CF_3$ | H | E-3a-3 |
| I | H | H | $CF_3$ | H | E-3b-1 |
| I | H | H | $CF_3$ | H | (E-6)Et |
| I | H | H | $CF_3$ | H | (E-6) $CH_2CHF_2$ |
| I | H | H | $CF_3$ | H | (E-6) $CH_2CF_3$ |
| $CF_3$ | H | H | $CF_3$ | H | E-3a-1 |
| $CF_3$ | H | H | $CF_3$ | H | E-3a-2 |
| $CF_3$ | H | H | $CF_3$ | H | E-3a-3 |
| $CF_3$ | H | H | $CF_3$ | H | E-3b-1 |
| $CF_3$ | H | H | $CF_3$ | H | (E-6) Et |
| $CF_3$ | H | H | $CF_3$ | H | (E-6) $CH_2CHF_2$ |
| $CF_3$ | H | H | $CF_3$ | H | (E-6) $CH_2CF_3$ |
| $CF_2CF_3$ | H | H | $CF_3$ | H | E-3a-1 |
| $CF_2CF_3$ | H | H | $CF_3$ | H | E-3a-2 |
| $CF_2CF_3$ | H | H | $CF_3$ | H | E-3a-3 |
| $OCF_3$ | H | H | $CF_3$ | H | E-3a-1 |
| $OCF_3$ | H | H | $CF_3$ | H | E-3a-2 |
| $OCF_3$ | H | H | $CF_3$ | H | E-3a-3 |
| $OCF_3$ | H | H | $CF_3$ | H | E-3b-1 |
| $OCF_3$ | H | H | $CF_3$ | H | (E-6)Et |
| $OCF_3$ | H | H | $CF_3$ | H | (E-6) $CH_2CF_3$ |
| $OCF_2Br$ | H | H | $CF_3$ | H | E-3a-1 |
| $OCF_2Br$ | H | H | $CF_3$ | H | E-3a-2 |
| $OCF_2Br$ | H | H | $CF_3$ | H | E-3a-3 |
| $SF_5$ | H | H | $CF_3$ | H | E-3a-1 |
| $SF_5$ | H | H | $CF_3$ | H | E-3a-2 |
| $SF_5$ | H | H | $CF_3$ | H | E-3a-3 |
| $SCF_3$ | H | H | $CF_3$ | H | E-3a-1 |
| $SCF_3$ | H | H | $CF_3$ | H | E-3a-2 |
| $SCF_3$ | H | H | $CF_3$ | H | E-3a-3 |
| $SCF_3$ | H | H | $CF_3$ | H | E-3b-1 |
| $SCF_3$ | H | H | $CF_3$ | H | (E-6)Et |
| $SCF_3$ | H | H | $CF_3$ | H | (E-6) $CH_2CF_3$ |
| Cl | F | H | $CF_3$ | H | E-3a-1 |
| Cl | F | H | $CF_3$ | H | E-3a-2 |
| Cl | F | H | $CF_3$ | H | E-3a-3 |
| Cl | F | H | $CF_3$ | H | E-3b-1 |
| Cl | F | H | $CF_3$ | H | (E-6)Et |
| Cl | F | H | $CF_3$ | H | (E-6) $CH_2CHF_2$ |
| Cl | F | H | $CF_3$ | H | (E-6) $CH_2CF_3$ |
| Cl | H | F | $CF_3$ | H | E-3a-1 |
| Cl | H | F | $CF_3$ | H | E-3a-2 |
| Cl | H | F | $CF_3$ | H | E-3a-3 |
| Cl | H | F | $CF_3$ | H | E-3b-1 |
| Cl | H | F | $CF_3$ | H | (E-6)Et |
| Cl | H | F | $CF_3$ | H | (E-6) $CH_2CHF_2$ |
| Cl | H | F | $CF_3$ | H | (E-6) $CH_2CF_3$ |
| Cl | Cl | H | $CF_3$ | H | E-3a-1 |
| Cl | Cl | H | $CF_3$ | H | E-3a-2 |
| Cl | Cl | H | $CF_3$ | H | E-3a-3 |
| Cl | Cl | H | $CF_3$ | H | E-3b-1 |
| Cl | Cl | H | $CF_3$ | H | (E-6)Et |
| Cl | Cl | H | $CF_3$ | H | (E-6) $CH_2CHF_2$ |
| Cl | Cl | H | $CF_3$ | H | (E-6) $CH_2CF_3$ |
| Cl | H | Cl | $CF_3$ | H | $CH_2$(E-1a-1) |
| Cl | H | Cl | $CF_3$ | H | $CH_2$(E-1a-2) |
| Cl | H | Cl | $CF_3$ | H | $CH_2$(E-1a-3) |
| Cl | H | Cl | $CF_3$ | H | $CH_2$(E-2a-1) |
| Cl | H | Cl | $CF_3$ | H | E-3a-1 |
| Cl | H | Cl | $CF_3$ | H | E-3a-2 |
| Cl | H | Cl | $CF_3$ | H | E-3a-3 |
| Cl | H | Cl | $CF_3$ | $CH_3$ | E-3a-1 |
| Cl | H | Cl | $CF_3$ | $CH_3$ | E-3a-2 |
| Cl | H | Cl | $CF_3$ | $CH_3$ | E-3a-3 |
| Cl | H | Cl | $CF_3$ | Et | E-3a-1 |
| Cl | H | Cl | $CF_3$ | Et | E-3a-2 |
| Cl | H | Cl | $CF_3$ | Et | E-3a-3 |
| Cl | H | Cl | $CF_3$ | $CH_2OCH_3$ | E-3a-1 |
| Cl | H | Cl | $CF_3$ | $CH_2OCH_3$ | E-3a-2 |
| Cl | H | Cl | $CF_3$ | $CH_2OCH_3$ | E-3a-3 |
| Cl | H | Cl | $CF_3$ | $CH_2OEt$ | E-3a-1 |
| Cl | H | Cl | $CF_3$ | $CH_2OEt$ | E-3a-2 |
| Cl | H | Cl | $CF_3$ | $CH_2OEt$ | E-3a-3 |
| Cl | H | Cl | $CF_3$ | $CH_2OC(O)CH_3$ | E-3a-1 |
| Cl | H | Cl | $CF_3$ | $CH_2OC(O)CH_3$ | E-3a-2 |
| Cl | H | Cl | $CF_3$ | $CH_2OC(O)CH_3$ | E-3a-3 |
| Cl | H | Cl | $CF_3$ | $CH_2OC(O)OCH_3$ | E-3a-1 |
| Cl | H | Cl | $CF_3$ | $CH_2OC(O)OCH_3$ | E-3a-2 |
| Cl | H | Cl | $CF_3$ | $CH_2OC(O)OCH_3$ | E-3a-3 |
| Cl | H | Cl | $CF_3$ | $CH_2CN$ | E-3a-1 |
| Cl | H | Cl | $CF_3$ | $CH_2CN$ | E-3a-2 |
| Cl | H | Cl | $CF_3$ | $CH_2CN$ | E-3a-3 |
| Cl | H | Cl | $CF_3$ | $CH_2C(S)NH_2$ | E-3a-1 |
| Cl | H | Cl | $CF_3$ | $CH_2C(S)NH_2$ | E-3a-2 |
| Cl | H | Cl | $CF_3$ | $CH_2C(S)NH_2$ | E-3a-3 |
| Cl | H | Cl | $CF_3$ | $CH_2C\equiv CH$ | E-3a-1 |
| Cl | H | Cl | $CF_3$ | $CH_2C\equiv CH$ | E-3a-2 |
| Cl | H | Cl | $CF_3$ | $CH_2C\equiv CH$ | E-3a-3 |
| Cl | H | Cl | $CF_3$ | $C(O)CH_3$ | E-3a-1 |
| Cl | H | Cl | $CF_3$ | $C(O)CH_3$ | E-3a-2 |
| Cl | H | Cl | $CF_3$ | $C(O)CH_3$ | E-3a-3 |
| Cl | H | Cl | $CF_3$ | C(O)Et | E-3a-1 |
| Cl | H | Cl | $CF_3$ | C(O)Et | E-3a-2 |
| Cl | H | Cl | $CF_3$ | C(O)Et | E-3a-3 |
| Cl | H | Cl | $CF_3$ | C(O)Pr-n | E-3a-1 |
| Cl | H | Cl | $CF_3$ | C(O)Pr-n | E-3a-2 |
| Cl | H | Cl | $CF_3$ | C(O)Pr-n | E-3a-3 |
| Cl | H | Cl | $CF_3$ | C(O)Pr-i | E-3a-1 |
| Cl | H | Cl | $CF_3$ | C(O)Pr-i | E-3a-2 |
| Cl | H | Cl | $CF_3$ | C(O)Pr-i | E-3a-3 |
| Cl | H | Cl | $CF_3$ | C(O)Pr-c | E-3a-1 |
| Cl | H | Cl | $CF_3$ | C(O)Pr-c | E-3a-2 |
| Cl | H | Cl | $CF_3$ | C(O)Pr-c | E-3a-3 |
| Cl | H | Cl | $CF_3$ | C(O)Bu-t | E-3a-1 |
| Cl | H | Cl | $CF_3$ | C(O)Bu-t | E-3a-2 |
| Cl | H | Cl | $CF_3$ | C(O)Bu-t | E-3a-3 |
| Cl | H | Cl | $CF_3$ | $C(O)CH_2OCH_3$ | E-3a-1 |
| Cl | H | Cl | $CF_3$ | $C(O)CH_2OCH_3$ | E-3a-2 |
| Cl | H | Cl | $CF_3$ | $C(O)CH_2OCH_3$ | E-3a-3 |
| Cl | H | Cl | $CF_3$ | $C(O)CH=CH_2$ | E-3a-1 |
| Cl | H | Cl | $CF_3$ | $C(O)CH=CH_2$ | E-3a-2 |
| Cl | H | Cl | $CF_3$ | $C(O)CH=CH_2$ | E-3a-3 |
| Cl | H | Cl | $CF_3$ | $C(O)OCH_3$ | E-3a-1 |
| Cl | H | Cl | $CF_3$ | $C(O)OCH_3$ | E-3a-2 |
| Cl | H | Cl | $CF_3$ | $C(O)OCH_3$ | E-3a-3 |
| Cl | H | Cl | $CF_3$ | C(O)OEt | E-3a-1 |
| Cl | H | Cl | $CF_3$ | C(O)OEt | E-3a-2 |
| Cl | H | Cl | $CF_3$ | C(O)OEt | E-3a-3 |
| Cl | H | Cl | $CF_3$ | C(O)OPr-i | E-3a-1 |
| Cl | H | Cl | $CF_3$ | C(O)OPr-i | E-3a-2 |
| Cl | H | Cl | $CF_3$ | C(O)OPr-i | E-3a-3 |
| Cl | H | Cl | $CF_3$ | $C(O)OCH_2CH_2OCH_3$ | E-3a-1 |
| Cl | H | Cl | $CF_3$ | $C(O)OCH_2CH_2OCH_3$ | E-3a-2 |
| Cl | H | Cl | $CF_3$ | $C(O)OCH_2CH_2OCH_3$ | E-3a-3 |
| Cl | H | Cl | $CF_3$ | $C(O)OCH_2CH=CH_2$ | E-3a-1 |
| Cl | H | Cl | $CF_3$ | $C(O)OCH_2CH=CH_2$ | E-3a-2 |
| Cl | H | Cl | $CF_3$ | $C(O)OCH_2CH=CH_2$ | E-3a-3 |
| Cl | H | Cl | $CF_3$ | H | E-3b-1 |
| Cl | H | Cl | $CF_3$ | H | E-3b-2 |
| Cl | H | Cl | $CF_3$ | H | E-3b-3 |
| Cl | H | Cl | $CF_3$ | H | E-3c-1 |
| Cl | H | Cl | $CF_3$ | H | E-3c-2 |
| Cl | H | Cl | $CF_3$ | H | E-3c-3 |
| Cl | H | Cl | $CF_3$ | H | E-3d-1 |
| Cl | H | Cl | $CF_3$ | H | E-4a-1 |

TABLE 1-continued

| | | | | | |
|---|---|---|---|---|---|
| Cl | H | Cl | CF$_3$ | H | E-4b-1 |
| Cl | H | Cl | CF$_3$ | H | (E-5)Et |
| Cl | H | Cl | CF$_3$ | H | (E-6) CH$_3$ |
| Cl | H | Cl | CF$_3$ | H | (E-6)Et |
| Cl | H | Cl | CF$_3$ | H | (E-6)Bu-n |
| Cl | H | Cl | CF$_3$ | H | (E-6)CH$_2$CHF$_2$ |
| Cl | H | Cl | CF$_3$ | H | (E-6)CH$_2$CF$_3$ |
| Cl | H | Cl | CF$_3$ | H | (E-6)CH$_2$CH$_2$OCH$_3$ |
| Cl | H | Cl | CF$_3$ | H | (E-6)(T-1) |
| Cl | H | Cl | CF$_3$ | H | (E-6)CH$_2$C≡CH |
| Cl | H | Cl | CF$_3$ | H | CH$_2$(E-9)Et |
| Cl | H | Cl | CF$_2$Cl | H | E-3a-1 |
| Cl | H | Cl | CF$_2$Cl | H | E-3a-2 |
| Cl | H | Cl | CF$_2$Cl | H | E-3a-3 |
| Cl | H | Cl | CF$_2$Cl | H | E-3b-1 |
| Cl | H | Cl | CF$_2$Cl | H | (E-6)Et |
| Cl | H | Cl | CF$_2$Cl | H | (E-6)CH$_2$CHF$_2$ |
| Cl | H | Cl | CF$_2$Cl | H | (E-6)CH$_2$CF$_3$ |
| Br | F | H | CF$_3$ | H | E-3a-1 |
| Br | F | H | CF$_3$ | H | E-3a-2 |
| Br | F | H | CF$_3$ | H | E-3a-3 |
| Br | F | H | CF$_3$ | H | E-3b-1 |
| Br | F | H | CF$_3$ | H | (E-6)Et |
| Br | F | H | CF$_3$ | H | (E-6)CH$_2$CHF$_2$ |
| Br | F | H | CF$_3$ | H | (E-6)CH$_2$CF$_3$ |
| Br | H | F | CF$_3$ | H | E-3a-1 |
| Br | H | F | CF$_3$ | H | E-3a-2 |
| Br | H | F | CF$_3$ | H | E-3a-3 |
| Br | H | F | CF$_3$ | H | E-3b-1 |
| Br | H | F | CF$_3$ | H | (E-6)Et |
| Br | H | F | CF$_3$ | H | (E-6)CH$_2$CHF$_2$ |
| Br | H | F | CF$_3$ | H | (E-6)CH$_2$CF$_3$ |
| Cl | Br | H | CF$_3$ | H | E-3a-1 |
| Cl | Br | H | CF$_3$ | H | E-3a-2 |
| Cl | Br | H | CF$_3$ | H | E-3a-3 |
| Br | Cl | H | CF$_3$ | H | E-3a-1 |
| Br | Cl | H | CF$_3$ | H | E-3a-2 |
| Br | Cl | H | CF$_3$ | H | E-3a-3 |
| Br | Cl | H | CF$_3$ | H | E-3b-1 |
| Br | Cl | H | CF$_3$ | H | (E-6)Et |
| Br | Cl | H | CF$_3$ | H | (E-6)CH$_2$CHF$_2$ |
| Br | Cl | H | CF$_3$ | H | (E-6)CH$_2$CF$_3$ |
| Br | H | Cl | CF$_3$ | H | E-3a-1 |
| Br | H | Cl | CF$_3$ | H | E-3a-2 |
| Br | H | Cl | CF$_3$ | H | E-3a-3 |
| Br | H | Cl | CF$_3$ | CH$_2$CN | E-3a-1 |
| Br | H | Cl | CF$_3$ | CH$_2$CN | E-3a-2 |
| Br | H | Cl | CF$_3$ | CH$_2$CN | E-3a-3 |
| Br | H | Cl | CF$_3$ | C(O)CH$_3$ | E-3a-1 |
| Br | H | Cl | CF$_3$ | C(O)CH$_3$ | E-3a-2 |
| Br | H | Cl | CF$_3$ | C(O)CH$_3$ | E-3a-3 |
| Br | H | Cl | CF$_3$ | C(O)Et | E-3a-1 |
| Br | H | Cl | CF$_3$ | C(O)Et | E-3a-2 |
| Br | H | Cl | CF$_3$ | C(O)Et | E-3a-3 |
| Br | H | Cl | CF$_3$ | C(O)OCH$_3$ | E-3a-1 |
| Br | H | Cl | CF$_3$ | C(O)OCH$_3$ | E-3a-2 |
| Br | H | Cl | CF$_3$ | C(O)OCH$_3$ | E-3a-3 |
| Br | H | Cl | CF$_3$ | H | E-3b-1 |
| Br | H | Cl | CF$_3$ | H | E-3b-2 |
| Br | H | Cl | CF$_3$ | H | E-3b-3 |
| Br | H | Cl | CF$_3$ | H | E-4a-1 |
| Br | H | Cl | CF$_3$ | H | (E-6)Et |
| Br | H | Cl | CF$_3$ | H | (E-6)CH$_2$CHF$_2$ |
| Br | H | Cl | CF$_3$ | H | (E-6)CH$_2$CF$_3$ |
| Br | H | Cl | CF$_2$Cl | H | E-3a-1 |
| Br | H | Cl | CF$_2$Cl | H | E-3a-2 |
| Br | H | Cl | CF$_2$Cl | H | E-3a-3 |
| Br | Br | H | CF$_3$ | H | E-3a-1 |
| Br | Br | H | CF$_3$ | H | E-3a-2 |
| Br | Br | H | CF$_3$ | H | E-3a-3 |
| Br | H | Br | CF$_3$ | H | E-3a-1 |
| Br | H | Br | CF$_3$ | H | E-3a-2 |
| Br | H | Br | CF$_3$ | H | E-3a-3 |
| Br | H | Br | CF$_3$ | CH$_2$CN | E-3a-1 |
| Br | H | Br | CF$_3$ | CH$_2$CN | E-3a-2 |
| Br | H | Br | CF$_3$ | CH$_2$CN | E-3a-3 |
| Br | H | Br | CF$_3$ | C(O)CH$_3$ | E-3a-1 |
| Br | H | Br | CF$_3$ | C(O)CH$_3$ | E-3a-2 |
| Br | H | Br | CF$_3$ | C(O)CH$_3$ | E-3a-3 |
| Br | H | Br | CF$_3$ | C(O)Et | E-3a-1 |
| Br | H | Br | CF$_3$ | C(O)Et | E-3a-2 |
| Br | H | Br | CF$_3$ | C(O)Et | E-3a-3 |
| Br | H | Br | CF$_3$ | C(O)OCH$_3$ | E-3a-1 |
| Br | H | Br | CF$_3$ | C(O)OCH$_3$ | E-3a-2 |
| Br | H | Br | CF$_3$ | C(O)OCH$_3$ | E-3a-3 |
| Br | H | Br | CF$_3$ | H | E-3b-1 |
| Br | H | Br | CF$_3$ | H | E-3b-2 |
| Br | H | Br | CF$_3$ | H | E-3b-3 |
| Br | H | Br | CF$_3$ | H | E-4a-1 |
| Br | H | Br | CF$_3$ | H | (E-6)Et |
| Br | H | Br | CF$_3$ | H | (E-6)CH$_2$CHF$_2$ |
| Br | H | Br | CF$_3$ | H | (E-6)CH$_2$CF$_3$ |
| Br | H | Br | CF$_2$Cl | H | E-3a-1 |
| Br | H | Br | CF$_2$Cl | H | E-3a-2 |
| Br | H | Br | CF$_2$Cl | H | E-3a-3 |
| I | F | H | CF$_3$ | H | E-3a-1 |
| I | F | H | CF$_3$ | H | E-3a-2 |
| I | F | H | CF$_3$ | H | E-3a-3 |
| I | F | H | CF$_3$ | H | E-3b-1 |
| I | F | H | CF$_3$ | H | (E-6)Et |
| I | F | H | CF$_3$ | H | (E-6)CH$_2$CF$_3$ |
| I | H | F | CF$_3$ | H | E-3a-1 |
| I | H | F | CF$_3$ | H | E-3a-2 |
| I | H | F | CF$_3$ | H | E-3a-3 |
| I | H | F | CF$_3$ | H | E-3b-1 |
| I | H | F | CF$_3$ | H | (E-6)Et |
| I | H | F | CF$_3$ | H | (E-6)CH$_2$CF$_3$ |
| I | H | Cl | CF$_3$ | H | E-3a-1 |
| I | H | Cl | CF$_3$ | H | E-3a-2 |
| I | H | Cl | CF$_3$ | H | E-3a-3 |
| I | H | Cl | CF$_3$ | H | E-3b-1 |
| I | H | Cl | CF$_3$ | H | (E-6)Et |
| I | H | Cl | CF$_3$ | H | (E-6)CH$_2$CHF$_2$ |
| I | H | Cl | CF$_3$ | H | (E-6)CH$_2$CF$_3$ |
| Cl | H | CH$_3$ | CF$_3$ | H | E-3a-1 |
| Cl | H | CH$_3$ | CF$_3$ | H | E-3a-2 |
| Cl | H | CH$_3$ | CF$_3$ | H | E-3a-3 |
| Br | H | CH$_3$ | CF$_3$ | H | E-3a-1 |
| Br | H | CH$_3$ | CF$_3$ | H | E-3a-2 |
| Br | H | CH$_3$ | CF$_3$ | H | E-3a-3 |
| CF$_3$ | F | H | CF$_3$ | H | E-3a-1 |
| CF$_3$ | F | H | CF$_3$ | H | E-3a-2 |
| CF$_3$ | F | H | CF$_3$ | H | E-3a-3 |
| CF$_3$ | F | H | CF$_3$ | H | E-3b-1 |
| CF$_3$ | F | H | CF$_3$ | H | (E-6)Et |
| CF$_3$ | F | H | CF$_3$ | H | (E-6)CH$_2$CHF$_2$ |
| CF$_3$ | F | H | CF$_3$ | H | (E-6)CH$_2$CF$_3$ |
| CF$_3$ | H | F | CF$_3$ | H | E-3a-1 |
| CF$_3$ | H | F | CF$_3$ | H | E-3a-2 |
| CF$_3$ | H | F | CF$_3$ | H | E-3a-3 |
| CF$_3$ | H | F | CF$_3$ | H | E-3b-1 |
| CF$_3$ | H | F | CF$_3$ | H | (E-6)Et |
| CF$_3$ | H | F | CF$_3$ | H | (E-6)CH$_2$CHF$_2$ |
| CF$_3$ | H | F | CF$_3$ | H | (E-6)CH$_2$CF$_3$ |
| CF$_3$ | Cl | H | CF$_3$ | H | E-3a-1 |
| CF$_3$ | Cl | H | CF$_3$ | H | E-3a-2 |
| CF$_3$ | Cl | H | CF$_3$ | H | E-3a-3 |
| CF$_3$ | Cl | H | CF$_3$ | H | E-3b-1 |
| CF$_3$ | Cl | H | CF$_3$ | H | (E-6)Et |
| CF$_3$ | Cl | H | CF$_3$ | H | (E-6)CH$_2$CHF$_2$ |
| CF$_3$ | Cl | H | CF$_3$ | H | (E-6)CH$_2$CF$_3$ |
| CF$_3$ | H | Cl | CF$_3$ | H | E-3a-1 |
| CF$_3$ | H | Cl | CF$_3$ | H | E-3a-2 |
| CF$_3$ | H | Cl | CF$_3$ | H | E-3a-3 |
| CF$_3$ | H | Cl | CF$_3$ | Et | E-3a-1 |
| CF$_3$ | H | Cl | CF$_3$ | Et | E-3a-2 |
| CF$_3$ | H | Cl | CF$_3$ | Et | E-3a-3 |
| CF$_3$ | H | Cl | CF$_3$ | CH$_2$OCH$_3$ | E-3a-1 |
| CF$_3$ | H | Cl | CF$_3$ | CH$_2$OCH$_3$ | E-3a-2 |
| CF$_3$ | H | Cl | CF$_3$ | CH$_2$OCH$_3$ | E-3a-3 |
| CF$_3$ | H | Cl | CF$_3$ | CH$_2$CN | E-3a-1 |
| CF$_3$ | H | Cl | CF$_3$ | CH$_2$CN | E-3a-2 |
| CF$_3$ | H | Cl | CF$_3$ | CH$_2$CN | E-3a-3 |
| CF$_3$ | H | Cl | CF$_3$ | CH$_2$C≡CH | E-3a-1 |
| CF$_3$ | H | Cl | CF$_3$ | CH$_2$C≡CH | E-3a-2 |
| CF$_3$ | H | Cl | CF$_3$ | CH$_2$C≡CH | E-3a-3 |
| CF$_3$ | H | Cl | CF$_3$ | C(O)CH$_3$ | E-3a-1 |
| CF$_3$ | H | Cl | CF$_3$ | C(O)CH$_3$ | E-3a-2 |
| CF$_3$ | H | Cl | CF$_3$ | C(O)CH$_3$ | E-3a-3 |

TABLE 1-continued

| | | | | | |
|---|---|---|---|---|---|
| CF$_3$ | H | Cl | CF$_3$ | C(O)Et | E-3a-1 |
| CF$_3$ | H | Cl | CF$_3$ | C(O)Et | E-3a-2 |
| CF$_3$ | H | Cl | CF$_3$ | C(O)Et | E-3a-3 |
| CF$_3$ | H | Cl | CF$_3$ | C(O)Pr-c | E-3a-1 |
| CF$_3$ | H | Cl | CF$_3$ | C(O)Pr-c | E-3a-2 |
| CF$_3$ | H | Cl | CF$_3$ | C(O)Pr-c | E-3a-3 |
| CF$_3$ | H | Cl | CF$_3$ | C(O)Bu-t | E-3a-1 |
| CF$_3$ | H | Cl | CF$_3$ | C(O)Bu-t | E-3a-2 |
| CF$_3$ | H | Cl | CF$_3$ | C(O)Bu-t | E-3a-3 |
| CF$_3$ | H | Cl | CF$_3$ | C(O)CH$_2$OCH$_3$ | E-3a-1 |
| CF$_3$ | H | Cl | CF$_3$ | C(O)CH$_2$OCH$_3$ | E-3a-2 |
| CF$_3$ | H | Cl | CF$_3$ | C(O)CH$_2$OCH$_3$ | E-3a-3 |
| CF$_3$ | H | Cl | CF$_3$ | C(O)CH=CH$_2$ | E-3a-1 |
| CF$_3$ | H | Cl | CF$_3$ | C(O)CH=CH$_2$ | E-3a-2 |
| CF$_3$ | H | Cl | CF$_3$ | C(O)CH=CH$_2$ | E-3a-3 |
| CF$_3$ | H | Cl | CF$_3$ | C(O)OCH$_3$ | E-3a-1 |
| CF$_3$ | H | Cl | CF$_3$ | C(O)OCH$_3$ | E-3a-2 |
| CF$_3$ | H | Cl | CF$_3$ | C(O)OCH$_3$ | E-3a-3 |
| CF$_3$ | H | Cl | CF$_3$ | H | E-3b-1 |
| CF$_3$ | H | Cl | CF$_3$ | H | E-3b-2 |
| CF$_3$ | H | Cl | CF$_3$ | H | E-3b-3 |
| CF$_3$ | H | Cl | CF$_3$ | H | E-4a-1 |
| CF$_3$ | H | Cl | CF$_3$ | H | (E-5)Et |
| CF$_3$ | H | Cl | CF$_3$ | H | (E-6)CH$_3$ |
| CF$_3$ | H | Cl | CF$_3$ | H | (E-6)Et |
| CF$_3$ | H | Cl | CF$_3$ | H | (E-6)Bu-n |
| CF$_3$ | H | Cl | CF$_3$ | H | (E-6)CH$_2$CHF$_2$ |
| CF$_3$ | H | Cl | CF$_3$ | H | (E-6)CH$_2$CF$_3$ |
| CF$_3$ | H | Cl | CF$_3$ | H | (E-6)CH$_2$CH$_2$OCH$_3$ |
| CF$_3$ | H | Cl | CF$_3$ | H | (E-6)(T-1) |
| CF$_3$ | H | Cl | CF$_3$ | H | (E-6)CH$_2$C≡CH |
| CF$_3$ | H | Cl | CF$_3$ | H | CH$_2$(E-9)Et |
| CF$_3$ | H | Cl | CF$_2$Cl | H | E-3a-1 |
| CF$_3$ | H | Cl | CF$_2$Cl | H | E-3a-2 |
| CF$_3$ | H | Cl | CF$_2$Cl | H | E-3a-3 |
| CF$_3$ | H | Br | CF$_3$ | H | E-3a-1 |
| CF$_3$ | H | Br | CF$_3$ | H | E-3a-2 |
| CF$_3$ | H | Br | CF$_3$ | H | E-3a-3 |
| CF$_3$ | H | Br | CF$_3$ | Et | E-3a-1 |
| CF$_3$ | H | Br | CF$_3$ | Et | E-3a-2 |
| CF$_3$ | H | Br | CF$_3$ | Et | E-3a-3 |
| CF$_3$ | H | Br | CF$_3$ | CH$_2$OCH$_3$ | E-3a-1 |
| CF$_3$ | H | Br | CF$_3$ | CH$_2$OCH$_3$ | E-3a-2 |
| CF$_3$ | H | Br | CF$_3$ | CH$_2$OCH$_3$ | E-3a-3 |
| CF$_3$ | H | Br | CF$_3$ | CH$_2$CN | E-3a-1 |
| CF$_3$ | H | Br | CF$_3$ | CH$_2$CN | E-3a-2 |
| CF$_3$ | H | Br | CF$_3$ | CH$_2$CN | E-3a-3 |
| CF$_3$ | H | Br | CF$_3$ | CH$_2$C≡CH | E-3a-1 |
| CF$_3$ | H | Br | CF$_3$ | CH$_2$C≡CH | E-3a-2 |
| CF$_3$ | H | Br | CF$_3$ | CH$_2$C≡CH | E-3a-3 |
| CF$_3$ | H | Br | CF$_3$ | C(O)CH$_3$ | E-3a-1 |
| CF$_3$ | H | Br | CF$_3$ | C(O)CH$_3$ | E-3a-2 |
| CF$_3$ | H | Br | CF$_3$ | C(O)CH$_3$ | E-3a-3 |
| CF$_3$ | H | Br | CF$_3$ | C(O)Et | E-3a-1 |
| CF$_3$ | H | Br | CF$_3$ | C(O)Et | E-3a-2 |
| CF$_3$ | H | Br | CF$_3$ | C(O)Et | E-3a-3 |
| CF$_3$ | H | Br | CF$_3$ | C(O)Pr-c | E-3a-1 |
| CF$_3$ | H | Br | CF$_3$ | C(O)Pr-c | E-3a-2 |
| CF$_3$ | H | Br | CF$_3$ | C(O)Pr-c | E-3a-3 |
| CF$_3$ | H | Br | CF$_3$ | C(O)Bu-t | E-3a-1 |
| CF$_3$ | H | Br | CF$_3$ | C(O)Bu-t | E-3a-2 |
| CF$_3$ | H | Br | CF$_3$ | C(O)Bu-t | E-3a-3 |
| CF$_3$ | H | Br | CF$_3$ | C(O)CH$_2$OCH$_3$ | E-3a-1 |
| CF$_3$ | H | Br | CF$_3$ | C(O)CH$_2$OCH$_3$ | E-3a-2 |
| CF$_3$ | H | Br | CF$_3$ | C(O)CH$_2$OCH$_3$ | E-3a-3 |
| CF$_3$ | H | Br | CF$_3$ | C(O)CH=CH$_2$ | E-3a-1 |
| CF$_3$ | H | Br | CF$_3$ | C(O)CH=CH$_2$ | E-3a-2 |
| CF$_3$ | H | Br | CF$_3$ | C(O)CH=CH$_2$ | E-3a-3 |
| CF$_3$ | H | Br | CF$_3$ | C(O)OCH$_3$ | E-3a-1 |
| CF$_3$ | H | Br | CF$_3$ | C(O)OCH$_3$ | E-3a-2 |
| CF$_3$ | H | Br | CF$_3$ | C(O)OCH$_3$ | E-3a-3 |
| CF$_3$ | H | Br | CF$_3$ | H | E-3b-1 |
| CF$_3$ | H | Br | CF$_3$ | H | E-3b-2 |
| CF$_3$ | H | Br | CF$_3$ | H | E-3b-3 |
| CF$_3$ | H | Br | CF$_3$ | H | E-4a-1 |
| CF$_3$ | H | Br | CF$_3$ | H | (E-5)Et |
| CF$_3$ | H | Br | CF$_3$ | H | (E-6)CH$_3$ |
| CF$_3$ | H | Br | CF$_3$ | H | (E-6)Et |
| CF$_3$ | H | Br | CF$_3$ | H | (E-6)Bu-n |
| CF$_3$ | H | Br | CF$_3$ | H | (E-6)CH$_2$CHF$_2$ |
| CF$_3$ | H | Br | CF$_3$ | H | (E-6)CH$_2$CF$_3$ |
| CF$_3$ | H | Br | CF$_3$ | H | (E-6)CH$_2$CH$_2$OCH$_3$ |
| CF$_3$ | H | Br | CF$_3$ | H | (E-6)(T-1) |
| CF$_3$ | H | Br | CF$_3$ | H | (E-6)CH$_2$CH CH$_2$(E-9)Et |
| CF$_3$ | H | Br | CF$_2$Cl | H | E-3a-1 |
| CF$_3$ | H | Br | CF$_2$Cl | H | E-3a-2 |
| CF$_3$ | H | Br | CF$_2$Cl | H | E-3a-3 |
| CF$_3$ | H | I | CF$_3$ | H | E-3a-1 |
| CF$_3$ | H | I | CF$_3$ | H | E-3a-2 |
| CF$_3$ | H | I | CF$_3$ | H | E-3a-3 |
| CF$_3$ | H | I | CF$_3$ | H | E-3b-1 |
| CF$_3$ | H | I | CF$_3$ | H | (E-6)Et |
| CF$_3$ | H | I | CF$_3$ | H | (E-6)CH$_2$CHF$_2$ |
| CF$_3$ | H | I | CF$_3$ | H | (E-6)CH$_2$CF$_3$ |
| CF$_3$ | H | CH$_3$ | CF$_3$ | H | E-3a-1 |
| CF$_3$ | H | CH$_3$ | CF$_3$ | H | E-3a-2 |
| CF$_3$ | H | CH$_3$ | CF$_3$ | H | E-3a-3 |
| CF$_3$ | H | CF$_3$ | CF$_3$ | H | E-3a-1 |
| CF$_3$ | H | CF$_3$ | CF$_3$ | H | E-3a-2 |
| CF$_3$ | H | CF$_3$ | CF$_3$ | H | E-3a-3 |
| CF$_3$ | H | CF$_3$ | CF$_3$ | Et | E-3a-1 |
| CF$_3$ | H | CF$_3$ | CF$_3$ | Et | E-3a-2 |
| CF$_3$ | H | CF$_3$ | CF$_3$ | Et | E-3a-3 |
| CF$_3$ | H | CF$_3$ | CF$_3$ | CH$_2$OCH$_3$ | E-3a-1 |
| CF$_3$ | H | CF$_3$ | CF$_3$ | CH$_2$OCH$_3$ | E-3a-2 |
| CF$_3$ | H | CF$_3$ | CF$_3$ | CH$_2$OCH$_3$ | E-3a-3 |
| CF$_3$ | H | CF$_3$ | CF$_3$ | CH$_2$CN | E-3a-1 |
| CF$_3$ | H | CF$_3$ | CF$_3$ | CH$_2$CN | E-3a-2 |
| CF$_3$ | H | CF$_3$ | CF$_3$ | CH$_2$CN | E-3a-3 |
| CF$_3$ | H | CF$_3$ | CF$_3$ | CH$_2$C≡CH | E-3a-1 |
| CF$_3$ | H | CF$_3$ | CF$_3$ | CH$_2$C≡CH | E-3a-2 |
| CF$_3$ | H | CF$_3$ | CF$_3$ | CH$_2$C≡CH | E-3a-3 |
| CF$_3$ | H | CF$_3$ | CF$_3$ | C(O)CH$_3$ | E-3a-1 |
| CF$_3$ | H | CF$_3$ | CF$_3$ | C(O)CH$_3$ | E-3a-2 |
| CF$_3$ | H | CF$_3$ | CF$_3$ | C(O)CH$_3$ | E-3a-3 |
| CF$_3$ | H | CF$_3$ | CF$_3$ | C(O)Et | E-3a-1 |
| CF$_3$ | H | CF$_3$ | CF$_3$ | C(O)Et | E-3a-2 |
| CF$_3$ | H | CF$_3$ | CF$_3$ | C(O)Et | E-3a-3 |
| CF$_3$ | H | CF$_3$ | CF$_3$ | C(O)Pr-c | E-3a-1 |
| CF$_3$ | H | CF$_3$ | CF$_3$ | C(O)Pr-c | E-3a-2 |
| CF$_3$ | H | CF$_3$ | CF$_3$ | C(O)Pr-c | E-3a-3 |
| CF$_3$ | H | CF$_3$ | CF$_3$ | C(O)Bu-t | E-3a-1 |
| CF$_3$ | H | CF$_3$ | CF$_3$ | C(O)Bu-t | E-3a-2 |
| CF$_3$ | H | CF$_3$ | CF$_3$ | C(O)Bu-t | E-3a-3 |
| CF$_3$ | H | CF$_3$ | CF$_3$ | C(O)CH$_2$OCH$_3$ | E-3a-1 |
| CF$_3$ | H | CF$_3$ | CF$_3$ | C(O)CH$_2$OCH$_3$ | E-3a-2 |
| CF$_3$ | H | CF$_3$ | CF$_3$ | C(O)CH$_2$OCH$_3$ | E-3a-3 |
| CF$_3$ | H | CF$_3$ | CF$_3$ | C(O)CH=CH$_2$ | E-3a-1 |
| CF$_3$ | H | CF$_3$ | CF$_3$ | C(O)CH=CH$_2$ | E-3a-2 |
| CF$_3$ | H | CF$_3$ | CF$_3$ | C(O)CH=CH$_2$ | E-3a-3 |
| CF$_3$ | H | CF$_3$ | CF$_3$ | C(O)OCH$_3$ | E-3a-1 |
| CF$_3$ | H | CF$_3$ | CF$_3$ | C(O)OCH$_3$ | E-3a-2 |
| CF$_3$ | H | CF$_3$ | CF$_3$ | C(O)OCH$_3$ | E-3a-3 |
| CF$_3$ | H | CF$_3$ | CF$_3$ | H | E-3b-1 |
| CF$_3$ | H | CF$_3$ | CF$_3$ | H | E-3b-2 |
| CF$_3$ | H | CF$_3$ | CF$_3$ | H | E-3b-3 |
| CF$_3$ | H | CF$_3$ | CF$_3$ | H | E-4a-1 |
| CF$_3$ | H | CF$_3$ | CF$_3$ | H | (E-5)Et |
| CF$_3$ | H | CF$_3$ | CF$_3$ | H | (E-6)CH$_3$ |
| CF$_3$ | H | CF$_3$ | CF$_3$ | H | (E-6)Et |
| CF$_3$ | H | CF$_3$ | CF$_3$ | H | (E-6)Bu-n |
| CF$_3$ | H | CF$_3$ | CF$_3$ | H | (E-6)CH$_2$CHF$_2$ |
| CF$_3$ | H | CF$_3$ | CF$_3$ | H | (E-6)CH$_2$CF$_3$ |
| CF$_3$ | H | CF$_3$ | CF$_3$ | H | (E-6)CH$_2$CH$_2$OCH$_3$ |
| CF$_3$ | H | CF$_3$ | CF$_3$ | H | (E-6)(T-1) |
| CF$_3$ | H | CF$_3$ | CF$_3$ | H | (E-6)CH$_2$C≡CH CH$_2$(E-9)Et |
| CF$_3$ | H | CF$_3$ | CF$_2$Cl | H | E-3a-1 |
| CF$_3$ | H | CF$_3$ | CF$_2$Cl | H | E-3a-2 |
| CF$_3$ | H | CF$_3$ | CF$_2$Cl | H | E-3a-3 |
| CF$_3$ | H | OCH$_3$ | CF$_3$ | H | E-3a-1 |
| CF$_3$ | H | OCH$_3$ | CF$_3$ | H | E-3a-2 |
| CF$_3$ | H | OCH$_3$ | CF$_3$ | H | E-3a-3 |
| Cl | H | OCHF$_2$ | CF$_3$ | H | E-3a-1 |
| Cl | H | OCHF$_2$ | CF$_3$ | H | E-3a-2 |
| Cl | H | OCHF$_2$ | CF$_3$ | H | E-3a-3 |

TABLE 1-continued

| | | | | | |
|---|---|---|---|---|---|
| Br | H | OCHF₂ | CF₃ | H | E-3a-1 |
| Br | H | OCHF₂ | CF₃ | H | E-3a-2 |
| Br | H | OCHF₂ | CF₃ | H | E-3a-3 |
| CF₃ | H | OCHF₂ | CF₃ | H | E-3a-1 |
| CF₃ | H | OCHF₂ | CF₃ | H | E-3a-2 |
| CF₃ | H | OCHF₂ | CF₃ | H | E-3a-3 |
| Cl | H | OCF₃ | CF₃ | H | E-3a-1 |
| Cl | H | OCF₃ | CF₃ | H | E-3a-2 |
| Cl | H | OCF₃ | CF₃ | H | E-3a-3 |
| Br | H | OCF₃ | CF₃ | H | E-3a-1 |
| Br | H | OCF₃ | CF₃ | H | E-3a-2 |
| Br | H | OCF₃ | CF₃ | H | E-3a-3 |
| CF₃ | H | OCF₃ | CF₃ | H | E-3a-1 |
| CF₃ | H | OCF₃ | CF₃ | H | E-3a-2 |
| CF₃ | H | OCF₃ | CF₃ | H | E-3a-3 |
| Cl | H | SCF₃ | CF₃ | H | E-3a-1 |
| Cl | H | SCF₃ | CF₃ | H | E-3a-2 |
| Cl | H | SCF₃ | CF₃ | H | E-3a-3 |
| Br | H | SCF₃ | CF₃ | H | E-3a-1 |
| Br | H | SCF₃ | CF₃ | H | E-3a-2 |
| Br | H | SCF₃ | CF₃ | H | E-3a-3 |
| CF₃ | H | CN | CF₃ | H | E-3a-1 |
| CF₃ | H | CN | CF₃ | H | E-3a-2 |
| CF₃ | H | CN | CF₃ | H | E-3a-3 |
| CF₃ | H | CN | CF₃ | H | E-3b-1 |
| CF₃ | H | CN | CF₃ | H | (E-6)Et |
| CF₃ | H | CN | CF₃ | H | (E-6)CH₂CF₃ |
| F | F | F | CF₃ | H | E-3a-1 |
| F | F | F | CF₃ | H | E-3a-2 |
| F | F | F | CF₃ | H | E-3a-3 |
| F | F | F | CF₃ | H | E-3b-1 |
| F | F | F | CF₃ | H | (E-6)Et |
| F | F | F | CF₃ | H | (E-6)CH₂CF₃ |
| Cl | F | Cl | CF₃ | H | E-3a-1 |
| Cl | F | Cl | CF₃ | H | E-3a-2 |
| Cl | F | Cl | CF₃ | H | E-3a-3 |
| Cl | F | Cl | CF₃ | Et | E-3a-1 |
| Cl | F | Cl | CF₃ | Et | E-3a-2 |
| Cl | F | Cl | CF₃ | Et | E-3a-3 |
| Cl | F | Cl | CF₃ | CH₂OCH₃ | E-3a-1 |
| Cl | F | Cl | CF₃ | CH₂OCH₃ | E-3a-2 |
| Cl | F | Cl | CF₃ | CH₂OCH₃ | E-3a-3 |
| Cl | F | Cl | CF₃ | CH₂CN | E-3a-1 |
| Cl | F | Cl | CF₃ | CH₂CN | E-3a-2 |
| Cl | F | Cl | CF₃ | CH₂CN | E-3a-3 |
| Cl | F | Cl | CF₃ | CH₂C≡CH | E-3a-1 |
| Cl | F | Cl | CF₃ | CH₂C≡CH | E-3a-2 |
| Cl | F | Cl | CF₃ | CH₂C≡CH | E-3a-3 |
| Cl | F | Cl | CF₃ | C(O)CH₃ | E-3a-1 |
| Cl | F | Cl | CF₃ | C(O)CH₃ | E-3a-2 |
| Cl | F | Cl | CF₃ | C(O)CH₃ | E-3a-3 |
| Cl | F | Cl | CF₃ | C(O)Et | E-3a-1 |
| Cl | F | Cl | CF₃ | C(O)Et | E-3a-2 |
| Cl | F | Cl | CF₃ | C(O)Et | E-3a-3 |
| Cl | F | Cl | CF₃ | C(O)Pr-c | E-3a-1 |
| Cl | F | Cl | CF₃ | C(O)Pr-c | E-3a-2 |
| Cl | F | Cl | CF₃ | C(O)Pr-c | E-3a-3 |
| Cl | F | Cl | CF₃ | C(O)Bu-t | E-3a-1 |
| Cl | F | Cl | CF₃ | C(O)Bu-t | E-3a-2 |
| Cl | F | Cl | CF₃ | C(O)Bu-t | E-3a-3 |
| Cl | F | Cl | CF₃ | C(O)CH₂OCH₃ | E-3a-1 |
| Cl | F | Cl | CF₃ | C(O)CH₂OCH₃ | E-3a-2 |
| Cl | F | Cl | CF₃ | C(O)CH₂OCH₃ | E-3a-3 |
| Cl | F | Cl | CF₃ | C(O)CH=CH₂ | E-3a-1 |
| Cl | F | Cl | CF₃ | C(O)CH=CH₂ | E-3a-2 |
| Cl | F | Cl | CF₃ | C(O)CH=CH₂ | E-3a-3 |
| Cl | F | Cl | CF₃ | C(O)OCH₃ | E-3a-1 |
| Cl | F | Cl | CF₃ | C(O)OCH₃ | E-3a-2 |
| Cl | F | Cl | CF₃ | C(O)OCH₃ | E-3a-3 |
| Cl | F | Cl | CF₃ | H | E-3b-1 |
| Cl | F | Cl | CF₃ | H | E-3b-2 |
| Cl | F | Cl | CF₃ | H | E-3b-3 |
| Cl | F | Cl | CF₃ | H | E-4a-1 |
| Cl | F | Cl | CF₃ | H | (E-5)Et |
| Cl | F | Cl | CF₃ | H | (E-6)CH₃ |
| Cl | F | Cl | CF₃ | H | (E-6)Et |
| Cl | F | Cl | CF₃ | H | (E-6)Bu-n |
| Cl | F | Cl | CF₃ | H | (E-6)CH₂CHF₂ |
| Cl | F | Cl | CF₃ | H | (E-6)CH₂CF₃ |
| Cl | F | Cl | CF₃ | H | (E-6)CH₂CH₂OCH₃ |
| Cl | F | Cl | CF₃ | H | (E-6)(T-1) |
| Cl | F | Cl | CF₃ | H | (E-6)CH₂C≡CH |
| Cl | F | Cl | CF₃ | H | CH₂(E-9)Et |
| Cl | F | Cl | CF₂Cl | H | E-3a-1 |
| Cl | F | Cl | CF₂Cl | H | E-3a-2 |
| Cl | F | Cl | CF₂Cl | H | E-3a-3 |
| Cl | Cl | Cl | CF₃ | H | E-3a-1 |
| Cl | Cl | Cl | CF₃ | H | E-3a-2 |
| Cl | Cl | Cl | CF₃ | H | E-3a-3 |
| Cl | Cl | Cl | CF₃ | CH₂CN | E-3a-1 |
| Cl | Cl | Cl | CF₃ | CH₂CN | E-3a-2 |
| Cl | Cl | Cl | CF₃ | CH₂CN | E-3a-3 |
| Cl | Cl | Cl | CF₃ | C(O)CH₃ | E-3a-1 |
| Cl | Cl | Cl | CF₃ | C(O)CH₃ | E-3a-2 |
| Cl | Cl | Cl | CF₃ | C(O)CH₃ | E-3a-3 |
| Cl | Cl | Cl | CF₃ | C(O)Et | E-3a-1 |
| Cl | Cl | Cl | CF₃ | C(O)Et | E-3a-2 |
| Cl | Cl | Cl | CF₃ | C(O)Et | E-3a-3 |
| Cl | Cl | Cl | CF₃ | C(O)CH₃ | E-3a-1 |
| Cl | Cl | Cl | CF₃ | C(O)CH₃ | E-3a-2 |
| Cl | Cl | Cl | CF₃ | C(O)CH₃ | E-3a-3 |
| Cl | Cl | Cl | CF₃ | H | E-3b-1 |
| Cl | Cl | Cl | CF₃ | H | (E-6)Et |
| Cl | Cl | Cl | CF₃ | H | (E-6)CH₂CHF₂ |
| Cl | Cl | Cl | CF₃ | H | (E-6)CH₂CF₃ |
| Br | F | Br | CF₃ | H | E-3a-1 |
| Br | F | Br | CF₃ | H | E-3a-2 |
| Br | F | Br | CF₃ | H | E-3a-3 |
| Br | F | Br | CF₃ | Et | E-3a-1 |
| Br | F | Br | CF₃ | Et | E-3a-2 |
| Br | F | Br | CF₃ | Et | E-3a-3 |
| Br | F | Br | CF₃ | CH₂OCH₃ | E-3a-1 |
| Br | F | Br | CF₃ | CH₂OCH₃ | E-3a-2 |
| Br | F | Br | CF₃ | CH₂OCH₃ | E-3a-3 |
| Br | F | Br | CF₃ | CH₂CN | E-3a-1 |
| Br | F | Br | CF₃ | CH₂CN | E-3a-2 |
| Br | F | Br | CF₃ | CH₂CN | E-3a-3 |
| Br | F | Br | CF₃ | CH₂C≡CH | E-3a-1 |
| Br | F | Br | CF₃ | CH₂C≡CH | E-3a-2 |
| Br | F | Br | CF₃ | CH₂C≡CH | E-3a-3 |
| Br | F | Br | CF₃ | C(O)CH₃ | E-3a-1 |
| Br | F | Br | CF₃ | C(O)CH₃ | E-3a-2 |
| Br | F | Br | CF₃ | C(O)CH₃ | E-3a-3 |
| Br | F | Br | CF₃ | C(O)Et | E-3a-1 |
| Br | F | Br | CF₃ | C(O)Et | E-3a-2 |
| Br | F | Br | CF₃ | C(O)Et | E-3a-3 |
| Br | F | Br | CF₃ | C(O)Pr-c | E-3a-1 |
| Br | F | Br | CF₃ | C(O)Pr-c | E-3a-2 |
| Br | F | Br | CF₃ | C(O)Pr-c | E-3a-3 |
| Br | F | Br | CF₃ | C(O)Bu-t | E-3a-1 |
| Br | F | Br | CF₃ | C(O)Bu-t | E-3a-2 |
| Br | F | Br | CF₃ | C(O)Bu-t | E-3a-3 |
| Br | F | Br | CF₃ | C(O)CH₂OCH₃ | E-3a-1 |
| Br | F | Br | CF₃ | C(O)CH₂OCH₃ | E-3a-2 |
| Br | F | Br | CF₃ | C(O)CH₂OCH₃ | E-3a-3 |
| Br | F | Br | CF₃ | C(O)CH=CH₂ | E-3a-1 |
| Br | F | Br | CF₃ | C(O)CH=CH₂ | E-3a-2 |
| Br | F | Br | CF₃ | C(O)CH=CH₂ | E-3a-3 |
| Br | F | Br | CF₃ | C(O)OCH₃ | E-3a-1 |
| Br | F | Br | CF₃ | C(O)OCH₃ | E-3a-2 |
| Br | F | Br | CF₃ | C(O)OCH₃ | E-3a-3 |
| Br | F | Br | CF₃ | H | E-3b-1 |
| Br | F | Br | CF₃ | H | E-3b-2 |
| Br | F | Br | CF₃ | H | E-3b-3 |
| Br | F | Br | CF₃ | H | E-4a-1 |
| Br | F | Br | CF₃ | H | (E-5)Et |
| Br | F | Br | CF₃ | H | (E-6)CH₃ |
| Br | F | Br | CF₃ | H | (E-6)Et |
| Br | F | Br | CF₃ | H | (E-6)Bu-n |
| Br | F | Br | CF₃ | H | (E-6)CH₂CHF₂ |
| Br | F | Br | CF₃ | H | (E-6)CH₂CF₃ |
| Br | F | Br | CF₃ | H | (E-6)CH₂CH₂OCH₃ |
| Br | F | Br | CF₃ | H | (E-6)(T-1) |
| Br | F | Br | CF₃ | H | (E-6)CH₂C≡CH |
| Br | F | Br | CF₃ | H | CH₂(E-9)Et |
| Br | F | Br | CF₂Cl | H | E-3a-1 |
| Br | F | Br | CF₂Cl | H | E-3a-2 |

TABLE 1-continued

| | | | | | |
|---|---|---|---|---|---|
| Br | F | Br | CF$_2$Cl | H | E-3a-3 |
| Cl | Br | Cl | CF$_3$ | H | E-3a-1 |
| Cl | Br | Cl | CF$_3$ | H | E-3a-2 |
| Cl | Br | Cl | CF$_3$ | H | E-3a-3 |
| Br | Cl | Br | CF$_3$ | H | E-3a-1 |
| Br | Cl | Br | CF$_3$ | H | E-3a-2 |
| Br | Cl | Br | CF$_3$ | H | E-3a-3 |
| Br | Cl | Br | CF$_3$ | H | E-3b-1 |
| Br | Cl | Br | CF$_3$ | H | (E-6)Et |
| Br | Cl | Br | CF$_3$ | H | (E-6)CH$_2$CHF$_2$ |
| Br | Cl | Br | CF$_3$ | H | (E-6)CH$_2$CF$_3$ |
| Cl | Cl | CH$_3$ | CF$_3$ | H | E-3a-1 |
| Cl | Cl | CH$_3$ | CF$_3$ | H | E-3a-2 |
| Cl | Cl | CH$_3$ | CF$_3$ | H | E-3a-3 |
| CF$_3$ | F | F | CF$_3$ | H | E-3a-1 |
| CF$_3$ | F | F | CF$_3$ | H | E-3a-2 |
| CF$_3$ | F | F | CF$_3$ | H | E-3a-3 |
| CF$_3$ | F | F | CF$_3$ | H | E-3b-1 |
| CF$_3$ | F | F | CF$_3$ | H | (E-6)Et |
| CF$_3$ | F | F | CF$_3$ | H | (E-6)CH$_2$CHF$_2$ |
| CF$_3$ | F | F | CF$_3$ | H | (E-6)CH$_2$CF$_3$ |
| CF$_3$ | F | Cl | CF$_3$ | H | E-3a-1 |
| CF$_3$ | F | Cl | CF$_3$ | H | E-3a-2 |
| CF$_3$ | F | Cl | CF$_3$ | H | E-3a-3 |
| CF$_3$ | F | Cl | CF$_3$ | CH$_2$CN | E-3a-1 |
| CF$_3$ | F | Cl | CF$_3$ | CH$_2$CN | E-3a-2 |
| CF$_3$ | F | Cl | CF$_3$ | CH$_2$CN | E-3a-3 |
| CF$_3$ | F | Cl | CF$_3$ | C(O)CH$_3$ | E-3a-1 |
| CF$_3$ | F | Cl | CF$_3$ | C(O)CH$_3$ | E-3a-2 |
| CF$_3$ | F | Cl | CF$_3$ | C(O)CH$_3$ | E-3a-3 |
| CF$_3$ | F | Cl | CF$_3$ | C(O)Et | E-3a-1 |
| CF$_3$ | F | Cl | CF$_3$ | C(O)Et | E-3a-2 |
| CF$_3$ | F | Cl | CF$_3$ | C(O)Et | E-3a-3 |
| CF$_3$ | F | Cl | CF$_3$ | C(O)OCH$_3$ | E-3a-1 |
| CF$_3$ | F | Cl | CF$_3$ | C(O)OCH$_3$ | E-3a-2 |
| CF$_3$ | F | Cl | CF$_3$ | C(O)OCH$_3$ | E-3a-3 |
| CF$_3$ | F | Cl | CF$_3$ | H | E-3b-1 |
| CF$_3$ | F | Cl | CF$_3$ | H | (E-6)Et |
| CF$_3$ | F | Cl | CF$_3$ | H | (E-6)CH$_2$CHF$_2$ |
| CF$_3$ | F | Cl | CF$_3$ | H | (E-6)CH$_2$CF$_3$ |
| CF$_3$ | Cl | Cl | CF$_3$ | H | E-3a-1 |
| CF$_3$ | Cl | Cl | CF$_3$ | H | E-3a-2 |
| CF$_3$ | Cl | Cl | CF$_3$ | H | E-3a-3 |
| CF$_3$ | Cl | Cl | CF$_3$ | CH$_2$CN | E-3a-1 |
| CF$_3$ | Cl | Cl | CF$_3$ | CH$_2$CN | E-3a-2 |
| CF$_3$ | Cl | Cl | CF$_3$ | CH$_2$CN | E-3a-3 |
| CF$_3$ | Cl | Cl | CF$_3$ | C(O)CH$_3$ | E-3a-1 |
| CF$_3$ | Cl | Cl | CF$_3$ | C(O)CH$_3$ | E-3a-2 |
| CF$_3$ | Cl | Cl | CF$_3$ | C(O)CH$_3$ | E-3a-3 |
| CF$_3$ | Cl | Cl | CF$_3$ | C(O)Et | E-3a-1 |
| CF$_3$ | Cl | Cl | CF$_3$ | C(O)Et | E-3a-2 |
| CF$_3$ | Cl | Cl | CF$_3$ | C(O)Et | E-3a-3 |
| CF$_3$ | Cl | Cl | CF$_3$ | C(O)OCH$_3$ | E-3a-1 |
| CF$_3$ | Cl | Cl | CF$_3$ | C(O)OCH$_3$ | E-3a-2 |
| CF$_3$ | Cl | Cl | CF$_3$ | C(O)OCH$_3$ | E-3a-3 |
| CF$_3$ | Cl | Cl | CF$_3$ | H | E-3b-1 |
| CF$_3$ | Cl | Cl | CF$_3$ | H | (E-6)Et |
| CF$_3$ | Cl | Cl | CF$_3$ | H | (E-6)CH$_2$CHF$_2$ |
| CF$_3$ | Cl | Cl | CF$_3$ | H | (E-6)CH$_2$CF$_3$ |
| CF$_3$ | F | Br | CF$_3$ | H | E-3a-1 |
| CF$_3$ | F | Br | CF$_3$ | H | E-3a-2 |
| CF$_3$ | F | Br | CF$_3$ | H | E-3a-3 |
| CF$_3$ | F | Br | CF$_3$ | H | E-3b-1 |
| CF$_3$ | F | Br | CF$_3$ | H | (E-6)Et |
| CF$_3$ | F | Br | CF$_3$ | H | (E-6)CH$_2$CHF$_2$ |
| CF$_3$ | F | Br | CF$_3$ | H | (E-6)CH$_2$CF$_3$ |
| CF$_3$ | Cl | CF$_3$ | CF$_3$ | H | E-3a-1 |
| CF$_3$ | Cl | CF$_3$ | CF$_3$ | H | E-3a-2 |
| CF$_3$ | Cl | CF$_3$ | CF$_3$ | H | E-3a-3 |
| Cl | OCHF$_2$ | Cl | CF$_3$ | H | E-3a-1 |
| Cl | OCHF$_2$ | Cl | CF$_3$ | H | E-3a-2 |
| Cl | OCHF$_2$ | Cl | CF$_3$ | H | E-3a-3 |
| Cl | OCHF$_2$ | Cl | CF$_3$ | H | E-3b-1 |
| Cl | OCHF$_2$ | Cl | CF$_3$ | H | (E-6)Et |
| Cl | OCHF$_2$ | Cl | CF$_3$ | H | (E-6)CH$_2$CF$_3$ |
| Br | OCHF$_2$ | Br | CF$_3$ | H | E-3a-1 |
| Br | OCHF$_2$ | Br | CF$_3$ | H | E-3a-2 |
| Br | OCHF$_2$ | Br | CF$_3$ | H | E-3a-3 |
| Br | OCHF$_2$ | Br | CF$_3$ | H | E-3b-1 |
| Br | OCHF$_2$ | Br | CF$_3$ | H | (E-6)Et |
| Br | OCHF$_2$ | Br | CF$_3$ | H | (E-6)CH$_2$CF$_3$ |
| Cl | CN | Cl | CF$_3$ | H | E-3a-1 |
| Cl | CN | Cl | CF$_3$ | H | E-3a-2 |
| Cl | CN | Cl | CF$_3$ | H | E-3a-3 |

Table 2 shows the substituted benzamide compounds of formula (1) in which A$^1$ is nitrogen atom.

TABLE 2

[2]-1

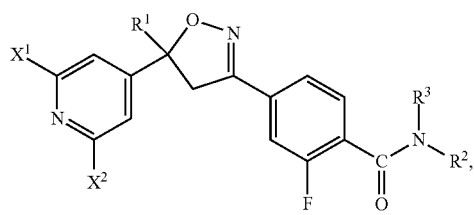

[2]-2

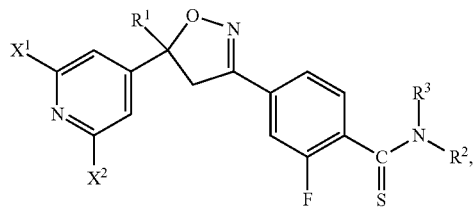

TABLE 2-continued
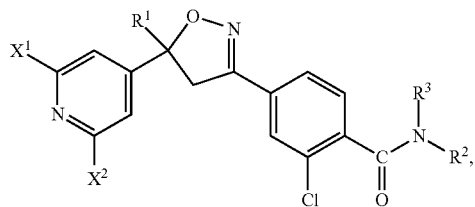
[2]-3
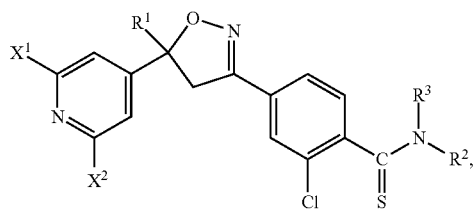
[2]-4
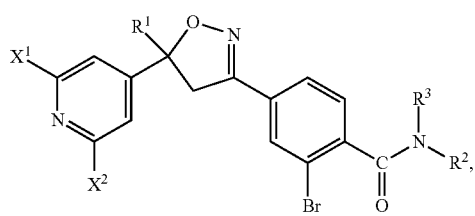
[2]-5
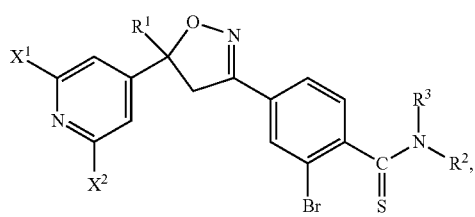
[2]-6
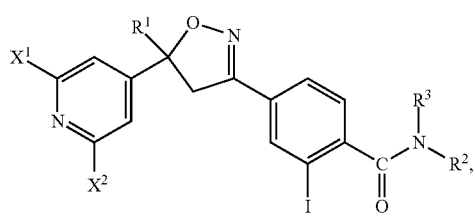
[2]-7
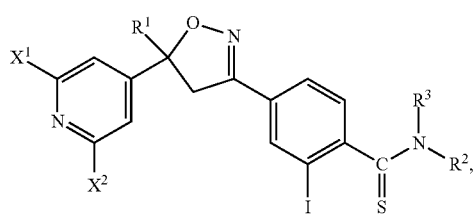
[2]-8

TABLE 2-continued
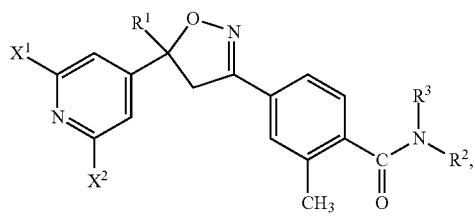
[2]-9
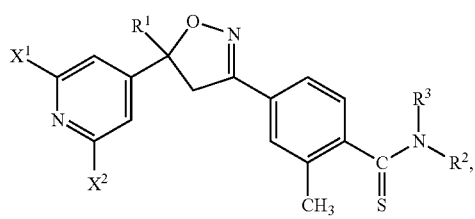
[2]-10
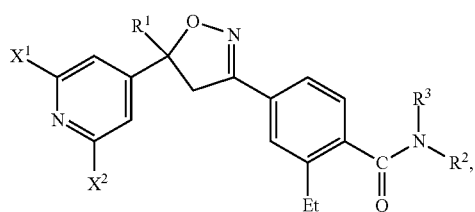
[2]-11
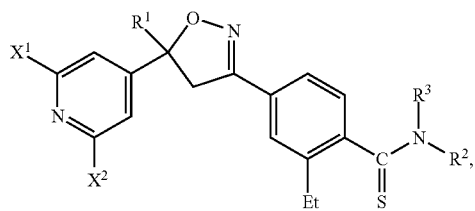
[2]-12
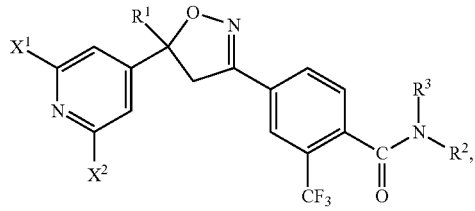
[2]-13
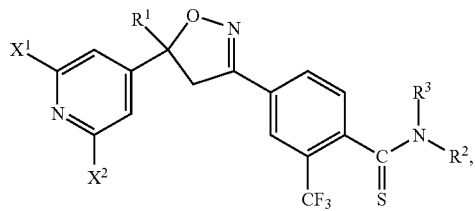
[2]-14

TABLE 2-continued
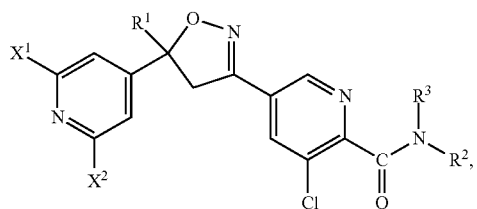
[2]-15
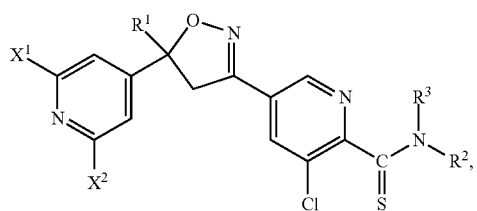
[2]-16
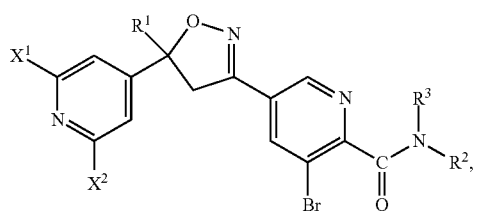
[2]-17
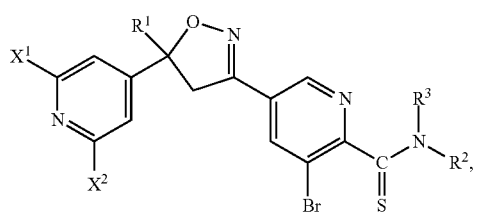
[2]-18
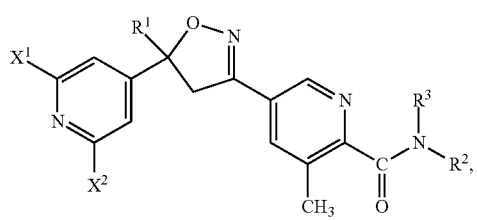
[2]-19
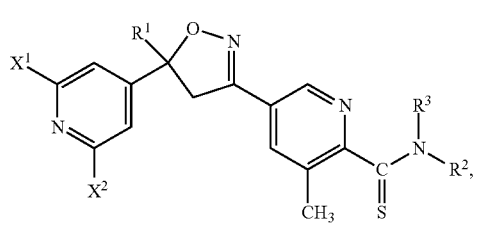
[2]-20

TABLE 2-continued
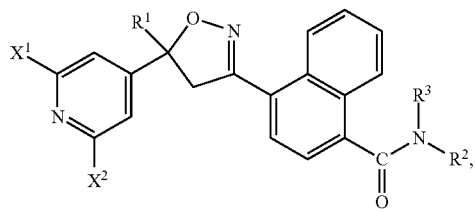
[2]-21
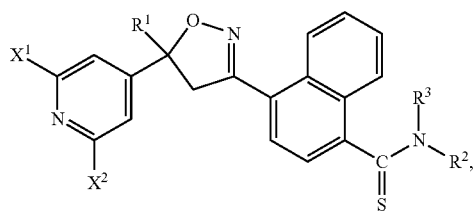
[2]-22
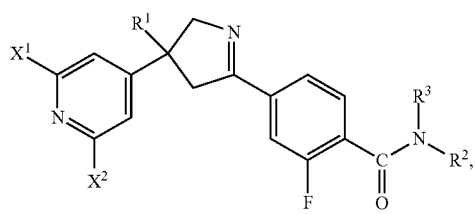
[2]-23
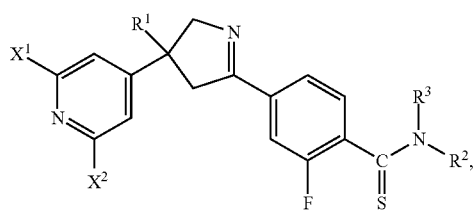
[2]-24
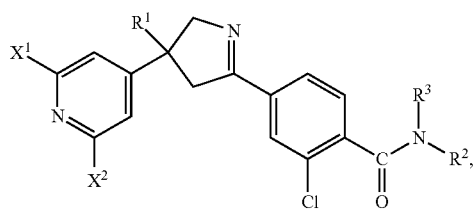
[2]-25
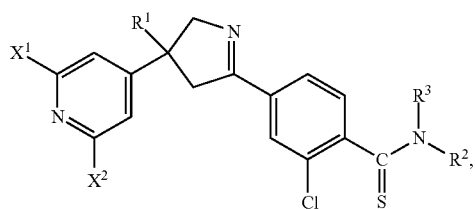
[2]-26

TABLE 2-continued
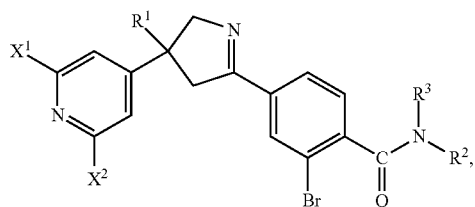
[2]-27
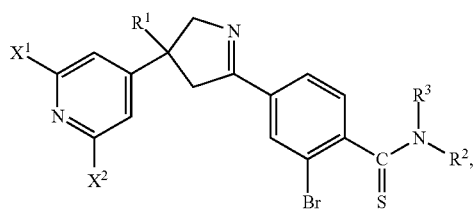
[2]-28
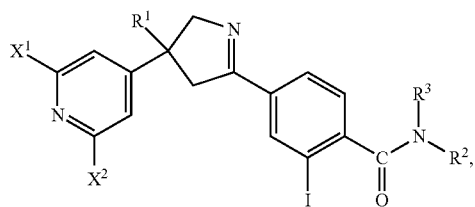
[2]-29
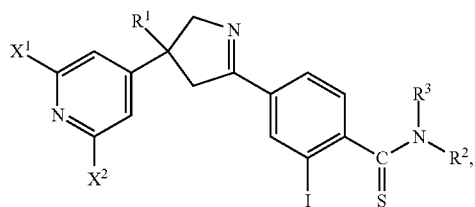
[2]-30
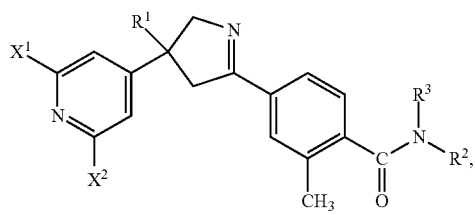
[2]-31
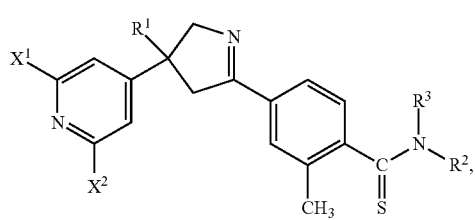
[2]-32

TABLE 2-continued
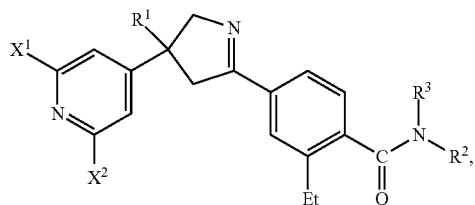
[2]-33
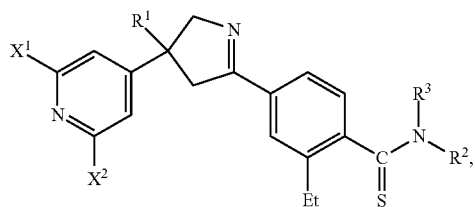
[2]-34
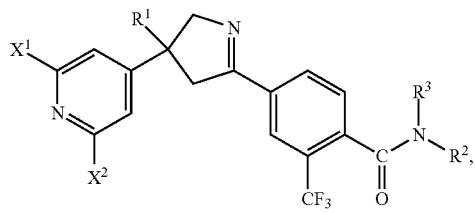
[2]-35
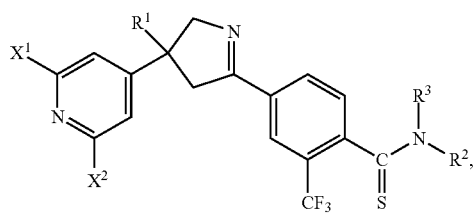
[2]-36
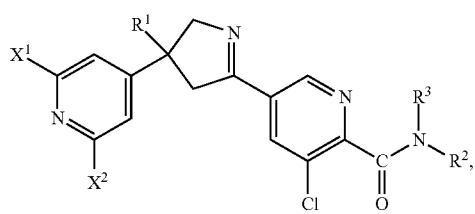
[2]-37
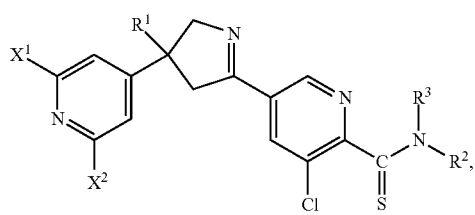
[2]-38

TABLE 2-continued
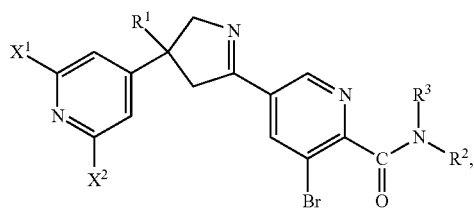
[2]-39
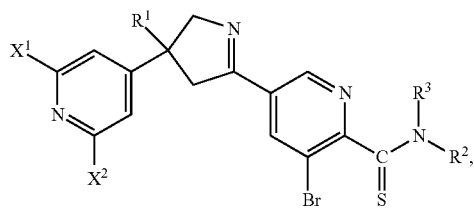
[2]-40
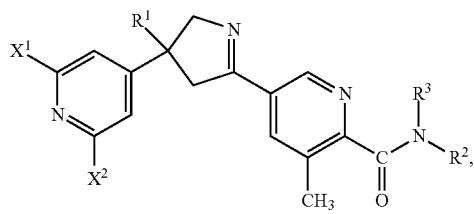
[2]-41
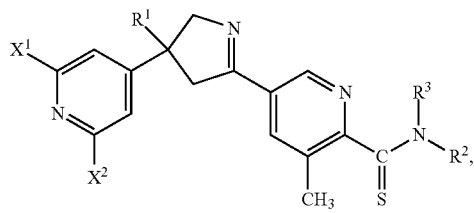
[2]-42
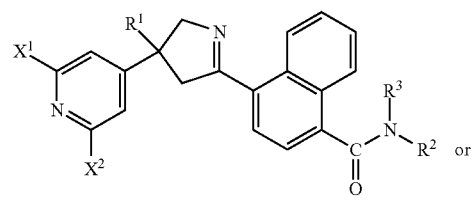
[2]-43
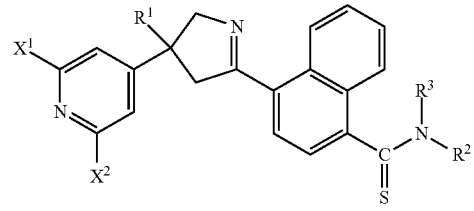
[2]-44
| $X^1$ | $X^2$ | $R^1$ | $R^3$ | $R^2$ |
|---|---|---|---|---|
| Cl | Cl | $CF_3$ | H | E-3a-1 |
| Cl | Cl | $CF_3$ | H | E-3a-2 |
| Cl | Cl | $CF_3$ | H | E-3a-3 |
| Cl | Cl | $CF_3$ | Et | E-3a-1 |
| Cl | Cl | $CF_3$ | Et | E-3a-2 |
| Cl | Cl | $CF_3$ | Et | E-3a-3 |
| Cl | Cl | $CF_3$ | $CH_2OCH_3$ | E-3a-1 |

TABLE 2-continued

| | | | | |
|---|---|---|---|---|
| Cl | Cl | CF₃ | CH₂OCH₃ | E-3a-2 |
| Cl | Cl | CF₃ | CH₂OCH₃ | E-3a-3 |
| Cl | Cl | CF₃ | CH₂CN | E-3a-1 |
| Cl | Cl | CF₃ | CH₂CN | E-3a-2 |
| Cl | Cl | CF₃ | CH₂CN | E-3a-3 |
| Cl | Cl | CF₃ | CH₂C≡CH | E-3a-1 |
| Cl | Cl | CF₃ | CH₂C≡CH | E-3a-2 |
| Cl | Cl | CF₃ | CH₂C≡CH | E-3a-3 |
| Cl | Cl | CF₃ | C(O)CH₃ | E-3a-1 |
| Cl | Cl | CF₃ | C(O)CH₃ | E-3a-2 |
| Cl | Cl | CF₃ | C(O)CH₃ | E-3a-3 |
| Cl | Cl | CF₃ | C(O)Et | E-3a-1 |
| Cl | Cl | CF₃ | C(O)Et | E-3a-2 |
| Cl | Cl | CF₃ | C(O)Et | E-3a-3 |
| Cl | Cl | CF₃ | C(O)Pr-c | E-3a-1 |
| Cl | Cl | CF₃ | C(O)Pr-c | E-3a-2 |
| Cl | Cl | CF₃ | C(O)Pr-c | E-3a-3 |
| Cl | Cl | CF₃ | C(O)Bu-t | E-3a-1 |
| Cl | Cl | CF₃ | C(O)Bu-t | E-3a-2 |
| Cl | Cl | CF₃ | C(O)Bu-t | E-3a-3 |
| Cl | Cl | CF₃ | C(O)CH₂OCH₃ | E-3a-1 |
| Cl | Cl | CF₃ | C(O)CH₂OCH₃ | E-3a-2 |
| Cl | Cl | CF₃ | C(O)CH₂OCH₃ | E-3a-3 |
| Cl | Cl | CF₃ | C(O)CH=CH₂ | E-3a-1 |
| Cl | Cl | CF₃ | C(O)CH=CH₂ | E-3a-2 |
| Cl | Cl | CF₃ | C(O)CH=CH₂ | E-3a-3 |
| Cl | Cl | CF₃ | C(O)OCH₃ | E-3a-1 |
| Cl | Cl | CF₃ | C(O)OCH₃ | E-3a-2 |
| Cl | Cl | CF₃ | C(O)OCH₃ | E-3a-3 |
| Cl | Cl | CF₃ | H | E-3b-1 |
| Cl | Cl | CF₃ | H | E-3b-2 |
| Cl | Cl | CF₃ | H | E-3b-3 |
| Cl | Cl | CF₃ | H | E-4a-1 |
| Cl | Cl | CF₃ | H | (E-5)Et |
| Cl | Cl | CF₃ | H | (E-6)CH₃ |
| Cl | Cl | CF₃ | H | (E-6)Et |
| Cl | Cl | CF₃ | H | (E-6)Bu-n |
| Cl | Cl | CF₃ | H | (E-6)CH₂CHF₂ |
| Cl | Cl | CF₃ | H | (E-6)CH₂CF₃ |
| Cl | Cl | CF₃ | H | (E-6)CH₂CH₂OCH₃ |
| Cl | Cl | CF₃ | H | (E-6)(T-1) |
| Cl | Cl | CF₃ | H | (E-6)CH₂C≡CH |
| Cl | Cl | CF₃ | H | CH₂(E-9)Et |
| Cl | Cl | CF₂Cl | H | E-3a-1 |
| Cl | Cl | CF₂Cl | H | E-3a-2 |
| Cl | Cl | CF₂Cl | H | E-3a-3 |
| CF₃ | CF₃ | CF₃ | H | E-3a-1 |
| CF₃ | CF₃ | CF₃ | H | E-3a-2 |
| CF₃ | CF₃ | CF₃ | H | E-3a-3 |
| CF₃ | CF₃ | CF₃ | CH₂CN | E-3a-1 |
| CF₃ | CF₃ | CF₃ | CH₂CN | E-3a-2 |
| CF₃ | CF₃ | CF₃ | CH₂CN | E-3a-3 |
| CF₃ | CF₃ | CF₃ | C(O)CH₃ | E-3a-1 |
| CF₃ | CF₃ | CF₃ | C(O)CH₃ | E-3a-2 |
| CF₃ | CF₃ | CF₃ | C(O)CH₃ | E-3a-3 |
| CF₃ | CF₃ | CF₃ | C(O)Et | E-3a-1 |
| CF₃ | CF₃ | CF₃ | C(O)Et | E-3a-2 |
| CF₃ | CF₃ | CF₃ | C(O)Et | E-3a-3 |
| CF₃ | CF₃ | CF₃ | C(O)OCH₃ | E-3a-1 |
| CF₃ | CF₃ | CF₃ | C(O)OCH₃ | E-3a-2 |
| CF₃ | CF₃ | CF₃ | C(O)OCH₃ | E-3a-3 |
| CF₃ | CF₃ | CF₃ | H | E-3b-1 |
| CF₃ | CF₃ | CF₃ | H | (E-6)Et |
| CF₃ | CF₃ | CF₃ | H | (E-6)CH₂CHF₂ |
| CF₃ | CF₃ | CF₃ | H | (E-6)CH₂CF₃ |

Table 3 shows the substituted benzamide compounds of formula (1) in which $A^1$ is $C—X^3$.
TABLE 3
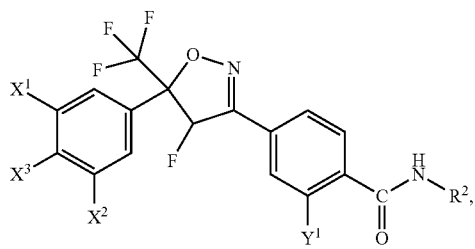
[3]-1
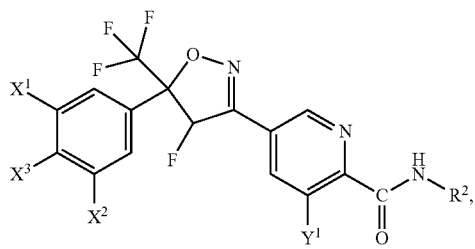
[3]-2
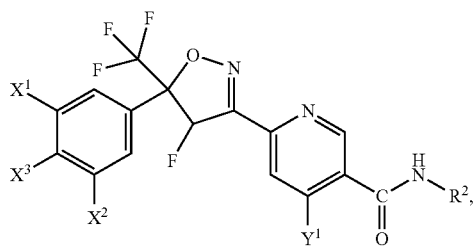
[3]-3
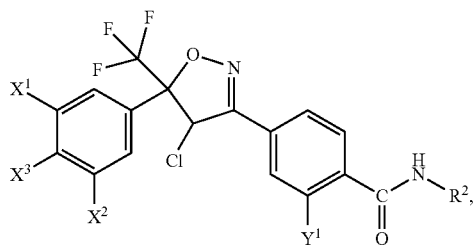
[3]-4
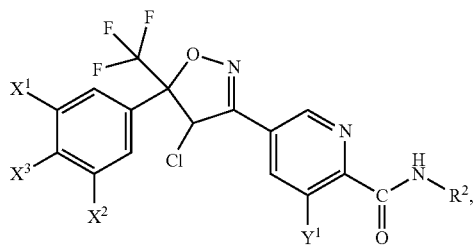
[3]-5

TABLE 3-continued
[3]-6
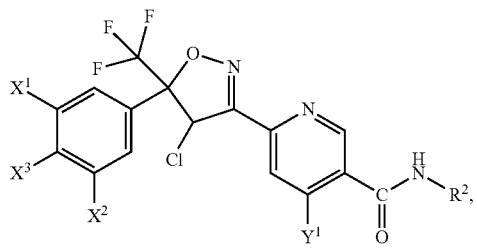
[3]-7
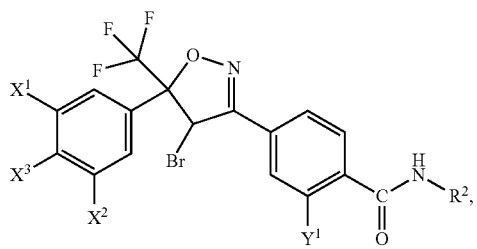
[3]-8
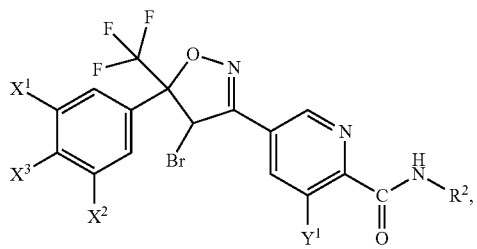
[3]-9
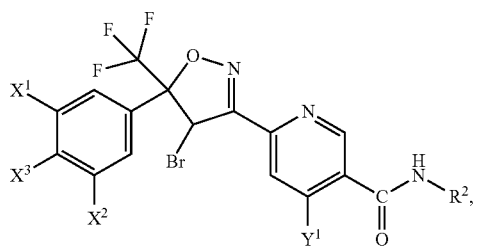
[3]-10
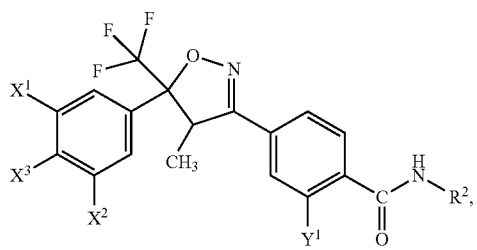

TABLE 3-continued
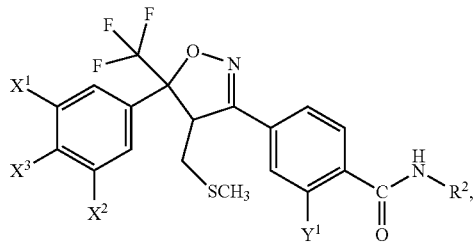
[3]-11
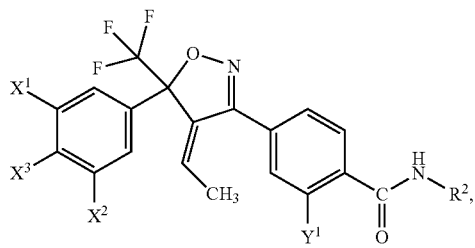
[3]-12
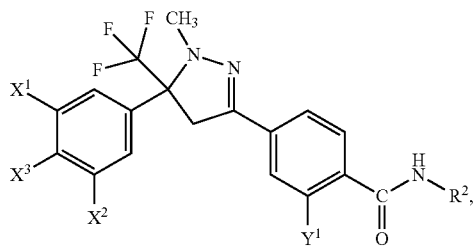
[3]-13
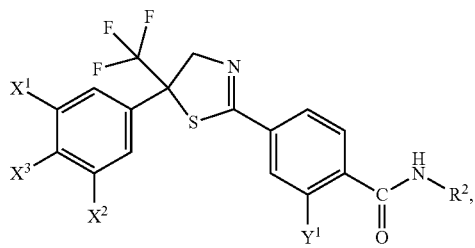
[3]-14
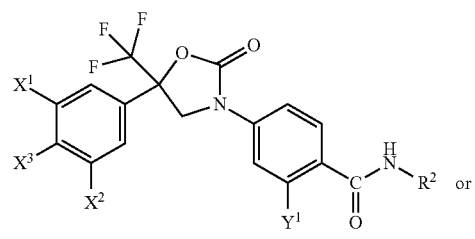
[3]-15
or
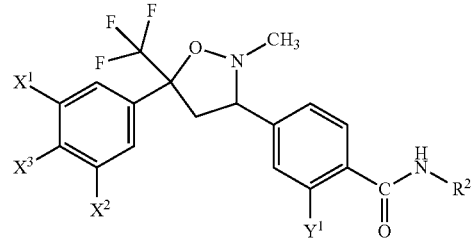
[3]-16

TABLE 3-continued

| $X^1$ | $X^3$ | $X^2$ | $Y^1$ | $R^2$ |
|---|---|---|---|---|
| Cl | H | F | CH$_3$ | E-3a-1 |
| Cl | H | F | CH$_3$ | E-3a-2 |
| Cl | H | F | CH$_3$ | E-3a-3 |
| Cl | H | Cl | Cl | E-3a-1 |
| Cl | H | Cl | Cl | E-3a-2 |
| Cl | H | Cl | Cl | E-3a-3 |
| Cl | H | Cl | Br | E-3a-1 |
| Cl | H | Cl | Br | E-3a-2 |
| Cl | H | Cl | Br | E-3a-3 |
| Cl | H | Cl | CH$_3$ | E-3a-1 |
| Cl | H | Cl | CH$_3$ | E-3a-2 |
| Cl | H | Cl | CH$_3$ | E-3a-3 |
| Cl | H | Cl | CH$_3$ | E-3b-1 |
| Cl | H | Cl | CH$_3$ | (E-6)Et |
| Cl | H | Cl | CH$_3$ | (E-6)CH$_2$CHF$_2$ |
| Cl | H | Cl | CH$_3$ | (E-6)CH$_2$CF$_3$ |
| Br | H | F | CH$_3$ | E-3a-1 |
| Br | H | F | CH$_3$ | E-3a-2 |
| Br | H | F | CH$_3$ | E-3a-3 |
| Br | H | Cl | CH$_3$ | E-3a-1 |
| Br | H | Cl | CH$_3$ | E-3a-2 |
| Br | H | Cl | CH$_3$ | E-3a-3 |
| Br | H | Cl | CH$_3$ | E-3b-1 |
| Br | H | Cl | CH$_3$ | (E-6)Et |
| Br | H | Cl | CH$_3$ | (E-6)CH$_2$CHF$_2$ |
| Br | H | Cl | CH$_3$ | (E-6)CH$_2$CF$_3$ |
| Br | H | Br | CH$_3$ | E-3a-1 |
| Br | H | Br | CH$_3$ | E-3a-2 |
| Br | H | Br | CH$_3$ | E-3a-3 |
| Br | H | Br | CH$_3$ | E-3b-1 |
| Br | H | Br | CH$_3$ | (E-6)Et |
| Br | H | Br | CH$_3$ | (E-6)CH$_2$CHF$_2$ |
| Br | H | Br | CH$_3$ | (E-6)CH$_2$CF$_3$ |
| I | H | Cl | CH$_3$ | E-3a-1 |
| I | H | Cl | CH$_3$ | E-3a-2 |
| I | H | Cl | CH$_3$ | E-3a-3 |
| CF$_3$ | H | F | CH$_3$ | E-3a-1 |
| CF$_3$ | H | F | CH$_3$ | E-3a-2 |
| CF$_3$ | H | F | CH$_3$ | E-3a-3 |
| CF$_3$ | H | Cl | Cl | E-3a-1 |
| CF$_3$ | H | Cl | Cl | E-3a-2 |
| CF$_3$ | H | Cl | Cl | E-3a-3 |
| CF$_3$ | H | Cl | Br | E-3a-1 |
| CF$_3$ | H | Cl | Br | E-3a-2 |
| CF$_3$ | H | Cl | Br | E-3a-3 |
| CF$_3$ | H | Cl | CH$_3$ | E-3a-1 |
| CF$_3$ | H | Cl | CH$_3$ | E-3a-2 |
| CF$_3$ | H | Cl | CH$_3$ | E-3a-3 |
| CF$_3$ | H | Cl | CH$_3$ | E-3b-1 |
| CF$_3$ | H | Cl | CH$_3$ | (E-6)Et |
| CF$_3$ | H | Cl | CH$_3$ | (E-6)CH$_2$CHF$_2$ |
| CF$_3$ | H | Cl | CH$_3$ | (E-6)CH$_2$CF$_3$ |
| CF$_3$ | H | Br | Cl | E-3a-1 |
| CF$_3$ | H | Br | Cl | E-3a-2 |
| CF$_3$ | H | Br | Cl | E-3a-3 |
| CF$_3$ | H | Br | Br | E-3a-1 |
| CF$_3$ | H | Br | Br | E-3a-2 |
| CF$_3$ | H | Br | Br | E-3a-3 |
| CF$_3$ | H | Br | CH$_3$ | E-3a-1 |
| CF$_3$ | H | Br | CH$_3$ | E-3a-2 |
| CF$_3$ | H | Br | CH$_3$ | E-3a-3 |
| CF$_3$ | H | Br | CH$_3$ | E-3b-1 |
| CF$_3$ | H | Br | CH$_3$ | (E-6)Et |
| CF$_3$ | H | Br | CH$_3$ | (E-6)CH$_2$CHF$_2$ |
| CF$_3$ | H | Br | CH$_3$ | (E-6)CH$_2$CF$_3$ |
| CF$_3$ | H | I | CH$_3$ | E-3a-1 |
| CF$_3$ | H | I | CH$_3$ | E-3a-2 |
| CF$_3$ | H | I | CH$_3$ | E-3a-3 |
| CF$_3$ | H | CF$_3$ | Cl | E-3a-1 |
| CF$_3$ | H | CF$_3$ | Cl | E-3a-2 |
| CF$_3$ | H | CF$_3$ | Cl | E-3a-3 |
| CF$_3$ | H | CF$_3$ | Br | E-3a-1 |
| CF$_3$ | H | CF$_3$ | Br | E-3a-2 |
| CF$_3$ | H | CF$_3$ | Br | E-3a-3 |
| CF$_3$ | H | CF$_3$ | CH$_3$ | E-3a-1 |
| CF$_3$ | H | CF$_3$ | CH$_3$ | E-3a-2 |
| CF$_3$ | H | CF$_3$ | CH$_3$ | E-3a-3 |

TABLE 3-continued

| | | | | |
|---|---|---|---|---|
| CF$_3$ | H | CF$_3$ | CH$_3$ | E-3b-1 |
| CF$_3$ | H | CF$_3$ | CH$_3$ | (E-6)Et |
| CF$_3$ | H | CF$_3$ | CH$_3$ | (E-6)CH$_2$CHF$_2$ |
| CF$_3$ | H | CF$_3$ | CH$_3$ | (E-6)CH$_2$CF$_3$ |
| Cl | H | SCF$_3$ | CH$_3$ | E-3a-1 |
| Cl | H | SCF$_3$ | CH$_3$ | E-3a-2 |
| Cl | H | SCF$_3$ | CH$_3$ | E-3a-3 |
| Cl | F | Cl | Cl | E-3a-1 |
| Cl | F | Cl | Cl | E-3a-2 |
| Cl | F | Cl | Cl | E-3a-3 |
| Cl | F | Cl | Br | E-3a-1 |
| Cl | F | Cl | Br | E-3a-2 |
| Cl | F | Cl | Br | E-3a-3 |
| Cl | F | Cl | CH$_3$ | E-3a-1 |
| Cl | F | Cl | CH$_3$ | E-3a-2 |
| Cl | F | Cl | CH$_3$ | E-3a-3 |
| Cl | F | Cl | CH$_3$ | E-3b-1 |
| Cl | F | Cl | CH$_3$ | (E-6)Et |
| Cl | F | Cl | CH$_3$ | (E-6)CH$_2$CHF$_2$ |
| Cl | F | Cl | CH$_3$ | (E-6)CH$_2$CF$_3$ |
| Cl | Cl | Cl | CH$_3$ | E-3a-1 |
| Cl | Cl | Cl | CH$_3$ | E-3a-2 |
| Cl | Cl | Cl | CH$_3$ | E-3a-3 |
| Br | F | Br | Cl | E-3a-1 |
| Br | F | Br | Cl | E-3a-2 |
| Br | F | Br | Cl | E-3a-3 |
| Br | F | Br | Br | E-3a-1 |
| Br | F | Br | Br | E-3a-2 |
| Br | F | Br | Br | E-3a-3 |
| Br | F | Br | CH$_3$ | E-3a-1 |
| Br | F | Br | CH$_3$ | E-3a-2 |
| Br | F | Br | CH$_3$ | E-3a-3 |
| Br | F | Br | CH$_3$ | E-3b-1 |
| Br | F | Br | CH$_3$ | (E-6)Et |
| Br | F | Br | CH$_3$ | (E-6)CH$_2$CHF$_2$ |
| Br | F | Br | CH$_3$ | (E-6)CH$_2$CF$_3$ |
| CF$_3$ | F | Cl | CH$_3$ | E-3a-1 |
| CF$_3$ | F | Cl | CH$_3$ | E-3a-2 |
| CF$_3$ | F | Cl | CH$_3$ | E-3a-3 |
| CF$_3$ | Cl | Cl | CH$_3$ | E-3a-1 |
| CF$_3$ | Cl | Cl | CH$_3$ | E-3a-2 |
| CF$_3$ | Cl | Cl | CH$_3$ | E-3a-3 |
| CF$_3$ | F | Br | CH$_3$ | E-3a-1 |
| CF$_3$ | F | Br | CH$_3$ | E-3a-2 |
| CF$_3$ | F | Br | CH$_3$ | E-3a-3 |

The parasite- and hygienic pest-controlling agent comprising as active ingredient containing the substituted benzamide compound of formula (I) or a salt thereof can effectively control arthropods as ecto-parasites or hygienic parasites of animals, or invertebrates such as nematodes, Acanthocephala, Cestoidea, Trematoda, Sporozoa, Ciliatea, Flagellata, or the like as endo-parasites of animals.

The animals for which the parasite-controlling agent of the present invention can be used in order to control harmful parasitic invertebrates concretely include for example Mammalia belonging to Cebidae such as tufted capuchin (*Cebus apella*), etc., Cercopithecidae such as crab-eating macaque (*Macaca fascicularis*), rhesus macaque (*Macaca mulatta*), etc., Homimidae such as chimpanzee (*Pan troglodytes*), human (*Homo sapiens*), etc., Leporidae such as European rabbit (*Oryctolagus cuniculus*), etc., Chinchillidae such as long-tailed chinchilla (*Chinchilla lanigera*), etc., Caviidae such as Guinea pig (*Cavia porcellus*), etc., Cricetidae such as golden hamster (*Mesocricetus auratus*), Djungarian hamster (*Phodopus sungorus*), Chinese hamster (*Cricetulus griseus*), etc., Muridae such as Mongolian gerbil (*Meriones unguiculatus*), house mouse (*Mus musculus*), black rat (*Rattus rattus*), etc., Sciuridae such as chipmunk (*Tamias sibiricus*), etc., Camelidae such as dromedary (*Camelus dromedarius*), Bactrian camel (*Camelus bactrianus*), alpaca (*Vicugna pacos*), llama (*Lama glama*), etc., Suidae such as pig (*Sus scrofa domesticus*), etc., Cervidae such as reindeer (*Rangifer tarandus*), Red deer (*Cervus elaphus*), etc., Bovidae such as yak (*Bos grunniens*), cattle (*Bos Taurus*), water buffalo (*Bubalus amee*), goat (*Capra hircus*), sheep (*Ovis aries*), etc., Felidae such as cat (*Felis silvestris catus*), etc., Canidae such as dog (*Canis lupus familiaris*), red fox (*Vulpes vulpes*), etc., Mustelidae such as European mink (*Mustela lutreola*), American mink (*Mustela vison*), ferret (*Mustela putorius furo*), etc., Equidae such as donkey (*Equus asinus*), horse (*Equus caballus*), etc., Macropodidae such as red kangaroo (*Macropus rufus*), etc.; Aves belonging to Struthionidae such as ostrich (*Struthio camelus*), etc., Rheidae such as American rhea (*Rhea americana*), etc., Dromaiidae such as emu (*Dromaius novaehollandiae*), etc., Phasianidae such as Ptarmigan (*Lagopus muta*), wild turkey (*Meleagris gallopavo*), Japanese quail (*Coturnix japonica*), chicken (*Gallus gallus domesticus*), common pheasant (*Phasianus colchicus*), golden pheasant (*Chrysolophus pictus*), Indian peafowl (*Pavo cristatus*), etc., Numididae such as helmeted guineafowl (*Numida meleagris*), etc., Anatidae such as mallard (*Anas platyrhynchos*), domesticated duck (*Anas platyrhynchos* var. *domesticus*), spot-billed duck (*Anas poecilorhyncha*), greylag goose (*Anser anser*), swan goose (*Anser cygnoides*), whooper swan (*Cygnus Cygnus*), mute swan (*Cygnus olor*), etc., Columbidae such as rock dove (*Columba livia*), oriental turtle dove (*Streptopelia* orientalis), European turtle dove (*Streptopelia turtur*), etc., Cacatuidae such as sulphur-crested cockatoo (*Cacatua galerita*), galah (*Eolophus roseicapilla*), cockatiel (*Nymphicus hollandicus*), etc., Psittacidae such as rosy-faced lovebird (*Agapornis roseicollis*), blue-and-yellow macaw (*Ara ararauna*), scarlet Macaw (*Ara macao*), budgerigar (*Melopsittacus undulatus*), African grey parrot (*Psittacus erithacus*), etc., Stumidae such as common hill myna (*Gracula religiosa*), etc., Estrildidae such as red avadavat (*Amandava amandava*), zebra finch (*Taeniopygia guttata*), Bengalese finch (*Lonchura striata* var. *domestica*), Java sparrow (*Padda oryzivora*), etc., Fringillidae such as domestic canary (*Serinus canaria domestica*), European goldfinch (*Carduelis carduelis*), etc.; Reptilia belonging to Chamaeleonidae such as veiled chameleon (*Chamaeleo calyptratus*), etc., Iguanidae such as green iguana (*Iguana iguana*), carolina anole (*Anolis carolinensis*), etc., Varanidae such as Nile monitor (*Varanus niloticus*), water monitor (*Varanus salvator*), etc., Scincidae such as Solomon islands skink (*Corucia zebrata*), etc., Colubridae such as beauty rat snake (*Elaphe taeniura*), etc., Boidae such as boa constrictor (*Boa constrictor*), etc., Pythonidae such as Indian python (*Python molurus*), reticulated python (*Python reticulates*), etc., Chelydridae such as common snapping turtle (*Chelydra serpentina*), etc., Emydidae such as diamondback terrapin (*Malaclemys terrapin*), pond slider (*Trachemys scripta*), etc., Geoemydidae such as Japanese pond turtle (*Mauremys japonica*), etc., Testudimidae such as Central Asian tortoise (*Agrionemys horsfieldii*), etc., Trionychidae such as soft-shelled turtle (*Pelodiscus sinensis*), etc., Alligatoridae such as American alligator (*Alligator mississippiensis*), black caiman (*Melanosuchus niger*), etc., Crocodylidae such as Siamese crocodile (*Crocodylus siamensis*), etc.; Actinopterygii belonging to Cyprimidae such as carp (*Cyprinus carpio*), goldfish (*Carassius auratus auratus*), zebrafish (*Danio rerio*), etc., Cobitidae such as Kuhli loach (*Pangio kuhlii*), etc., Characidae such as red piranha (*Pygocentrus nattereri*), neon tetra (*Paracheirodon innesi*), etc., Salmonidae such as Maraena whitefish (*Coregonus lavaretus maraena*), Coho salmon (*Oncorhynchus kisutsh*), rainbow trout (*Oncorhynchus mykiss*), Chinook salmon (*Oncorhynchus tshawytscha*), Atlantic salmon (*Salmo salar*), brown trout (*Salmo trutta*), etc., Percichthyidae such as spotted sea bass (*Lateolabrax maculatus*), etc., Serranidae such as sea goldie (*Pseudanthias squamipinnis*), longtooth grouper (*Epinephelus bruneus*), convict grouper (*Epinephelus septemfasciatus*), etc., Centrarchidae such as bluegill (*Lepomis macrochirus*), etc., Carangidae such as white trevally (*Pseudocaranx dentex*), greater amberjack (*Seriola dumerili*), Japanese amberjack (*Seriola quinqueradiata*), etc., Sparidae such as red sea bream (*Pagrus major*), etc., Cichlidae such as Nile tilapia (*Oreochromis niloticus*), angelfish (*Pterophyllum scalare*), etc., Scombridae such as Pacific bluefin tuna (*Thunnus orientalis*), etc., Tetraodontidae such as Japanese pufferfish (*Takifugu rubripes*), etc. The parasite-controlling agent of the present invention especially exerts excellent effects in extirpation of parasites parasitizing Mammalia belonging to Camelidae, Suidae, Bovidae, Felidae, Canidae and Equidae, and the like among the above-mentioned animals, and particularly shows outstanding effects in extirpation of ecto-parasites mammals of Felidae and Canidae, but to which targeted animals that parasitic invertebrates thereof can be expelled by use of the parasite-controlling agent of the present invention are not limited.

The harmful parasitic invertebrates and hygienic pests that can be expelled by use of the parasite- and hygienic pest-controlling agent of the present invention concretely include for example Hymenoptera such as Argentine ant (*Linepithema humile*), army ant (*Eciton burchelli, E. schmitti*), Japanese carpenter ant (*Camponotus japonicus*), Pharaoh ant (*Monomorium pharaonis*), bulldog ant (*Myrmecia* spp.), fire ant (*Solenopsis* spp.), Asian giant hornet (*Vespa mandarina*), Japanese yellow hornet (*Vespa simillima*), etc., Diptera such as tsetse fly (*Glossina morsitans, G. palpalis*), forest fly (*Hippobosca equina*), sheep ked (*Melophagus ovinus*), lesser house fly (*Fannia canicularis*), sheep headfly (*Hydrotaea irritans*), sweat fly (*Morellia simplex*), face fly (*Musca autumnalis*), housefly (*Musca domestica*), Australian bush fly (*Musca vetustissima*), horn fly (*Haematobia irritans*), stable fly (*Stomoxys calcitrans*), *Calliphora lata*, bottle fly (*Calliphora vicina*), old world screw-worm fly (*Chrysomya bezziana*), blow fly (*Chrysomya chloropyga*), Oriental latrine fly (*Chrysomya megacephala*), new world screw-worm fly (*Cochliomyia hominivorax*), black blow fly (*Phormia regina*), Northern blowfly (*Protophormia terraenovae*), Australian sheep blowfly (*Lucilia cuprina*), green bottle fly (*Lucilia illustris*), common green bottle fly (*Lucilia sericata*), bot flies (*Cuterebra* spp.), human botfly (*Dermatobia hominis*), horse nose bot fly (*Gasterophilus haemorrhoidalis*), horse bot fly (*Gasterophilus intestinalis*), throat bot fly (*Gasterophilus nasalis*), warble fly (*Hypoderma bovis*), common cattle grub (*Hypoderma lineatum*), sheep nasal bot fly (*Oestrus ovis*), flesh fly (*Sarcophaga carnaria*), flesh fly (*Sarcophaga peregrina*), splayed deerfly (*Chrysops caecutiens*), deer fly (*Chrysops suavis*), common horse fly (*Haematopota pluvialis*), Greenhead horse fly (*Tabanus nigrovittatus*), horse fly (*Tabanus trigonus*), biting midge (*Culicoides arakawae*), black gnat (*Leptoconops nipponensis*), *Prosimulium yezoensis*, black fly (*Simulium ochraceum*), African malaria mosquito (*Anopheles gambiae*), *Anopheles hyrcanus sinesis, Anopheles lesteri*, yellow fever mosquito (*Aedes aegypti*), Asian tiger mosquito (*Aedes albopictus*), house mosquito (*Culex pipiens molestus*), house mosquito (*Culex pipiens pallens, Culex tritaeniorhynchus*, moth fly (*Telmatoscopus albipunctatus*), etc., Siphonaptera such as hen flea (*Ceratophyllus gallinae*), chigoe flea (*Tunga penetrans*), dog flea (*Ctenocephalides canis*), cat flea (*Ctenocephalides felis*), sticktight flea (*Echidnophaga gallinacea*), human flea (*Pulex irritans*), Oriental rat flea (*Xenopsylla cheopis*), etc., Hemiptera such as bed bug (*Cimex lectularius*), blood-sucking bug (*Rhodnius prolixus*), kissing bug (*Triatoma dimidiata*), kissing bug (*Triatoma infestans*), etc., Psocodea such as body louse (*Menacanthus comutus*), small body louse (*Menacanthus pallidulus*), chicken body louse (*Menacanthus stramineus*), chicken shaft louse (*Menopon gallinae*), chicken head louse (*Cuclotogaster heterographa*), brown chicken louse (*Goniodes dissmilis*), fluff louse (*Goniodes gallinae*), large hen louse (*Goniodes gigas*), wing louse (*Lipeurus caponis*), cattle chewing louse (*Damalinia bovis*), cat louse (*Felicola subrostrata*), dog biting louse (*Trichodectes canis*), short-nosed cattle louse (*Haematopinus eurysternus*), tail switch louse (*Haematopinus quadripertusus*), large pig louse (*Haematopinus suis*), buffalo louse (*Haematopinus tuberculatus*), dog sucking louse (*Linognathus setosus*), long-nosed cattle louse (*Linognathus vituri*), rabbit louse (*Haemodipsus ventricosus*), little blue cattle louse (*Solenopotes capillatus*), head louse (*Pediculus humanus*), mouse louse (*Polyplax serratus*), crab louse (*Pthirus pubis*), etc., Blattaria such as German cockroach (*Blattella germanica*), American cockroach (*Periplaneta americana*), smokybrown cockroach (*Periplaneta fuliginosa*), Japanese cockroach (*Periplaneta japonica*), etc., Isoptera such as Daikoku dry-wood termite (*Cryptotermes domesticus*), western dry-wood termite (*Incisitermes minor*), formosan subterranean termite (*Coptotermes formosanus*), Japanese subterranean termite (*Reticulitermes speratus*), black-winged subterranean termite (*Odontotermes formosanus*), etc., Arguloida such as *Argulus coregoni*, Japanese fishlouse (*Argulus japonicus*), *Argulus scutiformis*, etc., Siphonostomatoida such as sea louse (*Caligus curtus, C. elongates*), salmon louse (*Lepeophtheirus salmonis*), etc., Isopoda such as pill bug (*Armadillidium vulgare*), common rough woodlouse (*Porcellio scaber*), etc., Astigmata such as storage mite (*Glycyphagus destructor*), house itch mite (*Glycyphagus domesticus*), cheese mite (*Tyrophagus putrescentiae*), feather mite (*Pterolichus obtusus*), feather mite (*Megninia cubitalis*), American house dust mite (*Dermatophagoides farinae*), house dust mite (*Dermatophagoides pteronyssinus*), chorioptic mange mite (*Chorioptes bovis*), dog ear mite (*Otodectes cynotis*), psoroptic mite (*Psoroptes communis*), rabbit ear mite (*Psoroptes cuniculi*), sheep scab mite (*Psoroptes ovis*), itch mite (*Sarcoptes scabiei*), cat mange mite (*Notoedres cati*), etc., Oribatida such as *Haplochthonius simplex*, etc., Prostigmata such as *Chelacaropsis moorei*, *Cheyletiella blakei*, rabbit fur mite (*Cheyletiella parasitovorax*), *Cheyletiella yasguri, Cheyletus eruditus, Cheyletus malaccensis*, dog follicle mite (*Demodex canis*), cat follicle mite (*Demodex cati*), face mite (*Demodex folliculorum*), *Eutrombicula wichmanni*, trombiculid mite (*Helenicula miyagawai*), *Leptotrombidium akamushi, Leptotrombidium pallida*, tsutsugamushi mite (*Leptotrombidium scutellare*), etc., Metastigmata such as English fowl tick (*Argas persicus*), soft tick (*Ornithodoros moubata*), relapsing fever tick (*Ornithodoros turicata*), spinose ear tick (*Otobius megnini*), lone star tick (*Amblyomma americanum*), gulf coast tick (*Amblyomma maculatum*), *Haemaphysalis campanulata, Haemaphysalis flava*, bush tick (*Haemaphysalis longicomis*), *Haemaphysalis megaspinosa*, tortoise tick (*Hyalomma aegyptium*), Mediterranean tick (*Hyalomma marginatum*), tropical cattle tick (*Boophilus microplus*), *Ixodes nipponensis, Ixodes ovatus*, western black-legged tick (*Ixodes pacifcus*), taiga tick (*Ixodes persulcatus*), castor bean tick (*Ixodes ricinus*), black-legged tick (*Ixodes scapularis*), tropical horse tick (*Anocentor nitens*), Rocky Mountain wood tick (*Dermacentor andersoni*), Pacific Coast tick (*Dermacentor occidentalis*), ornate cow tick (*Dermacentor reticulatus*), American dog tick (*Dermacentor variabilis*), *Rhipicentor* spp., American cattle tick (*Rhipicephalus annulatus*), brown dog tick (*Rhipicephalus sanguineus*), etc., Mesostigmata such as red mite (*Dermanyssus gallinae*), tropical rat mite (*Ornithonyssus bacoti*), northern fowl mite (*Ornithonyssus sylviarum*), etc., Stylommatophora such as terrestrial slug (*Limax marginatus*), slug (*Meghimatium bilineatum*), etc., Enoplida such as giant kidney worm (*Dioctophyma renale*), thread worms (*Capillaria annulata*), cropworm (*Capillaria contorta*), capillary liver worm (*Capillaria hepatica*), *Capillaria perforans, Capillaria philippinensis, Capillaria suis*, whipworm (*Trichuris discolor*), whipworm (*Trichuris ovis*), pig whipworm (*Trichuris suis*), human whipworm (*Trichuris trichiura*), dog whipworm (*Trichuris vulpis*), pork worm (*Trichinella spiralis*), etc., Rhabditida such as intestinal threadworm (*Strongyloides papillosus*), *Strongyloides planiceps*, pig threadworm (*Strongyloides ransomi*), threadworm (*Strongyloides stercoralis*), *Micronema* spp., etc., Strongylida such as hookworm (*Ancylostoma braziliense*), dog hookworm (*Ancylostoma caninum*), Old World hookworm (*Ancylostoma duodenale*), cat hookworm (*Ancylostoma tubaeforme*), The Northern hookworm of dogs (*Uncinaria stenocephala*), cattle hookworm (*Bunostomum phlebotomum*), small ruminant hookworm (*Bunostomum trigonocephalum*), New World hookworm (*Necator americanus*), *Cyathostomum* spp., *Cylicocyclus* spp., *Cylicodontophorus* spp., *Cylicostephanus* spp., *Strongylus asini, Strongylus edentatus*, blood worm (*Strongylus equinus*), blood worm (*Strongylus vulgaris*), large-mouthed bowel worm (*Chabertia ovina*), nodular worm (*Oesophagostomum brevicaudatum*), nodule worm (*Oesophagostomum columbianum*), nodule worm (*Oesophagostomum dentatum*), nodular worm (*Oesophagostomum georgianum*), nodular worm (*Oesophagostomum maplestonei*), nodular worm (*Oesophagostomum quadrispinulatum*), nodular worm (*Oesophagostomum radiatum*), nodular worm (*Oesophagostomum venulosum*), *Syngamus skrjabinomorpha*, gapeworm (*Syngamus trachea*), swine kidney worm (*Stephanurus dentatus*), cattle bankrupt worm (*Cooperia oncophora*), red stomach worm (*Hyostrongylus rubidus*), stomach hair worm (*Trichostrongylus axei*), *Trichostrongylus colubriformis*, Oriental trichostrongylus (*Trichostrongylus orientalis*), red stomach worm (*Haemonchus contortus*), cattle stomach worm (*Mecistocirrus digitatus*), brown stomach worm (*Ostertagia ostertagi*), common lungworm (*Dictyocaulus filarial*), bovine lungworm (*Dictyocaulus viviparous*), thin-necked intestinal worm (*Nematodirus filicollis*), swine lungworm (*Metastrongylus elongatus*), lungworm (*Filaroides hirthi*), lungworm (*Crenosoma aerophila*), fox lungworm (*Crenosoma vulpis*), rat lung worm (*Angiostrongylus cantonensis*), French heartworm (*Angiostrongylus vasorum*), *Protostrongylus* spp., etc., Oxyurida such as pinworm (*Enterobius vermicularis*), equine pinworm (*Oxyuris equi*), rabbit pinworm (*Passalurus ambiguus*), etc., Ascaridida such as pig roundworm (*Ascaris suum*), horse roundworm (*Parascaris equorum*), dog roundworm (*Toxascaris leonina*), dog intestinal roundworm (*Toxocara canis*), feline roundworm (*Toxocara cati*), large cattle roundworm (*Toxocara vitulorum*), *Anisakis* spp., *Pseudoterranova* spp., caecal worm (*Heterakis gallinarum*), chicken roundworm (*Ascaridia galli*), etc., Spirurida such as Guinea worm (*Dracunculus medinensis*), *Gnathostoma doloresi*, *Gnathostoma hispidum*, *Gnathostoma nipponicum*, reddish-coloured worm (*Gnathostoma spinigerum*), dog stomach worm (*Physaloptera canis*), cat stomach worm (*Physaloptera felidis, P. praeputialis*), feline/canine stomach worm (*Physaloptera rara*), eye worm (*Thelazia callipaeda*), bovine eyeworm (*Thelazia rhodesi*), large mouth stomach worm (*Draschia megastoma*), equine stomach worm (*Habronema microstoma*), stomach worm (*Habronema muscae*), gullet worm (*Gongylonema pulchrum*), thick stomach worm (*Ascarops strongylina*), parafilaria (*Parafilaria bovicola*), *Parafilaria multipapillosa, Stephanofilaria okinawaensis*, bancroft filaria (*Wuchereria bancrofti*), *Brugia malayi*, neck threadworm (*Onchocerca cervicalis*), *Onchocerca gibsoni*, cattle filarial worm (*Onchocerca gutturosa*), *Onchocerca volvulus*, bovine filarial worm (*Setaria digitata*), peritoneal worm (*Setaria equina*), *Setaria labiato-* papillosa, Setaria marshalli, dog heartworm (Dirofilaria immitis), African eye worm (Loa loa), etc., Acanthocephala such as Moniliformis moniliformis, giant thorny-headed worm (Macracanthorhynchus hirudinaceus), etc., Pseudophyllidea such as fish tapeworm (Diphyllobothrium latum), Diphyllobothrium nihonkaiense, manson tapeworm (Spirometra erinaceieuropaei), Diplogonoporus grandis, etc., Cyclophyllidea such as Mesocestoides lineatus, chicken tapeworm (Raillietina cesticillus), fowl tapeworm (Raillietina echinobothrida), chicken tapeworm (Raillietina tetragona), canine tapeworm (Taenia hydatigena), canine tapeworm (Taenia multiceps), sheep measles (Taenia ovis), dog tapeworm (Taenia pisiformis), beef tapeworm (Taenia saginata), tapeworm (Taenia serialis), pork tapeworm (Taenia solium), feline tapeworm (Taenia taeniaeformis), hydatid tapeworm (Echinococcus granulosus), small fox tapeworm (Echinococcus multilocularis), Echinococcus oligarthrus, Echinococcus vogeli, rat tapeworm (Hymenolepis diminuta), dwarf tapeworm (Hymenolepis nana), double-pored dog tapeworm (Dipylidium caninum), Amoebotaenia sphenoides, Choanotaenia infundibulum, Metroliasthes coturnix, equine tapeworm (Anoplocephala magna), cecal tapeworm (Anoplocephala perfoliata), dwarf equine tapeworm (Paranoplocephala mamillana), common tapeworm (Moniezia benedeni), sheep tapeworm (Moniezia expansa), Stilesia spp., etc., Strigeidida such as Pharyngostomum cordatum, blood fluke (Schistosoma haematobium), blood fluke (Schistosoma japonicum), blood fluke (Schistosoma mansoni), etc., Echinostomida such as Echinostoma cinetorchis, Echinostoma hortense, giant liver fluke (Fasciola gigantica), common liver fluke (Fasciola hepatica), Fasciolopsis buski, Homalogaster paloniae, etc., Plagiorchiida such as Dicrocoelium chinensis, lancet liver fluke (Dicrocoelium dendriticum), African lancet fluke (Dicrocoelium hospes), Eurytrema coelomaticum, pancreatic fluke (Eurytrema pancreaticum), Paragonimus miyazakii, Paragonimus ohirai, lung fluke (Paragonimus westermani), etc., Opisthorchiida such as Amphimerus spp., Chinese liver fluke (Clonorchis sinensis), cat liver fluke (Opisthorchis felineus), Southeast Aasian liver fluke (Opisthorchis viverrini), Pseudamphistomum spp., Metorchis spp., Parametorchis spp., intestinal fluke (Heterophyes heterophyes), Metagonimus yokokawai, Pygidiopsis summa, etc., Amoebozoa such as Entamoeba histolytica, E. invadens, etc., Piroplasmida such as Babesia bigemina, Babesia bovis, Babesia caballi, Babesia canis, Babesia felis, Babesia gibsoni, Babesia ovata, Cytauxzoon felis, Theileria annulata, Theileria mutans, Theileria orientalis, Theileria parva, etc., Haemosporida such as Haemoproteus mansoni, Leucocytozoon caulleryi, Plasmodium falciparum, Plasmodium malariae, Plasmodium ovale, Plasmodium vivax, etc., Eucoccidiorida such as Caryospora spp., Eimeria acervulina, Eimeria bovis, Eimeria brunetti, Eimeria maxima, Eimeria necatrix, Eimeria ovinoidalis, Eimeria stiedae, Eimeria tenella, Isospora canis, Isospora felis, Isospora suis, Tyzzeria alleni, Tyzzeria anseris, Tyzzeria perniciosa, Wenyonella anatis, Wenyonella gagari, Cryptosporidium canis, Cryptosporidium felis, Cryptosporidium hominis, Cryptosporidium meleagridis, Cryptosporidium muris, Cryptosporidium parvum, Sarcocystis canis, Sarcocystis cruzi, Sarcocystis felis, Sarcocystis hominis, Sarcocystis miescheriana, Sarcocystis neurona, Sarcocystis tenella, Sarcocystis ovalis, Toxoplasma gondii, Hepatozoon canis, Hepatozoon felis, etc., Vestibuliferida such as Balantidium coli, etc., Trichomonadida such as Histomanas meleagridis, Pentatrichomonas hominis, Trichomonas tenax, etc., Diplomonadida such as Giardia intestinalis, Giardia muris, Hexamita meleagridis, Hexamita parva, etc., Kinetoplastida such as Leishmania donovani, Leishmania infantum, Leishmania major, Leishmania tropica, Trypanosoma brucei gambiense, Trypanosoma brucei rhodesiense, Trypanosoma cruzi, Trypanosoma equiperdum, Trypanosoma evansi, etc.

The parasite- and hygienic pest-controlling agent of the present invention especially exerts excellent effects in extirpation of arthropods as ecto-parasites and hygienic pests belonging to Hymenoptera, Diptera, Siphonaptera, Hemiptera, Psocodea, Blattaria, Isoptera, Arguloida, Siphonostomatoida, Isopoda, Astigmata, Oribatida, Prostigmata, Metastigmata, Mesostigmata, and the like among the above-mentioned parasites and hygienic peste, and particularly shows outstanding effects for Diptera such as fly, mosquito or the like, Siphonaptera such as dog flea, cat flea or the like, Astigmata, Prostigmata, Metastigmata, but to which harmful invertebrates are expelled by the parasite- and hygienic pest-controlling agent of the present invention are not limited.

When the parasite- and hygienic pest-controlling agents of the present invention are used for expelling these harmful invertebrates, the substituted benzamide compounds of formula (1) or the salts thereof that are the active ingredient, or mixtures of one or more selected from them can be used as such, but generally can be mixed with a suitable solid carrier or liquid carrier, optionally along with surfactant, penetrating agent, spreading agent, thickner, anti-freezing agent, binder, anti-caking agent, disintegrating agent, anti-foaming agent, preservative, stabilizer, and the like, and can be formulated into arbitrary forms suitable for administration route, such as soluble concentrates, emulsifiable concentrates, wettable powders, water soluble powders, water dispersible granules, water soluble granules, suspension concentrates, concentrated emulsions, suspoemulsions, microemulsions, dustable powders, granules, tablets and emulsifiable gels, etc.

When the parasite- and hygienic pest-controlling agents of the present invention are used as the parasite-controlling agents, the substituted benzamide compounds of formula (1) or the salts thereof that are the active ingredient, or mixtures of one or more selected from them can effectively expel harmful parasitic invertebrates by formulating with a carrier consisting of one or more excipients that are pharmaceutically or veterinarily acceptable, and auxiliary substances that are suitable for administration route to obtain parasite-controlling agent compositions, and directly administering the compositions to animals to be protected or spraying the compositions to animal's breeding environment such as animal housing or the like.

When the parasite-controlling agent of the present invention is directly administered to animals to be protected, it can be administered through oral administration, parenteral administration or an administration with a formed product. The parenteral administration includes for example transdermal administration such as bathing or dipping, shampooing, spraying, pouring-on, spotting-on, and dusting, or the like, administration through injection such as subcutaneous injection, intramuscular injection, intraperitoneal injection or intravenous injection or the like, administratin by inplants or the like, transnasal administration and suppository administration, or the like. The administration by the formed products includes administration by use of labelling apparatuses such as neck collars, halters, tail bands, limb bands and ear tags, etc. Among these administration methods, oral administration and transdermal administration such as bathing or dipping, pouring-on, spotting-on, or the like are particularly preferable as the administration method of the parasite-controlling agent of the present invention, but to which the administration method in the present invention is not limited.

When harmful parasitic invertebrates are expelled by use of the parasite-controlling agent of the present invention, preferable dose of the substituted benzamide compounds of formula (1) or the salts thereof that are the active ingredient may vary depending on the kind of the taget parasites to be controlled, the kind of animals to be administered or administration method, or the like, and in general, it is 0.01 to 100 mg/kg, preferably 0.01 to 50 mg/kg based on the body weight of animals to be administered.

When harmful parasitic invertebrates are expelled by administering the parasite-controlling agent of the present invention, administration interval may vary depending on the kind of the taget parasites to be controlled, the kind of animals to be administered or administration method, or the like, and in general, it is arbitrarily set to range from every day to one time per year, preferably from one time per week to one time per 6-month, more preferably one time per month to one time per 3-month.

The dosage form in case where the parasite-controlling agent of the present invention is orally administered includes for example solid preparations such as tablets, cheables, capsules, pills, boluses, granules, powders, etc., semi-solid preparations such as pastes, gels, etc., liquid preparations such as drinks, etc. The dosage form in case of transdermal administration includes for example solid preparations such as powders, etc., semi-solid preparations such as cream, salve and ointment, pastes, gels, etc., liquid preparations such as spray, aerosols, solutions and emulsions, suspensions, lotions, etc. The dosage form in case of administration through injections includes for example liquid preparations such as solutions and emulsions, suspensions, etc. The dosage form in case of transnasal administration includes for example liquid preparations such as aerosols, etc. The dosage form in case of spray-treatment of animal's breeding environment such as animal housing, etc. includes for example solid preparations such as wettable powders, dusts, granules, etc., liquid preparations such as emulsions, suspension concentrates, etc. However, the formulations used for the parasite-controlling agent of the present invention are not limited to these dosage forms.

The solid preparations can be used by orally administering as such, or by diluting with water and then transdermally administering it or spraying it to animal's breeding environment such as animal housing or the like.

The solid preparations used for oral administration can be prepared by mixing the substituted benzamide compounds of formula (1) or the salts thereof with one or more excipients and binders that sre suitable for oral administration, and further if necessary physiologically acceptable additives such as lubricants, disintegrating agents, dyes and pigments, etc., and forming into desired forms. The excipients and binders include for example saccharide or saccharide derivatives such as lactose, sucrose, mannitol, sorbitol, etc., starch such as corn starch, wheat starch, rice starch, potato starch, etc., cellulose or cellulose derivatives such as methyl cellulose, carboxymethyl cellulose, hydroxyethyl cellulose, hydroxypropyl cellulose, hydroxypropyl methyl cellulose, etc., proteins or protein derivatives such as sein, gelatin, etc., honey, gum arabic, synthetic polymers such as polyvinyl alcohol, poly(vinyl pyrrolidone), and the like. The lubricants include for example magnesium stearate, and the like. The disintegrating agents include for example cellulose, agar, alginic acid, crosslinked poly(vinyl pyrrolidinone), carbonates, and the like. Particularly, in the solid dosages such as chewables among the solid preparations used for oral administration, additives conferring taste, texture, flavor that animals to which the preparations are administered like are used. However, the carriers and additives used for the solid preparations of the parasite-controlling agent composition of the present invention are not limited to the above-mentioned ones.

The liquid preparations can be used by administering as such through transdermal or injection route, or by orally administering a mixture with feed, or by diluting with water and then transdermally administering it or spraying it to animal's breeding environment such as animal housing or the like.

The liquid preparations such as solutions and emulsions, suspensions, etc., that are used in the form of pour-on or spot-on, etc., by transdermally administering, particularly by locally administering the active compound on the skin of the animals, making it transfer on the whole of the epithelium and further permeate into the epithelium, and causing the controlling effect to the entire body of the animals can be prepared by adding to the substituted benzamide compounds of formula (1) or the salts thereof, one or more media that are suitable for local administration, and further if necessary solubilizing agents such as absorption promoting agent, surfactants, suspending agent, dispersant, stabilizer, etc., physiologically acceptable additives such as spreading agent, thickner, preservative, antioxidants, light stabilizer and colorant, etc. to dissolve, suspend or emulsify them. The media suitable for local administration include for example water, alcohols such as ethanol, 1-propanol, 2-octyldodecanol, oleyl alcohol, benzyl alcohol, phenyl ethanol, phenoxy ethanol, ethylene glycol, propylene glycol, poly(ethylene glycol), poly(propylene glycol), glycerin, etc., glycol ethers such as diethylene glycol monobutyl ether, dipropylene glycol monomethyl ether, etc., esters such as ethyl acetate, butyl acetate, benzyl benzoate, ester of caproic acid with saturated aliphatic alcohol having a chain length of $C_{12}$ to $C_{18}$, hexyl laurate, isopropyl myristate, isopropyl palmitate, decyl oleate, oleyl oleate, diisopropyl adipate, dibutyl adipate, dibutyl phthalate, diisopropyl isophthalate, etc., amides such as N,N-dimethylacetamide, N,N-methylpyrrolidone, etc., ketones such as acetone, methyl ethyl ketone, etc., aliphatic hydrocarbons such as liquid paraffin, light liquid paraffin, etc., aromatic hydrocarbons, DMSO (dimethylsulfoxide), vegetable oils such as sesame oil, etc., synthetic oils such as ethyl oleate, fatty acid triglyceride, etc., silicone oil, and the like. The absorption promoting agents include for example fatty acid esters such as isopropyl myristate, pelargonic acid dipropylene glycol, fatty acid triglyceride, etc., DMSO (dimethylsulfoxide), silicone oil, and the like.

The liquid preparations such as solutions, suspensions, etc., that are used for administration through injections can be prepared by adding to the substituted benzamide compounds of formula (1) or the salts thereof, lipophilic or hydrophilic media, and further if necessary solubilizing agents such as suspending agent, dispersant, stabilizer, etc., physiologically acceptable additives such as acid, base or salt thereof for buffering, tonicity agent, thickner, antioxidants, protecting agent, etc. to dissolve, suspend or emulsify them. The lipophilic media include for example vegetable oils such as sesame oil, synthetic oils such as ethyl oleate, fatty acid triglyceride, etc., liposome, and the like, and the hydrophilic media include for example water, propylene glycol, and the like.

The surfactants that are used for the liquid preparations include for example anionic surfactants such as sodium lauryl sulfate, fatty alcohol sulfuric acid ether, monoethanol amine salt of monoalkylpolyglycol orthophosphate, monoethanol amine salt of dialkylpolyglycol orthophosphate, etc., cationic surfactants such as cetyl chloride trimethylammonium, etc., amphoteric surfactants such as disodium N-lauryl β-iminodipropionate, lecithin, etc., and nonionic surfactants such as sorbitan monostearate, glycerin monostearate, polyoxyethyl stearate, alkylphenol polyglycol ether, etc., and the like. The solubilizing agents include for example propylene glycol, oleic acid, poly(vinylpyrrolidone), polyoxyethylated castor oil, polyoxyethylated sorbitan ester, ethylenediamine, and the like. The spreading agents include for example dipropylene glycol monomethyl ether, isopropyl myristate, isopropyl palmitate, ester of caprylic acid with saturated aliphatic alcohol having a chain length of $C_{12}$ to $C_{15}$, ester of capric acid with saturated aliphatic alcohol having a chain length of $C_{12}$ to $C_{18}$, oleic acid, ethyl oleate, fatty acid triglyceride, silicone oil, and the like. The buffering agents include for example phosphate, and the like. The tonicity agents include for example sodium chloride, glycerin, and the like. The thickners include for example carboxymethyl cellulose sodium salt, sorbitol, dextran, and the like. The antioxidants include for example sulfite, metabisulfite, ascorbic acid, butylhydroxy toluene, butylhydroxy anisole, tocopherol, and the like. The preservatives and protecting agents include for example butanol, benzyl alcohol, trichlorobutanol, phenol, p-hydroxy benzoate, and the like. However, the media and additives used for the liquid preparations of the parasite-controlling agent composition of the present invention are not limited to the above-mentioned ones.

The semi-solid preparations can be administered by coating or spreading on the skin, or by introducing in body cavity.

The semi-solid preparations such as cream, ointment, paste, gel, etc., can be prepared by adding to the above-mentioned liquid preparations, in order to retain the parasite-controlling agent composition on the administered part, physiologically acceptable retention agents. The retention agents include for example acacia gum, alginic acid, bentonite, cellulose, xanthane gum, colloidal magnesium aluminum silicate, and the like. However, the retention agents used for the semi-solid preparations of the parasite-controlling agent composition of the present invention are not limited to the above-mentioned ones.

Next, formulation examples of the parasite-controlling agent composition of the present invention are shown. However, the formulation examples of parasite-controlling agent composition of the present invention are not limited only thereto. In the interim, in the following Formulation Examples, "part(s)" mean part(s) by weight.

(Solid Preparation)

| | |
|---|---|
| Substituted benzamide compound | 0.01 to 80 parts |
| Solid carrier | 5 to 99.99 parts |
| Surfactant | 0 to 15 parts |
| Others | 0 to 5 parts |

As other components, there may be mentioned, for example, lubricants, disintegrating agents, and the like.

(Liquid Preparation)

| | |
|---|---|
| Substituted benzamide compound | 1 to 50 parts |
| Liquid carrier | 40 to 99 parts |
| Surfactant | 0 to 50 parts |
| Others | 0 to 10 parts |

As other components, there may be mentioned, for example, suspending agents, dispersants, stabilizers, spreading agents, and the like.

Hereinafter, preparation examples of the parasite-controlling agent composition of the present invention are more specifically shown. However, the preparations of parasite-controlling agent composition of the present invention are not limited only thereto. In the interim, in the following Preparation Examples, "part(s)" mean part(s) by weight.

FORMULATION EXAMPLE 1

Wettable Powder Preparation

| | |
|---|---|
| Substituted benzamide compound No. 1-001 | 25 parts |
| Sodium diisobutylnaphthalene sulfonate | 1 part |
| Calcium n-dodecylbenzene sulfonate | 10 parts |
| Alkylaryl polyglycol ether | 12 parts |
| Sodium salt of naphthalene sulfonic acid formalin condensation product | 3 parts |
| Emulsion-type silicone | 1 part |
| Silicon dioxide | 3 parts |
| Kaolin | 45 parts |

FORMULATION EXAMPLE 2

Tablets Preparation

| | |
|---|---|
| Substituted benzamide compound No. 1-010 | 33 parts |
| Methyl cellulose | 0.8 part |
| Silicic acid (highly disperse) | 0.8 part |
| Corn starch | 25.4 parts |
| Lactose | 22.5 parts |
| Cellulose (fine crystal) | 16.5 parts |
| Magnesium stearate | 1 part |

FORMULATION EXAMPLE 3

Granules Preparation

| | |
|---|---|
| Substituted benzamide compound No. 1-001 | 5 parts |
| Silicic acid (highly disperse) | 1 part |
| Kaolin | 94 parts |

FORMULATION EXAMPLE 4

Granules Preparation

| | |
|---|---|
| Substituted benzamide compound No. 1-004 | 10 parts |
| Attapulgite | 90 parts |

FORMULATION EXAMPLE 5

Granules Preparation

| | |
|---|---|
| Substituted benzamide compound No. 1-007 | 3 parts |
| Polyethylene glycol (molecular weight 200) | 3 parts |
| Kaolin | 94 parts |

FORMULATION EXAMPLE 6

Water Solution Concentrate Preparation

| | |
|---|---|
| Substituted benzamide compound No. 1-004 | 20 parts |
| Polyoxyethylene lauryl ether | 3 parts |
| Sodium dioctylsulfosuccinate | 3.5 parts |
| Dimethyl sulfoxide | 37 parts |
| 2-Propanol | 36.5 parts |

FORMULATION EXAMPLE 7

Spray-on Solution

| | |
|---|---|
| Substituted benzamide compound No. 1-001 | 1 part |
| Propylene glycol | 10 parts |
| 2-Propanol | 89 parts |

FORMULATION EXAMPLE 8

Spray-on Solution

| | |
|---|---|
| Substituted benzamide compound No. 1-004 | 1 part |
| 2-Propanol | 40 parts |
| Propylene carbonate | 59 parts |

FORMULATION EXAMPLE 9

Spray-on Solution

| | |
|---|---|
| Substituted benzamide compound No. 1-007 | 2 parts |
| Dimethyl sulfoxide | 10 parts |
| 2-Propanol | 35 parts |
| Acetone | 53 parts |

FORMULATION EXAMPLE 10

Spot-on Solution

| | |
|---|---|
| Substituted benzamide compound No. 1-001 | 5 parts |
| Hexylene glycol | 50 parts |
| 2-Propanol | 45 parts |

FORMULATION EXAMPLE 11

Spot-on Solution

| | |
|---|---|
| Substituted benzamide compound No. 1-004 | 5 parts |
| Propylene glycol monomethyl ether | 50 parts |
| Dipropylene glycol | 45 parts |

FORMULATION EXAMPLE 12

Spot-on Solution

| | |
|---|---|
| Substituted benzamide compound No. 1-007 | 10 parts |
| Octyl palmitate | 10 parts |
| 2-Propanol | 80 parts |

FORMULATION EXAMPLE 13

Spot-on Solution

| | |
|---|---|
| Substituted benzamide compound No. 1-010 | 10 parts |
| 2-Propanol | 20 parts |
| Benzyl alcohol | 70 parts |

FORMULATION EXAMPLE 14

Spot-on Solution

| | |
|---|---|
| Substituted benzamide compound No. 1-013 | 10 parts |
| Diethylene glycol monoethyl ether | 90 parts |

FORMULATION EXAMPLE 15

Pour-on Solution

| | |
|---|---|
| Substituted benzamide compound No. 1-001 | 2 parts |
| Light liquid paraffin | 58 parts |
| Olive oil | 30 parts |
| ODO-H | 9 parts |
| Shinethu silicone | 1 part |

FORMULATION EXAMPLE 16

Pour-on Solution

| | |
|---|---|
| Substituted benzamide compound No. 1-004 | 5 parts |
| Isopropyl myristate | 10 parts |
| 2-Propanol | 85 parts |

FORMULATION EXAMPLE 17

Pour-on Solution

| | |
|---|---|
| Substituted benzamide compound No. 1-007 | 2 parts |
| Light liquid paraffin | 98 parts |

FORMULATION EXAMPLE 18

Pour-on Solution

| | |
|---|---|
| Substituted benzamide compound No. 1-010 | 2 parts |
| Hexyl laurate | 5 parts |
| Medium-chain length triglyceride | 15 parts |
| Ethanol | 78 parts |

FORMULATION EXAMPLE 19

Pour-on Solution

| | |
|---|---|
| Substituted benzamide compound No. 1-001 | 2 parts |
| Oleyl oleate | 5 parts |
| N-methyl pyrrolidone | 40 parts |
| 2-Propanol | 53 parts |

In the method for controlling parasite and hygienic pest according to the present invention, an effective amount of the substituted benzamide compound of formula (1) or salt thereof can be administered as active ingredient alone, and if necessary, it can be administered in admixture with other insecticides, acaricides, antiparasitic agents, antibacterial agents, etc., by mixing them at the time of preparing the formulation or at the time of administration.

By the administration in admixture with other insecticides, acaricides, antiparasitic agents or antibacterial agents, or the like, enlargement in control spectrum due to additive or synergistic effect of mixed agents each other, improvement in parasite- and hygienic pest-controlling effect, cost reduction due to reduction in a dose to be applied, and further prolonged controlling effect over long time can be expected. Particularly, the administration in admixture with other insecticides, acaricides, antiparasitic agents that are different in the acting mechanism is extremely effective from the viewpoint of preventing parasites and hygienic pests from acquiring drug resistance. In this case, a combination with plural known insecticides, known acaricides, known antiparasitic agents or known antibacterial agents at the same time can be used.

As the kinds of the insecticides, acaricides, antiparasitic agents or antibacterial agents that can be used in admixture with the substituted benzamide compound of formula (1), specific examples of the general names can be enumerated below, but the invention is not necessarily limited only thereto.

Insecticides: abamectin, acephate, acetamiprid, alanycarb, aldicarb, allethrin, azamethiphos, azinphos-ethyl, azinphos-methyl, *bacillus thuringiensis*, bendiocarb, benfluthrin, benfuracarb, bensultap, bifenthrin, bioallethrin, bioresmethrin, bistrifluoron, buprofezin, butocarboxim, carbaryl, carbofenothion, carbofuran, carbosulfan, cartap, chlorantraniliprole, chlorethoxyfos, chlorfenapyr, chlorfenvinphos, chlorfluazuron, chlormephos, chlorpyrifos, chlorpyrifos-methyl, chromafenozide, clothianidin, cyanophos, cyantraniliprole, cycloprothrin, cyfluthrin, beta-cyfluthrin, cyhalothrin, gamma-cyhalothrin, lambda-cyhalothrin, cypermethrin, alpha-cypermethrin, beta-cypermethrin, zeta-cypermethrin, cyphenothrin, cyromazine, deltamethrin, diafenthiuron, diazinon, dichlorvos, dicrotophos, diflubenzuron, dimethoate, dimethylvinphos, dinotefuran, diofenolan, disulfoton, emamectin-benzoate, empenthrin, endosulfan, alpha-endosulfan, EPN, esfenvalerate, ethiofencarb, ethiprole, etofenprox, etrimfos, fenitrothion, fenobucarb, fenoxycarb, fenthion, fenvalerate, fipronil, flonicamid, fluazuron, flubendiamide, flucycloxuron, flucythrinate, flufenerim, flufenoxuron, flumethrin, fluvalinate, tau-fluvalinate, fonofos, furathiocarb, halofenozide, hexaflumuron, hydramethylnon, imidacloprid, imiprothrin, indoxacarb, indoxacarb-MP, isoprocarb, isoxathion, lepimectin, lufenuron, malathion, meperfluthrin, metaflumizone, metaldehyde, methacrifos, methamidophos, methidathion, methomyl, methoprene, methoxychlor, methoxyfenozide, metofluthrin, mevinphos, muscalure, nitenpyram, novaluron, noviflumuron, omethoate, oxydemeton-methyl, parathion-methyl, permethrin, phenothrin, phenthoate, phorate, phosalone, phosmet, phoxim, pirimicarb, pirimiphos-methyl, profenofos, prothiofos, pymetrozine, pyraclofos, pyrethrins, pyridalyl, pyrifluquinazon, pyriprole, pyriproxyfen, resmethrin, rotenone, silafluofen, spinetoram, spinosad, spirotetramat, sulfotep, sulfoxaflor, tebufenozide, teflubenzuron, tefluthrin, terbufos, tetrachlorvinphos, tetramethrin, d-tetramethrin, tetramethylfluthrin, thiacloprid, thiamethoxam, thiocyclam, thiodicarb, thiofanox, thiometon, tolfenpyrad, tralomethrin, transfluthrin, triazamate, trichlorfon, triflumuron, ANM-138 (test name) and ME-5343 (test name), etc.

Acaricides: acequinocyl, acrinathrin, amidoflumet, amitraz, azocyclotin, benzoximate, bifenazate, bromopropylate, clofentezine, cyenopyrafen, cyflumetofen, dicofol, dienochlor, etoxazole, fenazaquin, fenbutatin oxide, fenothiocarb, fenpropathrin, fenpyroximate, fluacrypyrim, formetanate, halfenprox, hexythiazox, milbemectin, propargite, pyridaben, pyrimidifen, spirodiclofen, spiromesifen, tebufenpyrad and NNI-0711 (test name), etc.

Antiparasitic agents: acriflavine, albendazole, atovaguone, azithromycin, bithionol, bromofenofos, cambendazole, camidazole, chloroquine, clazuril, clindamycin hydrochloride, clorsulon, closantel, coumaphos, cymiazol, dichlorophen, diethylcarbamazine, diminazene, disophenol, dithiazanine iodide, doxycycline hydrochloride, doramectin, emodepside, eprinomectin, febantel, fenbendazole, flubendazole, furazolidone, glycalpyramide, imidocarb, ivermectin, levamisole, mebendazole, mefloquine, melarsamine hydrochloride, metronidazole, metyridine, milbemycin oxime, monepantel, morantel tartrate, moxidectin, nicarbazin, niclosamide, nitroscanate, nitroxynil, omphalotin, oxantel pamoate, oxantel tartrate, oxfendazolee, oxibendazole, oxyclozanide, pamaquine, phenothiazine, piperazine adipate, piperazine citrate, piperazine phosphate, PNU-97333 (paraherquamide A), PNU-141962 (2-deoxyparaherquamide), praziquantel, primaquine, propetamphos, propoxur, pyrantel pamoate, pyrimethamine, santonin, selamectin, sulfadimethoxine, sulfadoxine, sulfamerazine, sulfamonomethoxine, sulfamoildapsone, thiabendazole, tinidazole, toltrazuril, tribromsalan and triclabendazole, etc.

Antibacterial agents: amoxicillin, ampicillin, cefapirin, cefazolin, cefquinome, ceftiofur, chlortetracycline, clavulanic acid, danofloxacin, difloxacin, dinitolmide, enrofloxacin, florfenicol, lincomycin, lomefloxacin, marbofloxacin, miloxacin, mirosamycin, norfloxacin, ofloxacin, orbifloxacin, oxolinic acid, oxytetracycline, penicillin, thiamphenicol, tiamulin fumarate, tilmicosin phosphate, acetylisovaleryltylosin, tylosin phosphate, tulathromycin and valnemulin, etc.

Antifungal agents: ketoconazole and miconazole nitrate, etc.

EXAMPLES

Hereinafter, the present invention will be explained in more detail by specifically referring to Synthetic Examples and Test Examples of the substituted benzamide compound of formula (1) used as the active ingredient of the present invention, but the present invention is not limited to these Examples.

In the meantime, physical property (melting point) described in Synthetic Examples was measured with a micromelting point system (MP-J3) manufactured by Yanaco Laboratory instrument development Co., LTD., and spectral data ($^1$H NMR) were measured with a nuclear magnetic resonance spectrometer (ECX-300 or ECP-300) manufactured by JEOL Ltd.

Synthetic Examples

Synthetic Example 1

4-[5-(3,5-Dichlorophenyl)-4,5-dihydro-5-(trifluoromethyl)isoxazol-3-yl]-2-methyl-N-(thietan-3-yl)benzoic acid amide (Compound No. 1-001)

To a solution of 3.08 g of 4-[5-(3,5-dichlorophenyl)-4,5-dihydro-5-(trifluoromethyl)isoxazol-3-yl]-2-methylbenzoyl chloride (WO 2007/026965; Step 4 of Synthetic Example 1) in 5 mL of dichloromethane, 1.00 g of thietan-3-yl amine hydrobromide and 1.78 g of triethylamine were added under cooling with ice and with stirring, and stirred at room temperature for 18 hours. After the completion of the reaction, 50 mL of water was added to the reaction mixture, was extracted with chloroform (50 mL×1), the organic phase was washed with water, and dehydrated and dried with saturated sodium chloride aqueous solution and anhydrous sodium sulfate in that order, and then the solvent was distilled off under reduced pressure. The residue was purified with silica gel column chromatography that was eluted with ethyl acetate-hexane (1:9 to 1:1 gradient), and 2.10 g of the aimed product was obtained as white crystal. Melting point: 158.0-159.0° C.

$^1$H NMR (CDCl$_3$, Me$_4$Si, 300 MHz) δ7.35-7.6 (m, 6H), 6.30 (d, J=7.9 Hz, 1H), 5.40 (sxt, J=8.3 Hz, 1H), 4.08 (d, J=18.2 Hz, 1H), 3.69 (d, J=18.2 Hz, 1H), 3.35-3.55 (m, 4H), 2.45 (s, 3H).

Synthetic Example 2

4-[5-(3,5-Dichlorophenyl)-4,5-dihydro-5-(trifluoromethyl)isoxazol-3-yl]-2-methyl-N-(1-oxothietan-3-yl)benzoic acid amide (Compound No. 1-002) and 4-[5-(3,5-dichlorophenyl)-4,5-dihydro-5-(trifluoromethyl)isoxazol-3-yl]-2-methyl-N-(1,1-dioxothietan-3-yl)benzoic acid amide (Compound No. 1-003)

To a solution of 1.46 g of 4-[5-(3,5-dichlorophenyl)-4,5-dihydro-5-(trifluoromethyl)isoxazol-3-yl]-2-methyl-N-(thietan-3-yl)benzoic acid amide (Compound No. 1-001) in 5 mL of dichloromethane, a solution of 0.44 g of 3-chloroperbenzoic acid (75%) in 5 mL of dichloromethane was added dropwise at 0° C. with stirring, and after the completion of dropwise addition, the mixture was stirred at room temperature for 2 hours. After the completion of the reaction, 50 mL of saturated sodium hydrogen carbonate aqueous solution was added to the reaction mixture, was extracted with chloroform (50 mL×1), the organic phase was washed with water, and dehydrated and dried with saturated sodium chloride aqueous solution and anhydrous sodium sulfate in that order, and then the solvent was distilled off under reduced pressure. The residue was purified with silica gel column chromatography that was eluted with ethyl acetate-hexane (1:9 to 10:0 gradient), and then with methanol-ethyl acetate (1:4), and 0.25 g of 4-[5-(3,5-dichlorophenyl)-4,5-dihydro-5-(trifluoromethyl)isoxazol-3-yl]-2-methyl-N-(1-oxothietan-3-yl)benzoic acid amide and 0.162 g of 4-[5-(3,5-dichlorophenyl)-4,5-dihydro-5-(trifluoromethyl)isoxazol-3-yl]-2-methyl-N-(1,1-dioxothietan-3-yl)benzoic acid amide were obtained as white crystal respectively.

4-[5-(3,5-Dichlorophenyl)-4,5-dihydro-5-(trifluoromethyl)isoxazol-3-yl]-2-methyl-N-(1-oxothietan-3-yl)benzoic acid amide Melting point: 106.0-108.0° C.
$^1$H NMR (CDCl$_3$, Me$_4$Si, 300 MHz) δ7.5-7.6 (m, 4H), 7.4-7.45 (m, 2H), 6.49 (d, J=7.6 Hz, 1H), 4.69 (sxt, J=7.9 Hz, 1H), 4.15-4.25 (m, 2H), 4.08 (d, J=17.5 Hz, 1H), 3.69 (d, J=17.5 Hz, 1H), 3.26 (dt, J=12.4, 3.1 Hz, 2H), 2.46 (s, 3H).

4-[5-(3,5-dichlorophenyl)-4,5-dihydro-5-(trifluoromethyl)isoxazol-3-yl]-2-methyl-N-(1,1-dioxothietan-3-yl)benzoic acid amide Melting point: 189.0-191.0° C.
$^1$H NMR (CDCl$_3$, Me$_4$Si, 300 MHz) δ7.5-7.55 (m, 4H), 7.4-7.45 (m, 2H), 6.61 (d, J=7.2 Hz, 1H), 4.8-4.95 (m, 1H), 4.55-4.65 (m, 2H), 4.08 (d, J=17.5 Hz, 1H), 4.0-4.05 (m, 2H), 3.70 (d, J=17.5 Hz, 1H), 2.47 (s, 6H).

Synthetic Example 3

4-[5-(3,5-Dibromo-4-fluorophenyl)-4,5-dihydro-5-(trifluoromethyl)isoxazol-3-yl]-2-methyl-N-(thietan-3-yl)benzoic acid amide (Compound No. 1-004)

Step 1: Production of 3,5-dibromo-4-fluoro-1-(1-trifluoromethylethenyl)benzene

To a solution of 6.12 g of methyltriphenylphosphonium bromide in 60 mL of tetrahydrofuran, 1.93 g of potassium tert-butoxide was added, and stirred at 0° C. for 1 hour. Then, to the reaction mixture, under cooling with ice and with stirring, 3.00 g of 1-(3,5-dibromo-4-fluorophenyl)-2,2,2-trifluoroethanone (WO 2011/027051; Synthetic Example 17) was added, and continued to stir at room temperature for 18 hours. After the completion of the reaction, precipitated solid was removed through filtration with Celite, and the solvent was distilled off under reduced pressure. The residue was purified with silica gel column chromatography that was eluted with ethyl acetate-hexane (0:10 to 2:8 gradient), and 1.92 g of the aimed product was obtained as colorless oily substance.

¹H NMR (CDCl₃, Me₄Si, 300 MHz) δ7.59 (d, J=7.5 Hz, 2H), 6.04 (d, J=1.5 Hz, 1H), 5.78 (d, J=1.5 Hz, 1H).

Step 2: Production of methyl 4-[5-(3,5-dibromo-4-fluorophenyl)-5-trifluoromethyl-4,5-dihydroisoxazol-3-yl]-2-methyl benzoate To a solution of 180 mg of methyl 4-(hydroxyiminomethyl)-2-methyl benzoate in 5 mL of 1,2-dimethoxyethane, 124 mg of N-chlorosuccinimide was added, and stirred at 80° C. for 2 hours. Then, the reaction mixture was cooled to 0° C., 296 mg of 3,5-dibromo-4-fluoro-1-(1-trifluoromethylethenyl)benzene and 186 mg of potassium hydrogen carbonate were added, and continued to stir at room temperature further for 18 hours. After the completion of the reaction, the reaction mixture was poured to 50 mL of ice water, extracted with ethyl acetate (25 mL×2), the organic phase was washed with water, and dehydrated and dried with saturated sodium chloride aqueous solution and anhydrous sodium sulfate in that order, and then the solvent was distilled off under reduced pressure. The residue was purified with silica gel column chromatography that was eluted with ethyl acetate-hexane (1:9 to 1:1 gradient), and 341 mg of the aimed product was obtained as pale yellow resinous substance.

¹H NMR (CDCl₃, Me₄Si, 300 MHz) δ7.96 (d, J=9.0 Hz, 1H), 7.77 (d, J=5.9 Hz, 2H), 7.45-7.55 (m, 2H), 4.10 (d, J=17.9 Hz, 1H), 3.91 (s, 3H), 3.72 (d, J=17.9 Hz, 1H), 2.62 (s, 3H).

Step 3: Production of 4-[5-(3,5-dibromo-4-fluorophenyl)-5-trifluoromethyl-4,5-dihydroisoxazol-3-yl]-2-methyl benzoic acid To a solution of 341 mg of methyl 4-[5-(3,5-dibromo-4-fluorophenyl)-5-trifluoromethyl-4,5-dihydroisoxazol-3-yl]-2-methyl benzoate in 10 mL of ethanol and 3 mL of tetrahydrofuran, 1.27 mL of 1N potassium hydroxide aqueous solution was added, and stirred at room temperature for 2 hours. After the completion of the reaction, the solvent was distilled off under reduced pressure, 10 mL of water was added to the residue, and concentrated hydrochloric acid was added under cooling with ice and with stirring. After the reaction mixture was adjusted to pH 2, it was extracted with chloroform (10 mL×2). The combined organic phase was washed with 20 mL of water, and then dehydrated and dried with saturated sodium chloride aqueous solution and anhydrous sodium sulfate in that order, and then the solvent was distilled off under reduced pressure, and 330 mg of the aimed product was obtained as pale yellow resinous substance.

¹H NMR (CDCl₃, Me₄Si, 300 MHz) δ8.02 (d, J=9.0 Hz, 1H), 7.77 (d, J=5.5 Hz, 2H), 7.54 (s, 1H), 7.53 (d, J=9.0 Hz, 1H), 4.11 (d, J=17.9 Hz, 1H), 3.71 (d, J=17.9 Hz, 1H), 2.65 (s, 3H).

Step 4: Production of 4-[5-(3,5-dibromo-4-fluorophenyl)-4,5-dihydro-5-(trifluoromethy)isoxazol-3-yl]-2-methyl-N-(thietan-3-yl)benzoic acid amide To a solution of 330 mg of 4-[5-(3,5-dibromo-4-fluorophenyl)-5-trifluoromethyl-4,5-dihydroisoxazol-3-yl]-2-methyl benzoic acid in 5 mL of dichloromethane, 129 mg of thietan-3-yl amine hydrobromide, 154 mg of triethylamine, 5 mg of 1-hydroxybenzotriazole and 146 mg of 1-[3-(diethylamino)propyl]-3-ethylcarbodiimide hydrochloride were added, and stirred at room temperature for 18 hours.

After the completion of the reaction, 20 mL of chloroform was added to the reaction mixture, washed with water (20 mL×1), and the organic phase was dehydrated and dried with saturated sodium chloride aqueous solution and anhydrous sodium sulfate in that order, and then the solvent was distilled off under reduced pressure. The residue was purified with silica gel column chromatography that was eluted with ethyl acetate-hexane (1:9 to 1:1 gradient), and 160 mg of the aimed product was obtained as white crystal.

Melting point: 179.0-181.0° C.

¹H NMR (CDCl₃, Me₄Si, 300 MHz) δ7.78 (d, J=8.4 Hz, 2H), 7.47 (s, 2H), 7.35-7.4 (m, 1H), 6.50 (bs, 1H), 5.3-5.45 (m, 1H), 4.09 (d, J=17.5 Hz, 1H), 3.71 (d, J=17.5 Hz, 1H), 3.45-3.5 (m, 4H), 2.44 and 2.42 (s, 3H).

Synthetic Example 4

4-[4-(2,6-dichloropyridin-4-yl)-4-trifluoromethyl-4,5-dihydro-3H-pyrrol-2-yl]-2-methyl-N-(thietan-3-yl) benzoic acid amide (Compound No. 5-001)

Step 1: Production of ethyl 2-methyl-4-[N—[(trimethylsilyl)methyl]carbamoyl]benzoate To a solution of 443 mg of 4-ethoxycarbonyl-3-methyl benzoic acid and 0.1 mL of N,N-dimethylforamide in 4.0 mL of dichloromethane, 324 mg of oxalyl chloride was added dropwise, and after the completion of the dropwise addition, the mixture was stirred at room temperature for 1 hour. After the completion of the reaction, the solvent was distilled off under reduced pressure, the residue was dissolved in 4.0 ml of dichloromethane, then 215 mg of triethylamine and 264 mg of (trimethylsilyl)methylamine were added, and stirred at room temperature for 1 hour. After the completion of the reaction, 5.0 mL of water was added to the reaction mixture, and extracted with chloroform (10 mL×1), and the organic phase was washed with 5.0 mL of water, then dehydrated and dried with saturated sodium chloride aqueous solution and anhydrous sodium sulfate in that order, and then the solvent was distilled off under reduced pressure. The residue was washed with diisopropylether-hexane mixed solvent, and 535 mg of the aimed product was obtained as white crystal.

¹H NMR (CDCl₃, Me₄Si, 300 MHz) δ7.93 (d, J=8.1 Hz, 1H), 7.60 (s, 1H), 7.53 (d, J=8.1 Hz, 1H), 5.95 (bs, 1H), 4.37 (q, J=7.2 Hz, 2H), 2.97 (d, J=5.8 Hz, 2H), 2.63 (s, 3H), 1.40 (t, J=7.2 Hz, 3H), 0.14 (s, 9H).

Step 2: Production of ethyl 2-methyl-4-[N—[(trimethylsilyl)methyl]thiocarbamoyl]benzoate To a suspension of 535 mg of ethyl 2-methyl-4-[N—[(trimethylsilyl)methyl]carbamoyl]benzoate in 10 mL of toluene, 850 mg of Lawesson's reagent (2,4-bis(4-methoxyphenyl)-1,3,2,4-dithiadiphosphethane-2,4-disulfide) was added, and stirred under reflux with heat for 3 hours. After the completion of the reaction, the reaction mixture was cooled to room temperature, poured in 10 ml of water, extracted with ethyl acetate (10 ml×2). The combined organic phase was washed with 10 mL of water, and dehydrated and dried with saturated sodium chloride aqueous solution and then with anhydrous sodium sulfate, and then the solvent was distilled off under reduced pressure. The residue was purified with silica gel column chromatography that was eluted with ethyl acetate-hexane (1:3 to 1:1 gradient), and 670 mg of the aimed product was obtained as pale yellow oily substance.

$^1$H NMR (CDCl$_3$, Me$_4$Si, 300 MHz) δ7.72 (d, J=8.1 Hz, 1H), 7.38 (s, 1H), 7.29 (d, J=8.1 Hz, 1H), 4.18 (q, J=6.9 Hz, 2H), 3.34 (d, J=6.0 Hz, 2H), 2.44 (s, 3H), 1.21 (t, J=6.9 Hz, 3H), 0.19 (s, 9H).

Step 3: Production of ethyl 2-methyl-4-[methylthio[(trimethylsilyl)methylimino]methyl]benzoate To a solution of 670 mg of ethyl 2-methyl-4-[N—[(trimethylsilyl)methyl]thiocarbamoyl]benzoate in 10 mL of tetrahydrofuran, 257 mg of potassium tert-butoxide was added dropwise under cooling with ice and with stirring, and stirred at room temperature for 15 minutes. Then, 325 mg of methyl iodide was added to the reaction mixture, and continued to stir at the same temperature further for 12 hours. After the completion of the reaction, 20 mL of water was added to the reaction mixture, and extracted with ethyl acetate (15 ml×2). The combined organic phase was washed with 10 mL of water, and dehydrated and dried with saturated sodium chloride aqueous solution and anhydrous sodium sulfate in that order, and then the solvent was distilled off under reduced pressure, and 320 mg of the aimed product was obtained as pale yellow oily substance. The resulting product was used as such without further purification for the next step.

Step 4: Production of ethyl 4-[4-(2,6-dichloropyridin-4-yl)-4-trifluoromethyl-4,5-dihydro-3H-pyrrol-2-yl]-2-methyl benzoate To a solution of 320 mg of ethyl 2-methyl-4-[methylthio[(trimethylsilyl)methylimino]methyl]benzoate and 359 mg of 2,6-dichloro-4-[1-(trifluoromethyl)ethenyl]pyridine in 10 mL of tetrahydrofuran, 0.25 mL of 1M tetrahydrofuran solution of tetrabutyl ammonium fluoride was added dropwise under cooling with ice and with stirring, and after the completion of the dropwise addition, the mixture was stirred at room temperature for 12 hours. After the completion of the reaction, 10 mL of water was added to the reaction mixture, and extracted with ethyl acetate (10 ml×2). The combined organic phase was washed with 5 mL of water, and dehydrated and dried with saturated sodium chloride aqueous solution and anhydrous sodium sulfate in that order, and then the solvent was distilled off under reduced pressure. The residue was purified with silica gel column chromatography that was eluted with ethyl acetate-hexane (1:20 to 1:3 gradient), and 320 mg of the aimed product was obtained as pale yellow oily substance.

$^1$H NMR (CDCl$_3$, Me$_4$Si, 300 MHz) δ7.97 (d, J=8.1 Hz, 1H), 7.73 (s, 1H), 7.69 (d, J=8.1 Hz, 1H), 7.29 (s, 2H), 4.91 (d, J=17.1 Hz, 1H), 4.45 (d, J=17.1 Hz, 1H), 4.38 (q, J=7.2 Hz, 2H), 3.83 (d, J=17.4 Hz, 1H), 3.46 (d, J=17.4 Hz, 1H), 2.65 (s, 3H), 1.41 (t, J=7.2 Hz, 3H).

Step 5: Production of 4-[4-(2,6-dichloropyridin-4-yl)-4-trifluoromethyl-4,5-dihydro-3H-pyrrol-2-yl]-2-methyl benzoic acid To a solution of 320 mg of ethyl 4-[4-(2,6-dichloropyridin-4-yl)-4-trifluoromethyl-4,5-dihydro-3H-pyrrol-2-yl]-2-methyl benzoate in 5 mL of tetrahydrofuran, 5 mL of 10% sodium hydroxide acqueous solution and 50 mg of tetrabutyl ammonium bromide were added, and stirred at room temperature for 6 hours. After the completion of the reaction, concentrated hydrochloric acid was added dropwise to the reaction mixture under cooling with ice and with stirring, and the reaction mixture was adjusted to pH 2, and then extracted with ethyl acetate (15 ml×1). The organic phase was dehydrated and dried with saturated sodium chloride aqueous solution and anhydrous sodium sulfate in that order, and then the solvent was distilled off under reduced pressure, and 240 mg of the aimed product was obtained as blown solid. The resulting product was used as such without further purification for the next step.

Step 6: Production of 4-[4-(2,6-dichloropyridin-4-yl)-4-trifluoromethyl-4,5-dihydro-3H-pyrrol-2-yl]-2-methyl-N-(thietan-3-yl)benzoic acid amide To a solution of 40.0 mg of 4-[4-(2,6-dichloropyridin-4-yl)-4-trifluoromethyl-4,5-dihydro-3H-pyrrol-2-yl]-2-methyl benzoic acid in 2 mL of N,N-dimethylformamide, 57.0 mg of O-(benzotriazol-1-yl)-N,N,N',N'-tetramethyluronium hexafluorophosphate, 26.0 mg of N,N-diisopropylethylamine and 34.0 mg of thietan-3-yl amine hydrochloride were added, and stirred at room temperature for 12 hours. After the completion of the reaction, 5 mL of water was added to the reaction mixture, and extracted with ethyl acetate (10 ml×1). The organic phase was washed with 5 mL of water, and dehydrated and dried with saturated sodium chloride aqueous solution and anhydrous sodium sulfate in that order, and then the solvent was distilled off under reduced pressure. The residue was purified with silica gel column chromatography that was eluted with ethyl acetate-hexane (1:3 to 1:2 gradient), and 23.3 mg of the aimed product was obtained as colorless resinous substance.

$^1$H NMR (CDCl$_3$, Me$_4$Si, 300 MHz) δ7.72 (s, 1H), 7.68 (d, J=7.8 Hz, 1H), 7.44 (d, J=7.8 Hz, 1H), 7.28 (s, 2H), 6.27 (d, J=7.8 Hz, 1H), 5.35-5.5 (m, 1H), 4.90 (d, J=17.1 Hz, 1H), 4.44 (d, J=17.1 Hz, 1H), 3.81 (d, J=17.4 Hz, 1H), 3.35-3.55 (m, 5H), 2.49 (s, 3H).

The substituted benzamide compounds of formula (1) that are used as the active ingredient of the present invention can be produced according to the production methods described in the above-mentioned patent documents and the above-mentioned synthetic examples. The examples of the substituted benzamide compounds produced similarly to Synthetic Examples 1 to 4 are shown in Tables 4 to 8 to which the substituted benzamide compounds of formula (1) that are used as the active ingredient of the present invention are not limited.

In Tables, the indication "Et" means ethyl, and in Tables, heterocyclic rings of E-3a-1, E-3a-2, E-3a-3 and E-6-1 are the following structures, respectively

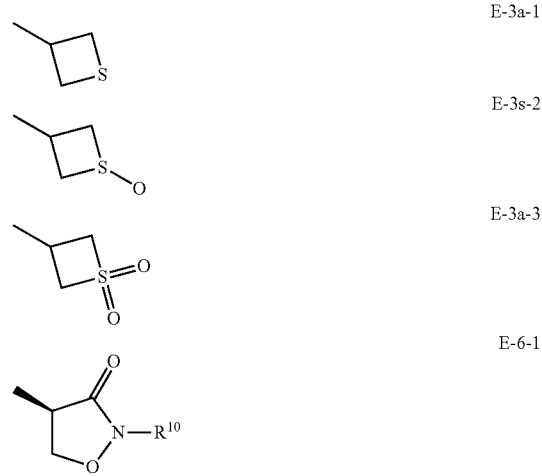

For example, the indication of "[(E-6-1)Et]" means "(R)-2-ethyl-3-oxo-2,3,4,5-tetrahydroisoxazol-4-yl".

In addition, the indication of "*1" in the Tables means that the physical property of the compound was "resinous".

TABLE 4

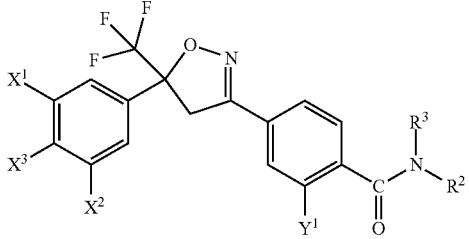

| No. | X¹ | X³ | X² | Y¹ | R³ | R² | m.p. (° C.) |
|---|---|---|---|---|---|---|---|
| 1-001 | Cl | H | Cl | CH₃ | H | E-3a-1 | 158.0-159.0 |
| 1-002 | Cl | H | Cl | CH₃ | H | E-3a-2 | 106.0-108.0 |
| 1-003 | Cl | H | Cl | CH₃ | H | E-3a-3 | 189.0-191.0 |
| 1-004 | Br | F | Br | CH₃ | H | E-3a-1 | 179.0-181.0 |
| 1-005 | Br | F | Br | CH₃ | H | E-3a-2 | 128.0-130.0 |
| 1-006 | Br | F | Br | CH₃ | H | E-3a-3 | 113.0-115.0 |
| 1-007 | CF₃ | H | Cl | CH₃ | H | E-3a-1 | 170.0-172.0 |
| 1-008 | CF₃ | H | Cl | CH₃ | H | E-3a-2 | 108.0-110.0 |
| 1-009 | CF₃ | H | Cl | CH₃ | H | E-3a-3 | 74.0-76.0 |
| 1-010 | CF₃ | H | Br | CH₃ | H | E-3a-1 | 131.0-133.0 |
| 1-011 | CF₃ | H | Br | CH₃ | H | E-3a-2 | 108.0-110.0 |
| 1-012 | CF₃ | H | Br | CH₃ | H | E-3a-3 | 104.0-106.0 |
| 1-013 | Cl | H | Cl | CH₃ | H | (E-6-1)Et | 197.0-200.0 |
| 1-014 | Cl | H | Cl | CH₃ | H | (E-6-1)CH₂CF₃ | 205.0-218.0 |

TABLE 5

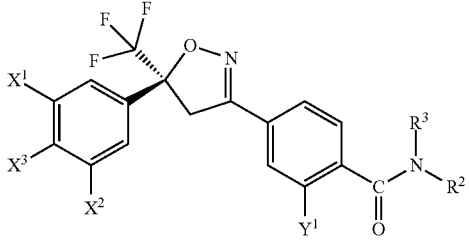

| No. | X¹ | X³ | X² | Y¹ | R³ | R² | m.p. (° C.) |
|---|---|---|---|---|---|---|---|
| 2-001 | Cl | H | Cl | CH₃ | H | (E-6-1)Et | *1 |

TABLE 6

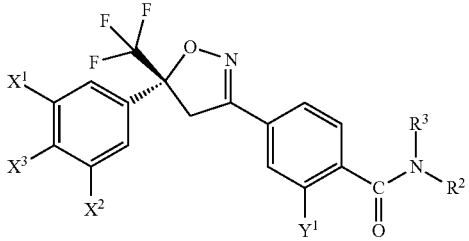

| No. | X¹ | X³ | X² | Y¹ | R³ | R² | m.p. (° C.) |
|---|---|---|---|---|---|---|---|
| 3-001 | Cl | H | Cl | CH₃ | H | (E-6-1)Et | 213.0-217.0 |

TABLE 7

| No. | X¹ | X² | Y¹ | R³ | R² | m.p. (° C.) |
|---|---|---|---|---|---|---|
| 4-001 | Cl | Cl | CH₃ | H | E-3a-1 | *1 |

TABLE 8

| No. | X¹ | X² | Y¹ | R³ | R² | m.p. (° C.) |
|---|---|---|---|---|---|---|
| 5-001 | Cl | Cl | CH₃ | H | E-3a-1 | *1 |

¹H NMR data of the substituted benzamide compounds of formula (1) described in 5 and 7 are shown in Table 9.

TABLE 9

| No. | ¹H NMR (CDCl₃, Me₄Si, 300 MHz) |
|---|---|
| 2-001 | 92.2% d.e. |
| | δ 7.3-7.55 (m, 6H), 6.55 (s, 1H), 4.96 (t, J = 8.1 Hz, 1H), 4.84 (td, J = 10.5, 8.1 Hz, 1H), 3.95-4.15 (m, 2H), 3.55-3.75 (m, 3H), 2.48 (s, 3H), 1.26 (t, J = 7.2 Hz, 3H), |
| 4-001 | δ 7.98 (s, 1H), 7.84 (s, 1H), 7.81 (s, 1H) 7.67 and 7.63 (d, J = 8.1 Hz, 2H), 7.39 and 7.33 (d, J = 8.1 Hz, 2H), 6.02 and 5.07 (q, J = 6.9 HZ, 1H) 4.14 and 4.13 (d, J = 17.4 Hz, 1H), 3.71 (d, J = 17.4 Hz, 1H), 2.85-3.5 (m, 2H), 2.20 and 2.17 (s, 3H), 1.66 and 1.54 (d, J = 7.2 Hz, 3H), 1.02 and 0.99 (t, J = 7.2 Hz, 3H). |

TEST EXAMPLES

Next, usefulness of the parasite-controlling agents of the present invention is specifically explained in the following Test Examples to which the present invention is not limited.

Test Example 1

Insecticidal Test Against Cat Flea

A chemical solution having a concentration of 100 ppm was prepared by dissolving 3.5 mg of a substituted benzamide compound in 35 mL of acetone. The chemical solution was diluted to one-tenth concentration to obtain an acetone solution (a concentration of 10 ppm), 350 μL of the acetone solution was coated on the bottom face and the lateral face of a glass container having an inner wall surface area of 35 cm², and then thin film of the substituted benzamide compound was formed in the inner wall of the glass container by vaporizing acetone. As the inner wall surface area of the glass container used is 35 cm², a treated dosage is 0.1 μg/cm². In the glass container, 5-cat flea (*Ctenocephalides felis*) in the adult stage (male and female) were released, and the glass container was covered with a lid and placed at a thermostat chamber at 25° C. A number of dead insect(s) after 4 days was counted and a rate of dead insects was calculated by the following calculation equation. Incidentally, the test was carried out with two districts.

Rate of dead insects(%)=(Number of dead insects/
Number of released insects)×100

As a result, the following compounds showed a rate of dead insects of 80% or more among the compounds tested.
Substituted benzamide compounds: No. 1-001*, 1-002, 1-003, 1-004*, 1-005*, 1-006, 1-007*, 1-008*, 1-009*, 1-010*, 1-011*, 1-012*, 1-013*, 2-001*, 4-001*, 5-001.
In the above, the indication of "*" shows that the insecticidal test was carried out at a treated dosage of 0.01 μg/cm².

Test Example 2

Insecticidal Test Against American Dog Tick

A chemical solution having a concentration of 100 ppm was prepared by dissolving 3.5 mg of a substituted benzamide compound in 35 mL of acetone. The chemical solution was diluted to one-one hundredth concentration to obtain an acetone solution (a concentration of 1 ppm), 350 μL of the acetone solution was coated on the bottom face and the lateral face of a glass container having an inner wall surface area of 35 cm², and then thin film of the substituted benzamide compound was formed in the inner wall of the glass container by vaporizing acetone. As the inner wall surface area of the glass container used is 35 cm², a treated dosage is 0.01 μg/cm². In the glass container, 5-American dog tick (*Dermacentor variabilis*) in the first nymph stage (male and female) were released, and the glass container was covered with a lid and contained at a thermostat chamber at 25° C. A number of dead insect(s) after 4 days was counted and a rate of dead insects was calculated by the calculation equation similar to that in Test Example 1. Incidentally, the test was carried out with two districts.

As a result, the following compounds showed a rate of dead insects of 80% or more among the compounds tested.
Substituted benzamide compounds: No. 1-001*, 1-002, 1-003, 1-004*, 1-005, 1-006, 1-007, 1-008, 1-009, 1-010*, 1-011, 1-013*, 2-001, 4-001, 5-001.
In the above, the indication of "*" shows that the insecticidal test was carried out at a treated dosage of 0.001 μg/cm².

Test Example 3

Insecticidal Test Against Housefly

A chemical solution having a concentration of 0.01 μg/μL was prepared by diluting a substituted benzamide compound with acetone. The chemical solution was coated on the thoracic dorsal region of female adults of housefly (*Musca domestica*) in an amount of 1 μL per fly, and the treated flies were placed at a thermostat chamber at 25° C. A number of dead insect(s) after 3 days was counted and a rate of dead insects was calculated by the calculation equation similar to that in Test Example 1. Incidentally, the test was carried out with two districts.

As a result, the following compounds showed an insecticidal rate of 90% or more among the compounds tested.
Substituted benzamide compounds: No. 1-001, 1-002, 1-003*, 1-004, 1-009, 1-010, 1-011, 1-012, 1-013.
In the above, the indication of "*" shows that the insecticidal test was carried out by use of the chemical solution having a concentration of 0.1 μg/μL.

Test Example 4

Insecticidal Test Against Mosquito

In a plastic test container of 1.9 mL (Cellstar 24 well plate, GREINER), 0.9 mL of distilled water in which 10 or more of larvas of *Culex pipiens molestus* Forskal of 1-day after hatching and a suitable amount of feed for ornamental fishes (TetraMin, Tetra Japan & Spectrum Brands, Inc.) were added was placed.

1% DMSO solution of a substituted benzamide compound was prepared, and diluted with distilled water to a concentration of 0.0001%. 0.1 mL of the diluted solution was added to the test container in which *Culex pipiens molestus* Forskal was placed (final concentration of the compound: 0.1 ppm), stirred and then placed at a thermostat chamber at 25° C. A number of dead insect(s) after 1 day was counted and a rate of dead insects was calculated by the calculation equation similar to that in Test Example 1. Incidentally, the test was carried out with two districts.

As a result, the following compounds showed a rate of dead insects of 90% or more among the compounds tested.
Substituted benzamide compounds: No. 1-001, 1-002, 1-003, 1-004, 1-008, 1-009, 1-010, 1-011, 1-012, 1-013, 4-001.

Test Example 5

Insecticidal Test Against German Cockroach

A chemical solution having a concentration of 10 μg/μL was prepared by diluting a substituted benzamide compound with acetone. The chemical solution was coated on the abdominal region of male adults of German cockroach (*Blattella germanica*) in an amount of 1 μL per cockroach, and the treated cockroaches were placed at a thermostat chamber at 25° C. A number of dead insect(s) after 2 days was counted and a rate of dead insects was calculated by the calculation equation similar to that in Test Example 1. Incidentally, the test was carried out with five districts.
As a result, the following compounds showed a rate of dead insects of 90% or more among the compounds tested.
The compounds of the present invention: No. 1-001*, 1-002*, 1-003*, 1-004*, 1-009*, 1-010*, 1-011, 1-012, 1-013*, 4-001.
In the above, the indication of "*" shows that the insecticidal test was carried out by use of the chemical solution having a concentration of 1 μg/μL, and the indication of "**" shows that the insecticidal test was carried out by use of the chemical solution having a concentration of 0.1 μg/μL.

Test Example 6

Insecticidal Test Against Termite

A 10% emulsifiable concentrate of a substituted benzamide compound was diluted with water to prepare a chemical solution with a concentration of 10 ppm. 0.5 ml of the chemical solution was added dropwise in 10 g of sand and mixed. A filter paper and the sand treated with the chemical solution were placed in a laboratory dish in which 1% agar was laid. 10-termite (*Reticulitermes flavipes*) per dish was left and placed at a thermostat chamber at 25° C. A number of dead insect(s) after 10 days was counted and a rate of dead insects was calculated by the calculation equation similar to that in Test Example 1. Incidentally, the test was carried out with two districts.

As a result, the following compounds showed a rate of dead insects of 90% or more among the compounds tested.

The compounds of the present invention: No. 1-001, 1-002, 1-003, 1-004, 1-009, 1-010, 1-011, 1-012, 1-013, 4-001*.

In the above, the indication of "*" shows that the insecticidal test was carried out by use of the chemical solution having a concentration of 100 ppm.

INDUSTRIAL APPLICABILITY

The parasite- and hygienic pest-controlling agent of the present invention can effectively control ecto- or endo-parasites and hygienic pests belonging to insects such as Hymenoptera, Diptera, Siphonaptera, Hemiptera, Psocodea, Blattaria, and Isoptera, etc., mites such as Astigmata, Oribatida, Prostigmata, Metastigmata and Mesostigmata, etc., nematodes such as Enoplida, Rhabditida, Strongylida, Oxyurida, Ascaridida and Spirurida, etc. that have developed in resistance to existing parasite- or hygienic pest-controlling agents such as organic phosphorus compounds, carbamate compounds or pyrethroides compounds with causing little adverse effect against animals to be protected such as mammals, birds and like.

The invention claimed is:

1. A method for controlling parasites and hygienic pests comprising:
administering to an animal a parasite- and hygienic pest-controlling composition comprising as active ingredient, a substituted benzamide compound of formula (1) or a salt thereof:

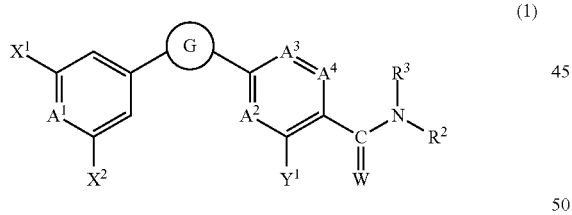

(1)

wherein $A^1$ is C—$X^3$ or nitrogen atom,
$A^2$, $A^3$ and $A^4$ are independently of one another C—$Y^2$ or nitrogen atom,
G is a heterocyclic ring of following structural formulae G-2:

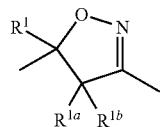

G-2

W is oxygen atom or sulfur atom,
$X^1$ is hydrogen atom, halogen atom, $C_1$-$C_3$haloalkyl, halocyclopropyl, —$OR^4$, —$SF_5$ or $C_1$-$C_3$haloalkylthio, $X^2$ is hydrogen atom, halogen atom, cyano, nitro, $C_1$-$C_3$alkyl, $C_1$-$C_3$haloalkyl, —$OR^4$, —$S(O)_pR^4$ or —$NH_2$, $X^3$ is hydrogen atom, halogen atom, cyano, methyl, methoxy, difluoromethoxy, methylthio, —$NH_2$ or dimethylamino, or $X^3$ together with $X^1$ optionally forms 5-membered or 6-membered ring together with carbon atoms to which each of $X^1$ and $X^3$ is bonded by forming —$CF_2OCF_2$—, —$OCF_2O$—, —$CF_2OCF_2O$— or —$OCF_2CF_2O$—, $Y^1$ is hydrogen atom, halogen atom, cyano, nitro, $C_1$-$C_3$alkyl, $C_1$-$C_3$haloalkyl, ($C_1$-$C_2$)alkyl substituted with $R^5$, $C_3$-$C_4$cycloalkyl, $C_1$-$C_3$alkoxy, $C_1$-$C_3$haloalkoxy, $C_1$-$C_3$alkylthio, $C_1$-$C_3$haloalkylthio, —$N(R^7)R^6$, —$C(S)NH_2$, $C_2$-$C_3$alkynyl, trimethylsilylethynyl, phenyl, phenyl substituted with $(Z)_{n1}$ or D, D is an aromatic heterocyclic ring of following structural formulae D-1 to D-3, D-7, D-11 and D-19 to D-23:

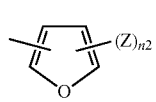

D-1

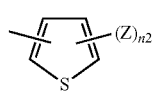

D-2

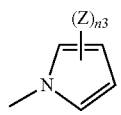

D-3

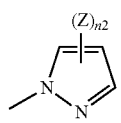

D-7

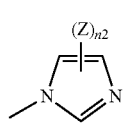

D-11

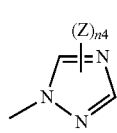

D-19

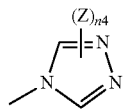

D-20

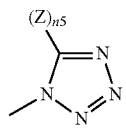

D-21

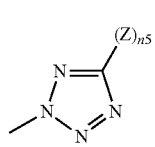

D-22

-continued

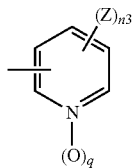
D-23

Z is halogen atom, cyano, nitro, methyl, trifluoromethyl, methoxy, methylthio, methylsulfinyl, methylsulfonyl, —$NH_2$ or dimethylamino, when n1 to n4 are an integer of 2 or more, each Z may be identical with or different from each other, $Y^2$ is hydrogen atom, halogen atom or methyl, or when two $Y^2$s are adjacent, the adjacent two $Y^2$s may form 5-membered or 6-membered ring together with carbon atoms to which the two $Y^2$s are bonded by forming =NSN= or —CH=CHCH=CH—, in this case, hydrogen atoms bonded to each carbon atom forming the ring may be arbitrarily substituted with Z, further when it is substituted with two or more Zs, each Z may be identical with or different from each other, $R^1$ is $C_1$-$C_3$haloalkyl or halocyclopropyl, $R^{1a}$ is hydrogen atom, halogen atom, $C_1$-$C_3$alkyl, $C_1$-$C_3$alkylthiomethyl, $C_1$-$C_3$haloalkylthiomethyl, $C_1$-$C_3$alkylsulfinylmethyl, $C_1$-$C_3$haloalkylsulfinylmethyl, $C_1$-$C_3$alkylsulfonylmethyl, $C_1$-$C_3$haloalkylsulfonylmethyl, —OH, $C_1$-$C_3$alkylthio or $C_1$-$C_3$alkylsulfonyl, $R^{1b}$ is hydrogen atom or halogen atom, or $R^{1b}$ together with $R^{1a}$ optionally forms $C_1$-$C_4$alkylidene, phenylmethylidene, hydroxyimino or $C_1$-$C_3$alkoxyimino, $R^2$ is a heterocyclic ring of following structural formulae E-6 or ($C_1$-$C_3$)alkyl Substituted with E-6:

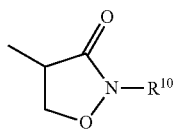
E-6

$R^3$ is hydrogen atom, $C_1$-$C_4$alkyl, ($C_1$-$C_2$)alkyl substituted with $R^{11}$, $C_3$-$C_4$cycloalkyl, $C_3$-$C_4$alkenyl, $C_3$-$C_4$alkynyl, —$C(O)R^{12}$, —$C(O)OR^{13}$, —$C(O)C(O)OR^{13}$ or $C_1$-$C_3$haloalkylthio, $R^4$ is $C_1$-$C_3$alkyl, $C_1$-$C_3$haloalkyl or $C_1$-$C_2$haloalkoxy ($C_1$-$C_2$)haloalkyl, $R^5$ is —OH, $C_1$-$C_3$alkoxy, $C_1$-$C_3$haloalkoxy, $C_1$-$C_3$alkylthio or $C_1$-$C_3$haloalkylthio, $R^6$ is hydrogen atom, $C_1$-$C_4$alkyl, —CHO, $C_1$-$C_3$alkylcarbonyl, $C_1$-$C_3$haloalkylcarbonyl, $C_3$-$C_4$cycloalkylcarbonyl, $C_1$-$C_3$alkoxycarbonyl, $C_1$-$C_3$alkylthiocarbonyl, $C_1$-$C_3$alkoxythiocarbonyl, $C_1$-$C_3$alkyldithiocarbonyl, $C_1$-$C_3$alkylsulfonyl or $C_1$-$C_3$haloalkylsulfonyl, $R^7$ is hydrogen atom or $C_1$-$C_3$alkyl, $R^{10}$ is hydrogen atom, $C_1$-$C_4$alkyl, $C_1$-$C_4$haloalkyl, hydroxy ($C_1$-$C_2$)alkyl, $C_1$-$C_3$alkoxy ($C_1$-$C_2$)alkyl, benzyl, $C_3$-$C_4$cycloalkyl, oxetan-3-yl, thietan-3-yl, $C_3$-$C_4$alkynyl, $C_3$-$C_4$alkenyl, phenyl or phenyl substituted with (Z)$_{n1}$, $R^{11}$ is cyano, $C_3$-$C_4$cycloalkyl, —$OR^{14}$, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl, $C_1$-$C_3$haloalkylsulfonyl, $C_1$-$C_3$alkoxycarbonyl, —$C(O)NH_2$, —$C(S)NH_2$, phenyl or D-23, $R^{12}$ is hydrogen atom, $C_1$-$C_4$alkyl, $C_1$-$C_4$haloalkyl, $C_1$-$C_3$alkoxy ($C_1$-$C_2$)alkyl, $C_1$-$C_3$alkylthio ($C_1$-$C_2$)alkyl, $C_1$-$C_3$alkylsulfinyl ($C_1$-$C_2$)alkyl, $C_1$-$C_3$alkylsulfonyl ($C_1$-$C_2$)alkyl, $C_3$-$C_6$cycloalkyl, $C_2$-$C_4$alkenyl, $C_2$-$C_4$alkynyl, phenyl, phenyl substituted with (Z)$_{n1}$, D-1, D-2 or D-23, $R^{13}$ is $C_1$-$C_4$alkyl, $C_1$-$C_4$haloalkyl, $C_1$-$C_3$alkoxy ($C_1$-$C_2$) alkyl, $C_3$-$C_4$alkenyl, $C_3$-$C_4$alkynyl or phenyl, $R^{14}$ is hydrogen atom, $C_1$-$C_4$alkyl, $C_1$-$C_4$haloalkyl, $C_3$-$C_4$alkenyl, $C_3$-$C_4$alkynyl, $C_1$-$C_4$alkylcarbonyl, $C_1$-$C_4$haloalkylcarbonyl, $C_3$-$C_6$cycloalkylcarbonyl or $C_1$-$C_4$alkoxycarbonyl, n1 is an integer of 1 to 5,
n2 is an integer of 0 to 3,
n3 is an integer of 0 to 4,
n4 is an integer of 0 to 2,
n5 is an integer of 0 or 1,
p is an integer of 0 to 2, and
q is an integer of 0 or 1.

2. The method according to claim 1, wherein in the parasite- and hygienic pest-controlling composition, $A^2$ is C—H,
$A^3$ and $A^4$ are independently of one another C—$Y^2$ or nitrogen atom,
$X^1$ is halogen atom, trifluoromethyl, pentafluoroethyl, trifluoromethoxy, —$SF_5$ or trifluoromethylthio,
$X^2$ is hydrogen atom, halogen atom, cyano, methyl, trifluoromethyl, methoxy, difluoromethoxy, trifluoromethoxy, difluoromethylthio or trifluoromethylthio,
$X^3$ is hydrogen atom, fluorine atom, chlorine atom, bromine atom, cyano or difluoromethoxy,
$Y^1$ is hydrogen atom, halogen atom, cyano, nitro, methyl, ethyl, trifluoromethyl, methoxymethyl, cyclopropyl, difluoromethoxy, methylthio, —$N(R^7)R^6$, —$C(S)NH_2$ or ethynyl,
$Y^2$ is hydrogen atom, or when two $Y^2$s are adjacent, the adjacent two $Y^2$s may form 6-membered ring together with carbon atoms to which the two $Y^2$s are bonded by forming —CH=CHCH=CH—,
$R^1$ is difluoromethyl, trifluoromethyl or chlorodifluoromethyl,
$R^{1a}$ is hydrogen atom, halogen atom, methyl, methylthiomethyl, methylsulfinylmethyl or methylsulfonylmethyl,
$R^{1b}$ is hydrogen atom, or $R^{1b}$ together with $R^{1a}$ optionally forms $C_2$-$C_3$alkylidene,
$R^2$ is E-6,
$R^3$ is hydrogen atom, $C_1$-$C_3$alkyl, methyl substituted with $R^{11}$, cyclopropyl, allyl, propargyl, —$C(O)R^{12}$ or —$C(O)OR^{13}$,
$R^6$ is hydrogen atom, methyl, $C_1$-$C_3$alkylcarbonyl or cyclopropylcarbonyl,
$R^7$ is hydrogen atom or methyl,
$R^{10}$ is $C_1$-$C_4$alkyl, $C_1$-$C_4$haloalkyl, $C_1$-$C_3$alkoxy ($C_1$-$C_2$) alkyl, oxetan-3-yl or $C_3$-$C_4$alkynyl,
$R^{11}$ is cyano, methoxy, ethoxy or —$C(S)NH_2$, $R^{12}$ is $C_1$-$C_4$alkyl, $C_1$-$C_3$alkoxy ($C_1$-$C_2$)alkyl, $C_3$-$C_4$cycloalkyl, $C_2$-$C_4$alkenyl or $C_2$-$C_4$alkynyl,
$R^{13}$ is $C_1$-$C_4$alkyl, $C_1$-$C_4$haloalkyl, $C_1$-$C_3$alkoxy ($C_1$-$C_2$) alkyl, $C_3$-$C_4$alkenyl or $C_3$-$C_4$alkynyl, and
q is 1.

3. The method according to claim 2, wherein in the parasite- and hygienic pest-controlling composition, $A^3$ is C—$Y^2$,
$X^1$ is halogen atom, trifluoromethyl, trifluoromethoxy or trifluoromethylthio, $X^2$ is hydrogen atom, halogen atom, cyano or trifluoromethyl, $X^3$ is hydrogen atom, fluorine atom, chlorine atom or difluoromethoxy, $Y^1$ is hydrogen atom, halogen atom, nitro, methyl, ethyl, trifluoromethyl, methoxymethyl or —N(R$^7$)R$^6$, $R^1$ is trifluoromethyl or chlorodifluoromethyl, $R^{1a}$ is hydrogen atom or halogen atom, $R^{1b}$ is hydrogen atom, $R^3$ is hydrogen atom, ethyl, cyanomethyl, methoxymethyl, propargyl, —C(O)R$^{12}$ or methoxycarbonyl, R$^6$ is hydrogen atom, methyl or acetyl, $R^{10}$ is $C_1$-$C_3$alkyl or $C_2$-$C_3$haloalkyl, and $R^{12}$ is $C_1$-$C_4$alkyl or cyclopropyl.

4. The method according to claim 3, wherein in the parasite- and hygienic pest-controlling composition, $A^3$ and $A^4$ are C—H, W is oxygen atom, $X^1$ is chlorine atom, bromine atom, iodine atom or trifluoromethyl, $X^2$ is hydrogen atom, halogen atom or trifluoromethyl, $X^3$ is hydrogen atom, fluorine atom or chlorine atom, $Y^1$ is halogen atom, nitro, methyl, ethyl or trifluoromethyl, $R^1$ is trifluoromethyl, $R^{1a}$ is hydrogen atom, and $R^3$ is hydrogen atom.

5. The method according to claim 4, wherein in the parasite- and hygienic pest-controlling composition, $A^1$ is C—X$^3$, $X^1$ is chlorine atom, bromine atom or trifluoromethyl, $X^2$ is chlorine atom, bromine atom or trifluoromethyl, $X^3$ is hydrogen atom or fluorine atom, and $Y^1$ is chlorine atom, bromine atom or methyl.

6. The method according to claim 1, wherein in the parasite- and hygienic pest-controlling composition, $R^2$ is E-6.

7. The method according to claim 1, wherein in the parasite- and hygienic pest-controlling composition, $R^{1a}$ and $R^{1b}$ are hydrogen atom, and $R^2$ is E-6.

8. The method according to claim 1, wherein in the parasite- and hygienic pest-controlling composition, $R^{1a}$ is halogen atom, $R^{1b}$ are hydrogen atom, and $R^2$ is E-6.

9. The method according to claim 1, wherein administering the compound is an oral administration.

10. The method according to claim 1, wherein administering the compound is a parenteral administration.

11. The method according to claim 10, wherein the parenteral administration is a transdermal administration.

12. The method according to claim 9, wherein in the parasite- and hygienic pest-controlling composition, the animals are mammals.

13. The method according to claim 12, wherein in the parasite- and hygienic pest-controlling composition, the mammals are rabbit, guinea pig, hamster, Mongolian gerbil, mouse, rat, squirrel, monkey, dog, ferret, cat, yak, cattle, buffalo, goat, sheep, antelope, deer, reindeer, swine, pig, camel, alpaca, llama, donkey, horse or kangaroo.

14. The method according to claim 13, wherein the parasite-and and hygienic pest-controlling composition, the mammals are dog or cat.

15. The method according to claim 1, wherein in the parasite- and hygienic pest-controlling composition, the parasite is ecto-parasitic invertebrates for animals.

16. The method according to claim 15, wherein in the parasite- and hygienic pest-controlling composition, the ecto-parasitic invertebrates for animals are flea, biting louse, louse, feather mite, itch mite, *Cheyletidae*, face mite, soft tick, hard tick, *Dermanyssidae* or *Macronyssidae*.

17. The method according to claim 16, wherein in the parasite- and hygienic pest-controlling composition, the ecto-parasitic invertebrate for animals is flea, itch mite, *Cheyletidae*, face mite, soft tick or hard tick.

* * * * *